(12) United States Patent
Ishii et al.

(10) Patent No.: US 8,821,813 B2
(45) Date of Patent: Sep. 2, 2014

(54) LIQUID-FEEDING CHIP AND ANALYSIS METHOD

(75) Inventors: Kentaro Ishii, Kanagawa (JP); Masashi Higasa, Kanagawa (JP); Shingo Hiramatsu, Kanagawa (JP)

(73) Assignee: Toray Industries, Inc. (JP)

( * ) Notice: Subject to any disclaimer, the term of this patent is extended or adjusted under 35 U.S.C. 154(b) by 118 days.

(21) Appl. No.: 12/743,248

(22) PCT Filed: Nov. 20, 2008

(86) PCT No.: PCT/JP2008/071148
§ 371 (c)(1),
(2), (4) Date: May 17, 2010

(87) PCT Pub. No.: WO2009/066737
PCT Pub. Date: May 28, 2009

(65) Prior Publication Data
US 2010/0255483 A1    Oct. 7, 2010

(30) Foreign Application Priority Data

Nov. 20, 2007  (JP) ................................. 2007-300445
Jun. 25, 2008  (JP) ................................. 2008-165644

(51) Int. Cl.
| B01L 3/00 | (2006.01) |
| B01D 45/00 | (2006.01) |
| C12M 1/00 | (2006.01) |
| G01N 35/00 | (2006.01) |

(52) U.S. Cl.
CPC ..... *B01L 3/50273* (2013.01); *B01L 2200/0621* (2013.01); *B01L 2400/0457* (2013.01); *B01L 2400/0409* (2013.01); *B01L 2300/0864* (2013.01); *G01N 2035/00158* (2013.01); *B01L 2300/087* (2013.01); *B01L 2300/0867* (2013.01); *G01N 2035/00495* (2013.01); *B01L 2200/04* (2013.01); *B01L 2300/0816* (2013.01); *B01L 2200/16* (2013.01)
USPC ............... 422/504; 422/506; 422/533; 435/4; 435/283.1; 435/288.5

(58) Field of Classification Search
None
See application file for complete search history.

(56) References Cited

U.S. PATENT DOCUMENTS 3,892,806 A     7/1975   Eckert et al.
(Continued)

FOREIGN PATENT DOCUMENTS

JP       64-025058 A    1/1989
(Continued)

OTHER PUBLICATIONS

Japanese Official Action mailed Nov. 26, 2013 from corresponding Japanese Patent Application No. 2008-557371 and an English translation.

*Primary Examiner* — Betty Forman
(74) *Attorney, Agent, or Firm* — DLA Piper LLP (US)

(57) ABSTRACT

A liquid-feeding chip for feeding a liquid utilizing the action of centrifugal force and gravity by rotating the chip around an axis of rotation, includes a first storage tank (1-1) into which the liquid can be introduced when rotation of the chip is stopped, and two or more liquid-feeding units arranged in a plurality of levels adjacent to each other, each liquid-feeding unit (U-1, U-2, U-3) being composed of a first holding tank (10-1, 20-1, 30-1), a second holding tank (10-2, 20-2, 30-2) positioned in the direction of gravity with respect to the first holding tank, and a channel B (B-1, B-2, B-3) which extends from the first holding tank in the direction of gravity and which connects the first holding tank and the second holding tank, the first holding tank at a first level being connected with a channel A (A-1) which extends from the first storage tank toward an outer circumferential side. In the liquid-feeding chip, the adjacent liquid-feeding units are connected by a channel C (C-1, C-2) which extends from the second holding tank of the liquid-feeding unit at an upper level to an outer circumferential side during rotation, and which is in communication with the first holding tank of the liquid-feeding unit at a lower level.

13 Claims, 36 Drawing Sheets

(56) References Cited

U.S. PATENT DOCUMENTS

| | | | |
|---|---|---|---|
| 4,557,600 A | 12/1985 | Klose et al. | |
| 4,812,294 A * | 3/1989 | Combs | 422/72 |
| 4,892,708 A | 1/1990 | Wogoman | |
| 5,089,417 A | 2/1992 | Wogoman | |
| 2006/0078873 A1 | 4/2006 | Ogawa et al. | |
| 2008/0292502 A1 | 11/2008 | Kitawaki et al. | |
| 2009/0087345 A1 | 4/2009 | Yamamoto | |

FOREIGN PATENT DOCUMENTS

| | | |
|---|---|---|
| JP | 2006-121935 A | 5/2006 |
| JP | 2006-189374 A | 7/2006 |
| JP | 2007-198949 A | 8/2007 |
| WO | 2004/074846 A1 | 9/2004 |
| WO | 2006/106608 A1 | 10/2006 |
| WO | 2007/105764 | 9/2007 |

* cited by examiner

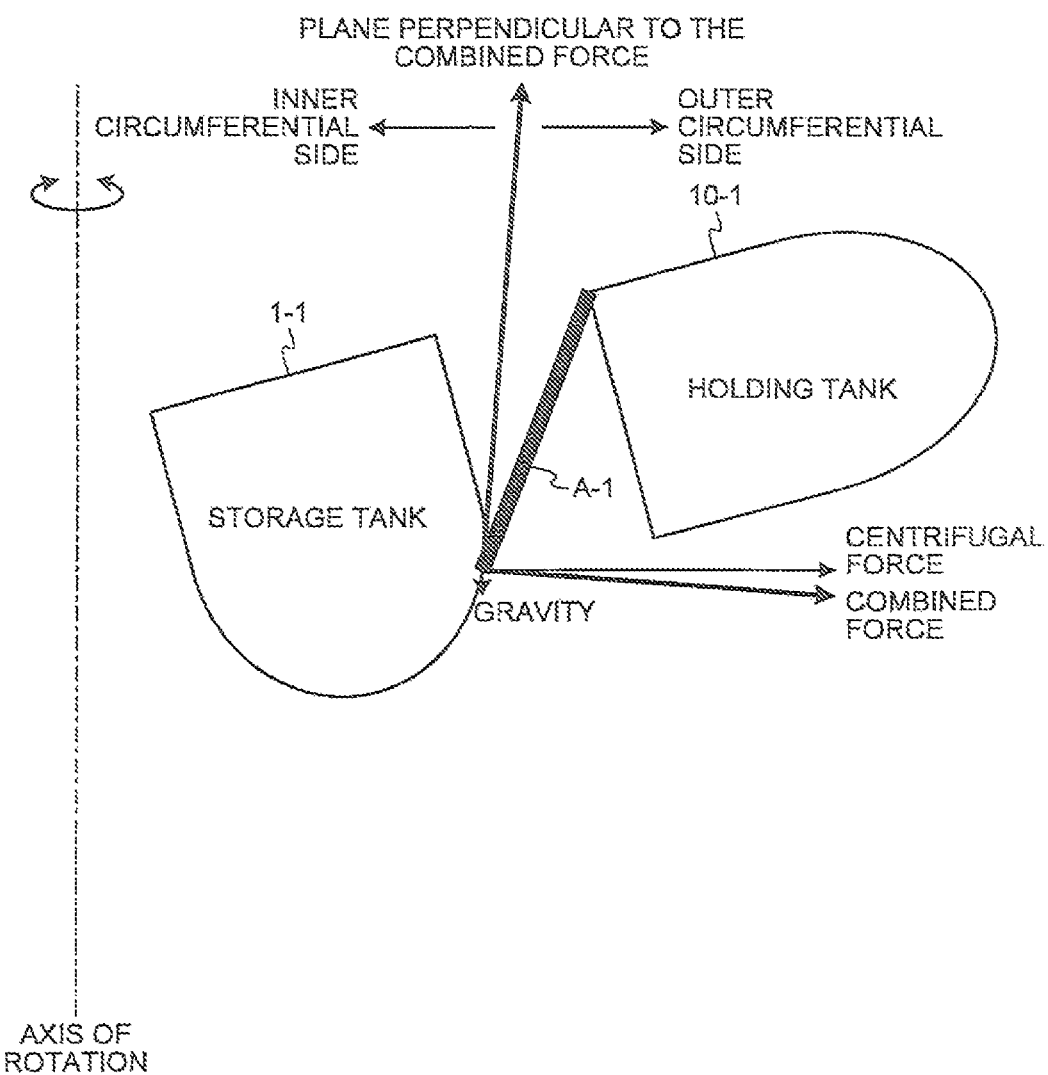

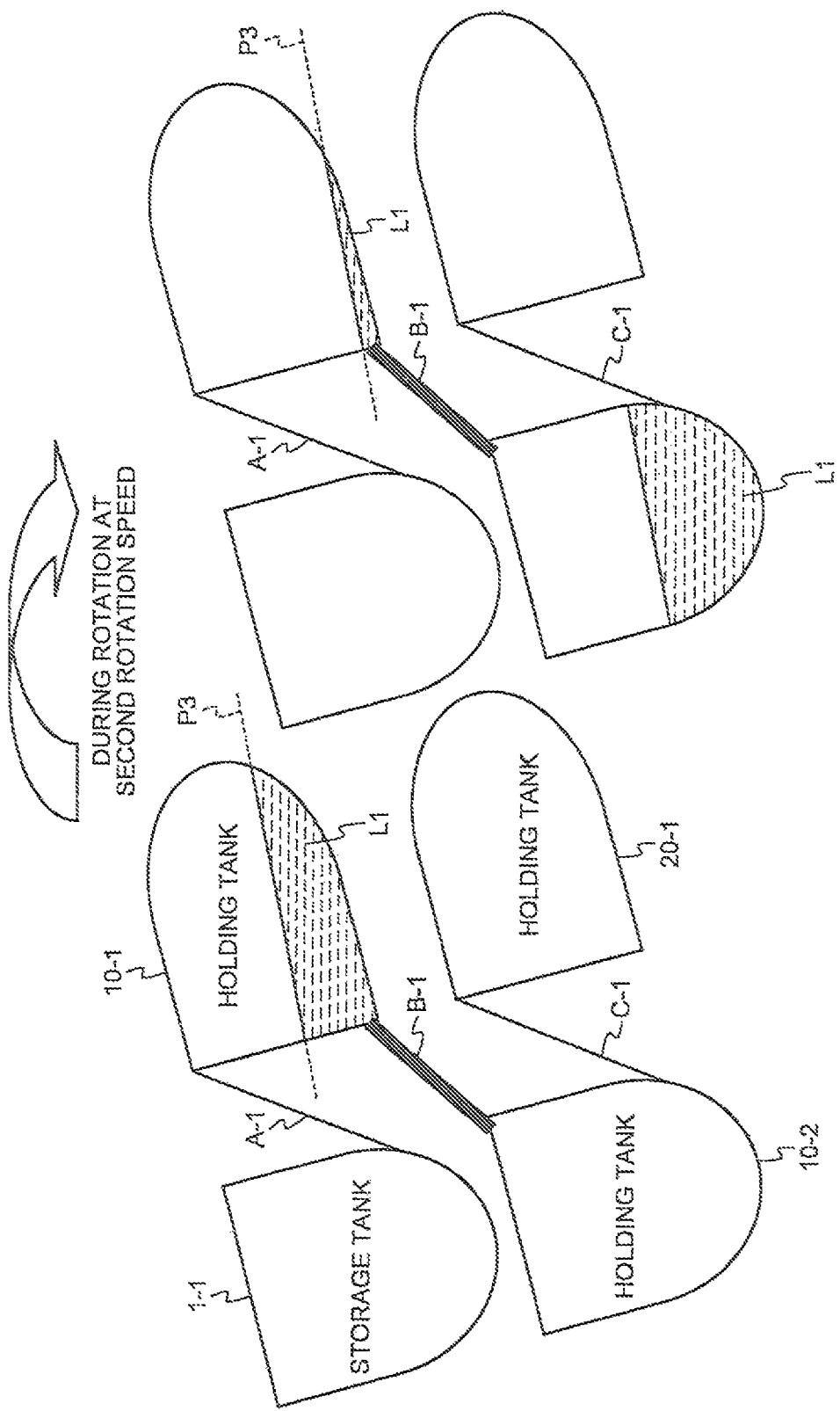

LIQUID-FEEDING CHIP AND ANALYSIS METHOD

RELATED APPLICATIONS

This is a §371 of International Application No. PCT/JP2008/071148, with an international filing date of Nov. 20, 2008 (WO 2009/066737 A1, published May 28, 2009), which is based on Japanese Patent Application Nos. 2007-300445, filed Nov. 20, 2007, and 2008-165644, filed Jun. 25, 2008, the subject matter of which is incorporated by reference.

TECHNICAL FIELD

The present invention relates to a liquid-feeding chip, and an analysis method and a liquid-feeding method using this liquid-feeding chip.

BACKGROUND

Conventionally, most analysis of trace molecules relating to clinical diagnosis, food hygiene, and environmental analysis has been carried out at clinical testing laboratories and analysis institutes using automatic analyzers. Such an analyzer includes, for example, an automatic specimen/reagent supply mechanism for supplying a specimen solution and an analysis reagent to a reaction container, reagent holding containers for holding a plurality of reagents, and an automatic cleaning mechanism for cleaning the containers by suction removal of components which are unnecessary for the detection from a liquid mixed in a reaction container. Furthermore, these analyzers need to have a high-precision control mechanism for sequentially operating these mechanisms in combination. Therefore, an automatic analyzer having these mechanisms has been a large and expensive device.

Recently, the importance of simple and fast bedside diagnosis, prevention of accidents before they occur by performing analysis and measurement at the various locations where foods are processed and imported, and performing on-site analysis of toxic substances in rivers and waste products at the river location or waste treatment plant is gaining attention. Consequently, emphasis is being placed on the development of a detection method which can perform measurement simply, rapidly, cheaply, and at a high sensitivity, and on a compact analysis device which can be used to perform on-site analysis and measurement.

In particular, in clinical diagnosis analysis, for early discovery of a sickness condition, an important problem to resolve is how to perform detection with a high degree of sensitivity using a trace amount of the specimen, while simultaneously shortening the analysis time and reducing the amount of specimen required for analysis. To resolve this problem, as a technique for analyzing a trace amount of a target substance in a specimen, new devices are being developed which can perform analysis by applying micro fabrication technology. In such devices, a channel is formed and arranged on a substrate, a liquid such as a blood from a test subject is injected into this channel, and analysis is carried out. For the analysis of a trace amount of specimen using such a device, generally, various techniques have been developed for automatically and sequentially feeding, to signify the presence of a target substance in the specimen, a labeled reagent, such as a fluorescent substance, a radioactive substance, a luminescent substance and the like, a substrate which produces fluorescence and luminescence and absorbs light by an enzyme reaction, a labeled antibody in which an antibody bound to a target substance in a specimen is labeled with an enzyme, a fluorescent substance, a radioactive substance and the like, and various washing solutions.

JP 2006-189374 describes a technique in which a testing cartridge including a plurality of containers and a substrate having a channel arranged on an approximately horizontal face is rotated by centrifugal force, so that a solution is made to move from a container on an inner circumferential side with respect to the axis of rotation to a container on an outer circumferential side with respect to the axis of rotation. However, to sequentially feed a plurality of reagents, a hole has to be drilled in order into the tiny cartridges with a drilling apparatus. Therefore, there are the problems that a precise drilling apparatus is required, and that reducing the size of the device and increasing the speed of analysis is difficult.

JP 2006-121935 describes a technique in which, for automatic measurement of a specimen, analysis is carried out by controlling liquid feeding externally from a chip using a micro feeding device such as a micro pump, and using various valve structures such as a back-flow valve and an active valve, so that a plurality of reagents are sequentially fed to a reaction chamber. However, this technique requires a chip or device mounted with mechanisms which are all complex and precise. This makes operation complex, and fails to resolve the problem of fast, simple and low-costs analysis. Furthermore, there is also the problem that the liquid is contaminated and intermingled with reagents due to liquid stagnating at a connection section with a valve section or a pump.

It could therefore be helpful to provide means capable of sequentially feeding a specimen/reagent (hereinafter sometimes referred to as "liquid") by utilizing gravity in addition to centrifugal force, which does not require a drilling apparatus, a micro feeding apparatus and the like, and which does not cause contamination or intermingling among reagents.

SUMMARY

We provide the following [1] to [15]:

[1] A liquid-feeding chip for feeding a liquid utilizing action of centrifugal force and gravity by rotating the chip around an axis of rotation, comprising, a first storage tank provided in the chip, into which the liquid can be introduced when rotation of the chip is stopped, and two or more liquid-feeding units arranged in a plurality of levels adjacent to each other, each liquid-feeding unit being composed of a first holding tank, a second holding tank positioned in a direction of gravity with respect to the first holding tank, and a channel B which extends from the first holding tank in the direction of gravity and connects the first holding tank with the second holding tank, the first holding tank at a first level being connected with a channel A which extends from the first storage tank toward an outer circumferential side, wherein the adjacent liquid-feeding units are connected by a channel C which extends from the second holding tank of the liquid-feeding unit at an upper level to an outer circumferential side during rotation and is in communication with the first holding tank of the liquid-feeding unit at a lower level.

[2] A liquid-feeding chip for feeding a liquid among a plurality of tanks in the chip utilizing action of centrifugal force and gravity while the liquid-feeding chip is mounted on a rotation apparatus and is rotated around an axis of rotation, the liquid-feeding chip comprising: a first storage tank provided in the liquid-feeding chip, into which the liquid can be introduced; a channel A which has one end connected to the first storage tank, all or a part of the channel A extending in a direction toward an outer circumference with respect to the axis of rotation; a plurality of liquid-feeding units each composed of a first holding tank, a second holding tank arranged in a direction of gravity with respect to the first holding tank, and a channel B which has one end connected to the first holding tank and another end connected to the second holding tank, the plurality of liquid-feeding units being arranged in a plurality of levels in which one end of the channel A is connected to the first holding tank at the highest level; and a channel C which connects adjacent liquid-feeding units, all or a part of the channel C extending in an outer circumferential direction with respect to the axis of rotation so that the second holding tank at an upper level is connected with the first holding tank at a lower level.

[3] The liquid-feeding chip according to the above [1], wherein at least one of the plurality of liquid-feeding units further comprises: a second storage tank positioned closer to the axis of rotation than the second holding tank; and a channel E which connects the second holding tank and the second storage tank.

[4] The liquid-feeding chip according to the above [1], wherein at least one of the plurality of liquid-feeding units further comprises: a second storage tank positioned closer to the axis of rotation than the first holding tank; and a channel E which connects the first holding tank and the second storage tank.

[5] The liquid-feeding chip according to any one of the above [1] to [4], wherein the channel B comprises an inflection portion midway along the channel which is inflected in an outer circumferential direction with respect to the axis of rotation.

[6] The liquid-feeding chip according to any one of the above [1] to [5], wherein the channel B comprises a section midway along the channel which has a smaller channel cross-sectional area than a channel cross-sectional area at a connecting portion with the first holding tank.

[7] The liquid-feeding chip according to any one of the above [1] to [6], wherein an angle formed by at least a part of the channel B and the axis of rotation is larger than an angle formed by at least a part of the channel C and the axis of rotation.

[8] The liquid-feeding chip according to any one of the above [1] to [7], further comprising a channel D which is connected to the second holding tank of the liquid-feeding unit at a lowest level, the channel D extending in an outer circumferential direction with respect to the axis of rotation.

[9] The liquid-feeding chip according to any one of the above [1] to [8], wherein the second holding tank further comprises a channel into which a liquid can be introduced, and wherein at least two of the first storage tanks and the second holding tanks included in the liquid-feeding chip store liquids different from each other in advance.

[10] The liquid-feeding chip according to any one of the above [1] to [9], wherein at least one of the first holding tanks and the second holding tanks is connected via a plurality of channels with the first storage tank at a upper level than that holding tank and/or with the first holding tank and the second holding tank at a upper level, so that different liquids introduced from the plurality of channels can be mixed.

[11] The liquid-feeding chip according to any one of the above [1] to [10], further comprising a removably-mounted reagent reservoir unit, and wherein the first storage tank and/or the second storage tank is provided in the removably-mounted reagent reservoir unit.

[12] An analysis method comprising: preparing the liquid-feeding chip according to any one of the above [1] to [11]; introducing a liquid into the first storage tank and/or the second storage tank; mounting the liquid-feeding chip into which the liquid has been introduced on a rotation apparatus and rotating the rotation apparatus at a first rotation speed to feed the liquid to the first holding tank; and rotating the liquid-feeding chip at a second rotation speed which is slower than the first rotation speed, or by stopping rotation, to feed the liquid to the second holding tank so as to analyze the liquid.

[13] The analysis method according to the above [12], wherein the liquid is any one selected from the group consisting of blood, urine, spinal liquid, saliva, phlegm, a cell suspension, a disrupted cell suspension, a nucleic acid solution, a virus suspension, a food extract, a soil extract, a blocking solution, a diluent, a denaturing agent, a labeled antibody, a labeled antigen, a non-labeled antibody, a non-labeled antigen, a labeling substance, a luminescent substrate, a fluorescent substrate, a chromogenic substrate, a hydrogen peroxide solution, a washing solution, a protein denaturing agent, a cell lysate, an enzyme solution, a labeled nucleic acid, a non-labeled nucleic acid, a primer, a probe, avidin, streptoavidin, a buffer solution, a pH adjusting solution, a hybridization solution, and an enzyme reaction terminate solution, or selected from the group consisting of a combination of two or more of these or a reaction product of two or more of these.

[14] A liquid-feeding method, comprising: preparing the liquid-feeding chip according to any one of the above [1] to [11]; introducing a liquid into the first storage tank; mounting the liquid-feeding chip into which the liquid has been introduced on a rotation apparatus and rotating the rotation apparatus at a first rotation speed to feed the liquid to the first holding tank; (a) rotating the liquid-feeding chip at a second rotation speed which is slower than the first rotation speed, or stopping rotation to feed the liquid to the second holding tank; and (b) rotating the liquid-feeding chip at the first rotation speed to feed the liquid to the first holding tank at a lower level.

[15] The liquid-feeding method according to the above [14], wherein the steps (a) and (b) are further repeated once or twice or more.

We provide a liquid-feeding chip which can sequentially feed a liquid efficiently among a plurality of tanks arranged in the chip by utilizing centrifugal force and gravity, without using complex structures such as a drilling apparatus, a micro feeding apparatus, valve structures and the like. The present invention also provides an analysis method using such a liquid-feeding chip.

BRIEF DESCRIPTION OF THE DRAWINGS

FIG. 8-1 is a schematic diagram illustrating a configuration of a storage tank, holding tanks, and channels constituting the liquid-feeding chip according to the present invention.

FIG. 8-2 is a schematic diagram illustrating a configuration of a liquid-feeding unit constituting the liquid-feeding chip according to the present invention.

FIG. 9 is an explanatory diagram illustrating a preferred position of a channel A in the liquid-feeding chip according to the present invention with respect to the centrifugal force and gravity acting on the liquid-feeding chip.

FIG. 11-1 is an explanatory diagram illustrating a preferred position of a channel B in the liquid-feeding chip according to the present invention with respect to a liquid surface in the first holding tank.

FIG. 11-2 is an explanatory diagram illustrating a preferred position of the channel B in the liquid-feeding chip according to the present invention with respect to the liquid surface in the first holding tank.

FIG. 12 is an explanatory diagram illustrating a preferred position of the channel B in the liquid-feeding chip according to the present invention with respect to the liquid surface in the first holding tank.

FIG. 22-1 is an explanatory diagram illustrating an example when a plurality of storage tanks/holding tanks are connected to a holding tank in the liquid-feeding chip according to the present invention.

FIG. 22-2 is an explanatory diagram illustrating another example when a plurality of storage tanks/holding tanks are connected to a holding tank in the liquid-feeding chip according to the present invention.

FIG. 23-1 is an explanatory diagram illustrating an example of a position of a liquid during analysis using the liquid-feeding chip according to the present invention.

FIG. 23-2 is an explanatory diagram illustrating an example of a position of a liquid during analysis using the liquid-feeding chip according to the present invention.

FIG. 23-3 is an explanatory diagram illustrating an example of a position of a liquid during analysis using the liquid-feeding chip according to the present invention.

FIG. 23-4 is an explanatory diagram illustrating an example of a position of a liquid during analysis using the liquid-feeding chip according to the present invention.

FIG. 23-5 is an explanatory diagram illustrating an example of a position of a liquid during analysis using the liquid-feeding chip according to the present invention.

FIG. 23-6 is an explanatory diagram illustrating an example of a position of a liquid during analysis using the liquid-feeding chip according to the present invention.

FIG. 23-7 is an explanatory diagram illustrating an example of a position of a liquid during analysis using the liquid-feeding chip according to the present invention.

FIG. 23-8 is an explanatory diagram illustrating an example of a position of a liquid during analysis using the liquid-feeding chip according to the present invention.

Figure 1:
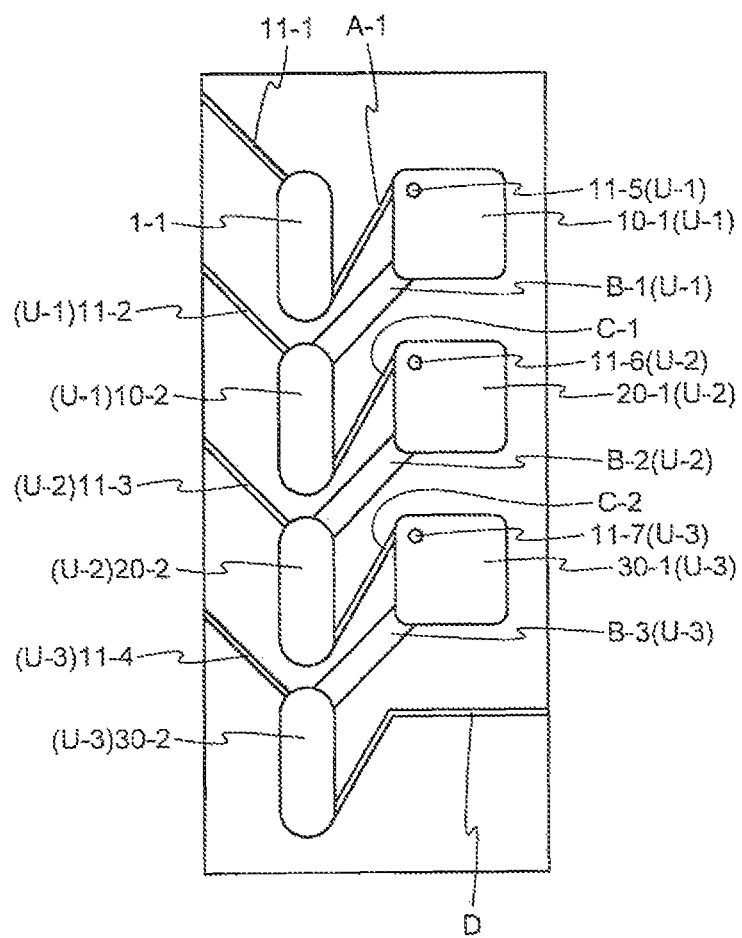
FIG. 1 is a plan view illustrating one example of a liquid-feeding chip according to the present invention.

EXPLANATIONS OF LETTERS OR NUMERALS 1-1 first storage tank
10-1 first holding tank of first level liquid-feeding unit
10-2 second holding tank of first level liquid-feeding unit
20-1 first holding tank of second level liquid-feeding unit
20-2 second holding tank of second level liquid-feeding unit
30-1 first holding tank of third level liquid-feeding unit
30-2 second holding tank of third level liquid-feeding unit
40-1 first holding tank of fourth level liquid-feeding unit
40-2 second holding tank of fourth level liquid-feeding unit
U-1 first level liquid-feeding unit
U-2 second level liquid-feeding unit (lower level liquid-feeding unit)
U-3 third level liquid-feeding unit (lower level liquid-feeding unit)
U-4 fourth level liquid-feeding unit (lower level liquid-feeding unit)
40 reaction chamber (reaction tank)
10-3 second storage tank of first level liquid-feeding unit
20-3 second storage tank of second level liquid-feeding unit
30-3 second storage tank of third level liquid-feeding unit
40-3 second storage tank of fourth level liquid-feeding unit
50 waste tank
11-1 air hole in first storage tank
11-2 air channel in communication with second holding tank of first level liquid-feeding unit
11-3 air channel in communication with second holding tank of second level liquid-feeding unit
11-4 air channel in communication with second holding tank of third level liquid-feeding unit
11-5 air hole in communication with first holding tank of first level liquid-feeding unit
11-6 air hole in communication with first holding tank of second level liquid-feeding unit
11-7 air hole in communication with first holding tank of third level liquid-feeding unit
A-1 channel A connecting first storage tank and first holding tank of first level liquid-feeding unit
B-1 channel B of first level liquid-feeding unit B-2 channel B of lower level liquid-feeding unit (second level liquid-feeding unit)
B-3 channel B of third level liquid-feeding unit
B-4 channel B of fourth level liquid-feeding unit
C-1 channel C connecting the first and second level liquid-feeding units
C-2 channel C connecting the second and third level liquid-feeding units
C-3 channel C connecting the third and fourth level liquid-feeding units
D channel D
E-1 channel E of first level liquid-feeding unit
E-2 channel E of second level liquid-feeding unit
E-3 channel E of third level liquid-feeding unit
E-4 channel E of fourth level liquid-feeding unit
F reagent reservoir unit
G liquid-feeding chip body
L1 liquid
P1 plane including liquid surface of liquid in first storage tank when liquid-feeding chip is rotated at first rotation speed
P2 plane including liquid surface of liquid in first holding tank when liquid-feeding chip is rotated at first rotation speed
P3 plane including liquid surface of liquid in first holding tank when liquid-feeding chip is rotated at second rotation speed or rotation is stopped
P4 plane including liquid surface of liquid in second holding tank when liquid-feeding chip is rotated at second rotation speed or rotation is stopped
P5 plane including liquid surface of liquid in second holding tank when liquid-feeding chip is rotated at first rotation speed
P6 plane including liquid surface of liquid in second holding tank when rotation is stopped
P7, P8, P9 plane including liquid surface of liquid in second storage tank when liquid-feeding chip is rotated at first rotation speed
Q1 connecting portion of channel A and first storage tank
Q2 connecting portion of channel B and first holding tank
Q3 connecting portion of channel C and first holding tank
Q4, Q5, Q6 connecting portion of channel E and second storage tank
Q7, Q8, Q9 connecting portion of channel E and second holding tank
R1 inflected point toward outer circumferential side in channel B at first level
R2 inflected point toward outer circumferential side in channel B at second level
R3 inflected point toward outer circumferential side in channel B at third level
R4 inflected point toward outer circumferential side in channel B at fourth level
S1 extension line of channel B
S2 extension line of channel C
S3 extension line of channel C
s1 angle formed by extension line of channel B and axis of rotation
s2 angle formed by extension line of channel C and axis of rotation
s3 angle formed by extension line of channel A and axis of rotation

DETAILED DESCRIPTION

Embodiments according to the present invention will now be described with reference to the drawings. However, the drawings merely schematically illustrate the shape, size, and arrangement of the constituent elements to the extent where the invention can be understood. The present invention is not limited to the following description. The respective constituent elements may be appropriately modified within the scope of the present invention. Further, in the drawings, patterned portions represent the liquid itself or portions where the liquid is present. In the drawings used in the following description, identical constituent elements are represented by the same reference numeral. Further, duplicate descriptions may also be omitted.

1. Liquid-Feeding Chip According to the Present Invention (Liquid-Feeding Device)

The liquid-feeding chip according to the present invention is a chip for feeding a liquid by centrifugal force and gravity by rotating the liquid-feeding chip.

Figure 2:
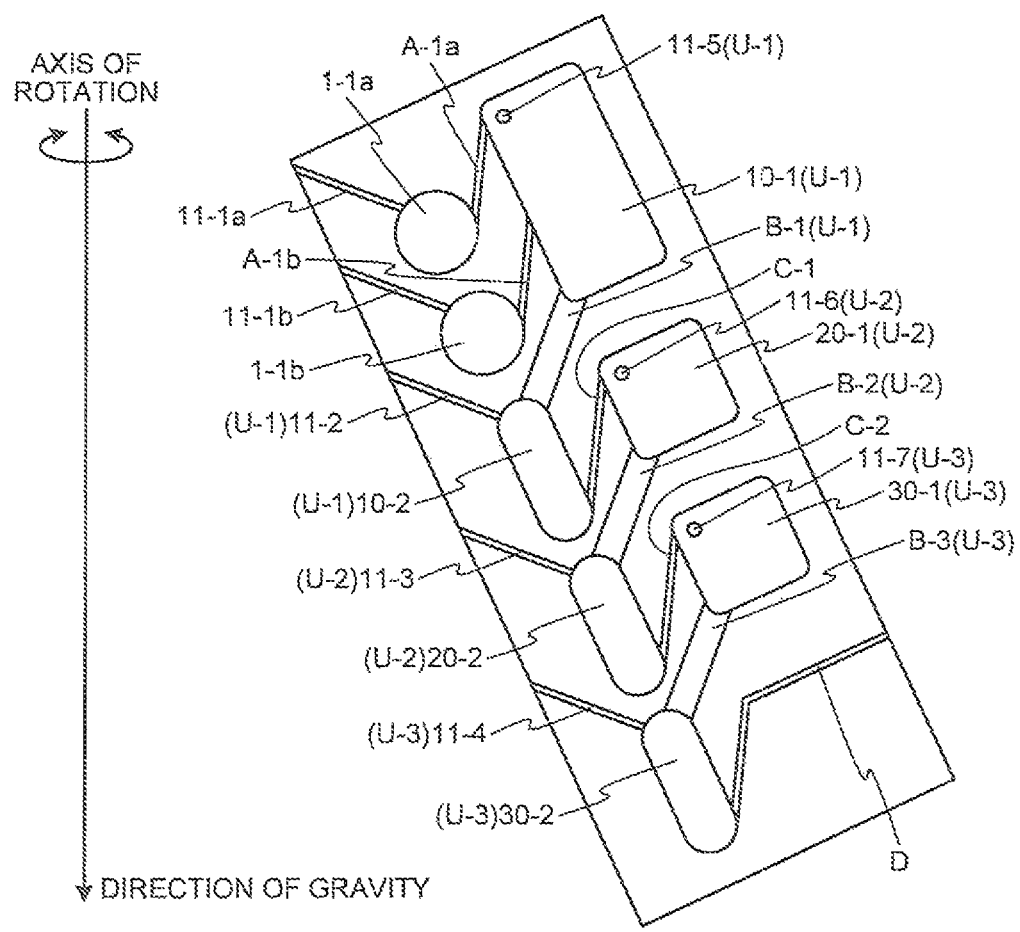
FIG. 2 is a plan view illustrating another example of a liquid-feeding chip according to the present invention.

The liquid-feeding chip according to the present invention is used by rotating it around an axis of rotation which is located external to the liquid-feeding chip. In the present invention, the term "rotate" means to revolve around a circumference with respect to a given axis of rotation. Here, the term "rotate" may also be referred to as "revolve," as distinguished from "spin." The orbit of rotation may be approximately circular. The orbital radius is not specifically limited. The direction of the liquid-feeding chip during rotation is, usually, configured such that the liquid-feeding chip is mounted on a rotation apparatus so that the main surface of the liquid-feeding chip (surface on the side from which the respective storage tanks and channels can be observed when the liquid-feeding chip is viewed transparently) is disposed along a plane including the axis of rotation and is allowed to rotate toward the circumferential direction of the orbit of rotation. In particular, for a liquid-feeding chip having a quadrangular main surface, it is preferred to rotate the liquid-feeding chip in an inclined state so that the corner of the liquid-feeding chip which is closest to a second holding tank of a lowest level liquid-feeding unit is a bottom portion. For example, the main surface is rotated toward the circumferential direction of the orbit of rotation in a state in which the main surface is inclined (state in which the upper corner portion of the liquid-feeding chip near the axis of rotation is inclined about the lower corner portion thereof near the axis of rotation) so that a second holding tank 30-2 of a third level liquid-feeding unit U-3 is positioned at the very bottom as illustrated in FIG. 2. More specifically, the liquid-feeding chip may be used by mounting on an angle rotor. The liquid-feeding chip may be positioned so that an edge of the main surface on the axis of rotation side is inclined by 10 to 80°, and preferably 20 to 50°, with respect to the axis of rotation.

Assuming that the liquid-feeding chip according to the present invention is used by mounting onto an angle rotor, the extension direction (extension angle) of the channels, the shape of the storage and holding tanks and such features are designed by considering the incline of the liquid-feeding chip when it is mounted on the angle rotor.

In the following description, if the liquid-feeding chip is mounted on a rotation apparatus, specifically, if the liquid-feeding chip is mounted on an angle rotor, the shape and the state of the liquid-feeding chip, and especially the angle, may be described based on the assumption that the liquid-feeding chip is mounted on an angle rotor and is in an inclined state.

Figure 26:
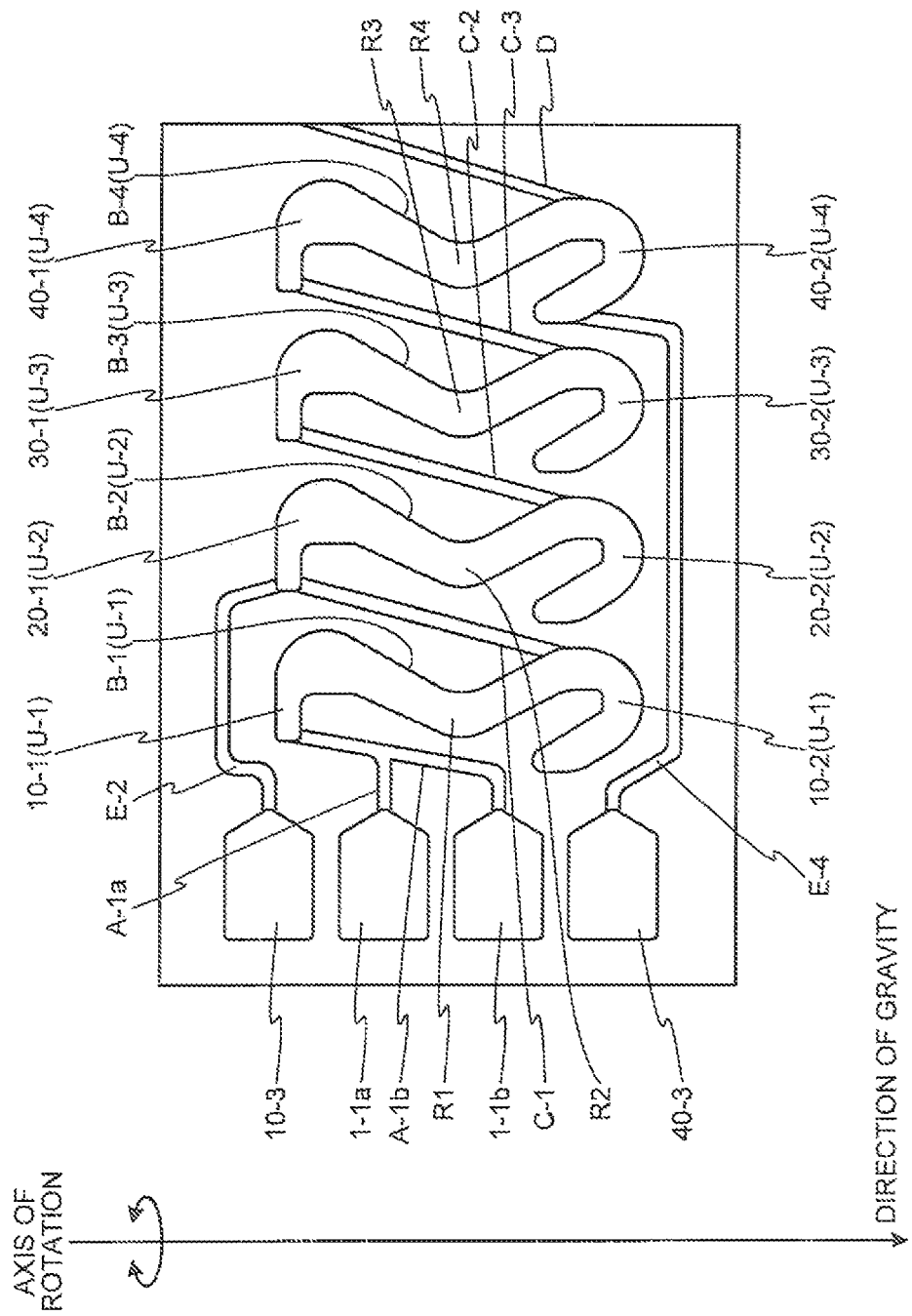
FIG. 26 is a plan view illustrating another example of the liquid-feeding chip according to the present invention.
Figure 27:
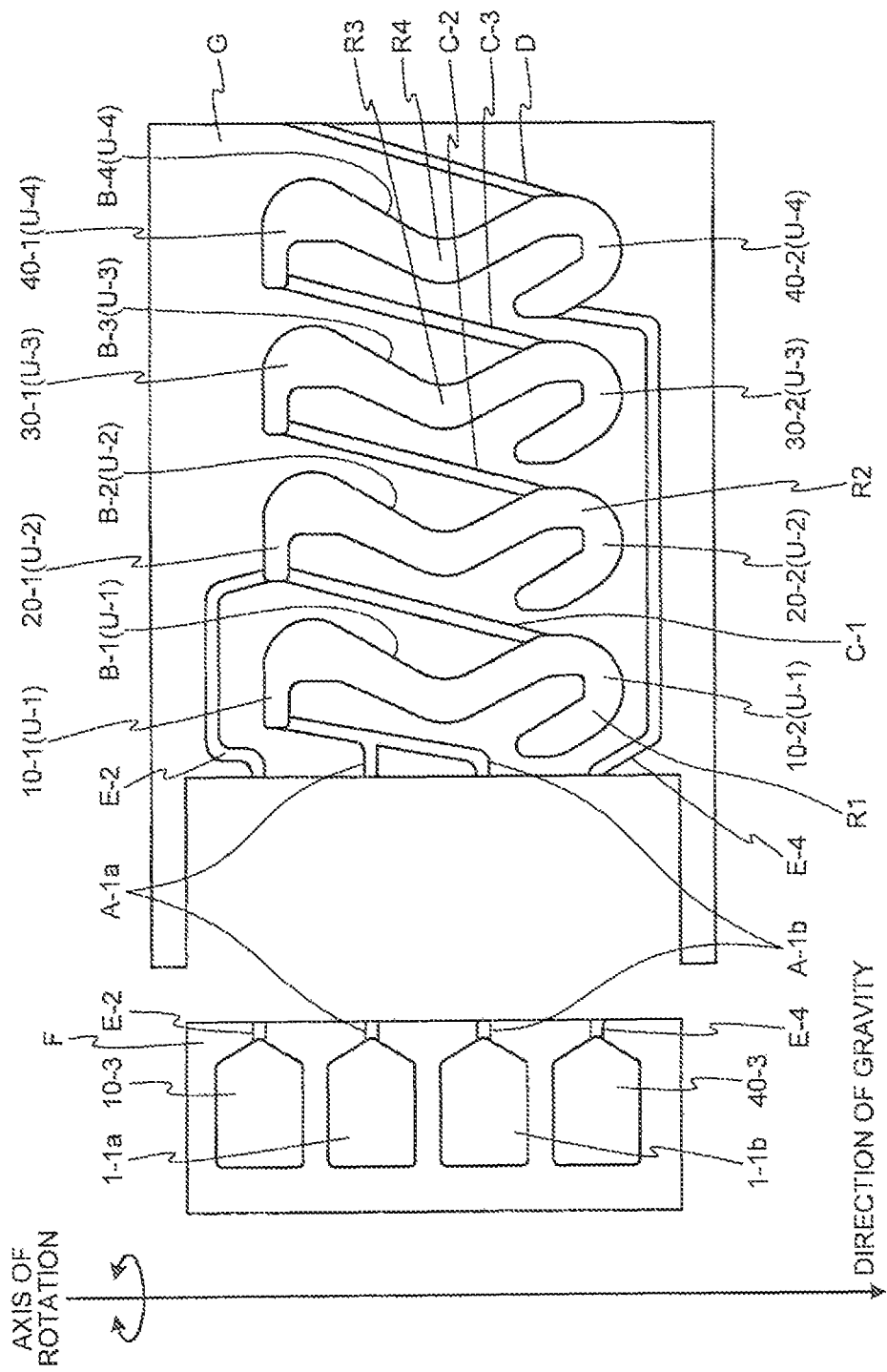
FIG. 27 is a plan view illustrating another example of the liquid-feeding chip according to the present invention.

For the liquid-feeding chips illustrated in FIGS. 26 and 27, a plurality of liquid-feeding units are arranged in parallel in an approximately horizontal direction. These liquid-feeding chips do not have to be inclined when mounted on the rotation apparatus. The edge of the main surface on the axis of rotation side is parallel to the axis of rotation.

The liquid-feeding chip according to the present invention usually has a thin sheet-like cuboid or rectangular solid shape.

The liquid-feeding chip according to the present invention may have a size which can be mounted on the rotation apparatus (centrifuge).

It is preferred to use the liquid-feeding chip according to the present invention mounted on a rotor. As the rotor, as described above, it is more preferred to use an angle rotor. In such a case, the channel angles are controlled so as to match the angle of the angle rotor. Furthermore, as the rotor used for the liquid-feeding chips illustrated in FIGS. 26 and 27, a rotor which can rotate a liquid-feeding chip having a thickness which allows a liquid to be fed utilizing gravity may be used. For example, a cylindrical rotor having a thickness of about several centimeters may be used.

The liquid which is fed by the liquid-feeding chip according to the present invention is not specifically limited. Examples of specimens include biological samples such as liquids extracted from a body, such as blood, urine, spinal liquid, saliva, and phlegm, a cell suspension, a disrupted cell suspension, a nucleic acid solution, a virus suspension, a food extract, and environmental extracts such as a soil extract, or water.

The term "reagent" means a reagent for detecting a specimen. Specific examples thereof include a blocking solution, a diluent, a denaturing agent, a labeled antibody, a labeled antigen, a non-labeled antibody, a non-labeled antigen, a labeling substance, a luminescent substrate, a fluorescent substrate, a chromogenic substrate, a hydrogen peroxide solution, a washing solution, a protein denaturing agent, a cell lysate, an enzyme solution, a labeled nucleic acid, a non-labeled nucleic acid, a primer, a probe, avidin, streptoavidin, a buffer solution, a pH adjusting solution, a hybridization solution, an enzyme reaction terminate solution and the like.

In the present invention, the expression "specimen/reagent" may refer to either a specimen or a reagent, both a specimen and a reagent, as well as a substance including a reaction product of a specimen and a reagent added to either of these. Further, the "specimen/reagent" may be a fluid, and preferably is a liquid. In addition, the expression "specimen/reagent" may be replaced with "specimen and/or reagent."

The liquid-feeding chip according to the present invention is mounted on a rotation apparatus so that the main surface of the chip lies along a plane which includes the axis of rotation. The specimen/reagent is fed from/to the respective storage tanks by varying the rotation speed. Specifically, the liquid is fed by sequentially rotating at a first rotation speed and then at a second rotation speed, which is slower than the first rotation speed, or by stopping rotation. As described above, the liquid feeding according to the liquid-feeding chip of the present invention utilizes centrifugal force and gravity. Therefore, in addition to varying the rotation speed, the radius of the orbit of rotation may also be varied.

The first rotation speed may be appropriately set so that the centrifugal force acting on the liquid-feeding chip is usually 1 to 100,000 G, and preferably 10 to 10,000 G. More preferably, the first rotation speed may be appropriately set so that the centrifugal force is 20 to 5,000 G.

On the other hand, the second rotation speed must be slower than the first rotation speed. A specific range for the second rotation speed is set so that the centrifugal force is usually 0 to 50 G, and preferably 0 to 10 G. The second rotation speed may also be replaced by stopping rotation (centrifugal force of 0 G).

The first and second rotation speeds may each be a specific rotation speed, or may be a rotation speed which is continuously changing within a given specific rotation speed range.

The material of the liquid-feeding chip according to the present invention is not specifically limited. Examples thereof may include a resin, glass and the like. In particular, from the perspective of facilitating external observation of the storage tanks and channels, at least a part of the storage tanks and channels may be transparent or opaque. If transparent, the liquid feeding condition can be easily externally detected. Furthermore, when reacting specimen/reagent solutions which were fed in order by a reaction chamber provided downstream of a channel D and measuring by an optical method, it is preferred to use a transparent material in a part of the reaction chamber. Moreover, the surface of the reaction chamber portion formed from a transparent material may be flat, or may be lens-shaped.

Furthermore, as a material for stably feeding regardless of the type of liquid, a chemically stable material which has chemical resistance and water resistance is preferred.

Specific examples of the material of the liquid-feeding chip include a resin such as poly(methyl methacrylate) (PMMA), polycarbonate, polypropylene, polyethylene, polymethylpentene, polystyrene, polytetrafluoroethylene, ABS resin, polydimethylsiloxane, silicone, and copolymers or complexes including a polymer compound of such a resin; a glass such as quartz glass, Pyrex® glass, soda glass, borate glass, silicate glass, borosilicate glass, and complexes thereof; a metal surface coated with an insulating material and complexes thereof, and a ceramic and complexes thereof Among these, It is especially preferred to use poly(methyl methacrylate) (PMMA), polycarbonate, polystyrene, polytetrafluoroethylene, and polypropylene.

Furthermore, as the chemically stable material which has chemical resistance and water resistance, various organic or inorganic materials may be used. Preferably used examples include a resin such as polypropylene, polyethylene, polymethylpentene, polystyrene, polytetrafluoroethylene, polydimethylsiloxane, silicon, and copolymers or complexes including a polymer compound of such a resin; a glass such as quartz glass, Pyrex® glass, soda glass, borate glass, silicate glass, borosilicate glass, and complexes thereof; and a ceramic and complexes thereof. Among these, It is especially preferred to use polypropylene, polyethylene, polymethylpentene, and polystyrene.

The method for forming the liquid-feeding chip according to the present invention is not specifically limited. For example, a substrate having the concave portions of the respective storage tanks and the respective channels formed thereon may be joined to another substrate or a film. Alternatively, the liquid-feeding chip may be formed by sandwiching a substrate having channel-forming slits on either side with two substrates. If the material is a resin, the concave portions of the respective storage tanks and the respective channels may be formed by a typical molding method which uses a mold. Examples of such methods include injection molding, press molding, blow molding, vacuum molding, hot embossing and the like.

The liquid-feeding chip according to the present invention will now be described with reference to the drawings.

FIGS. 1 to 4 and FIGS. 24 to 27 are schematic diagrams in which internal constituent elements are transparently illustrated so as to be clear, when the liquid-feeding chip of the respective examples of the present invention are viewed from a main surface side. FIGS. 8 to 21 schematically illustrate the configuration of the liquid-feeding chip according to the present invention. Although the axis of rotation is shown in some of the figures and not in others, in all of the figures the main surface of the liquid-feeding chip is represented as having an axis of rotation on the left side as viewed. More specifically, all the figures illustrate a state as viewed from a circumferential direction of the orbit when the axis of rotation in an approximately perpendicular direction is positioned on the left side of the liquid-feeding chip during rotation of the liquid-feeding chip. The left side of the liquid-feeding chip is the axis of rotation direction (inner circumferential side). The right side is the outer circumferential side, and is also the centrifugal force direction. Furthermore, the downward direction is the direction of gravity.

As illustrated in FIG. 1, the liquid-feeding chip according to the present invention has a first storage tank, a first holding tank, a channel A, a second holding tank, a channel B, and a channel C. The first holding tank, the second holding tank, and the channel B constitute a liquid-feeding unit. Two or more of these liquid-feeding units are connected by the channel C. More specifically, the liquid-feeding chip according to the present invention contain, as constituent elements, a first storage tank, a first holding tank positioned on an outer circumferential side of the first storage tank, a second holding tank positioned in the direction of gravity with respect to the first holding tank, and a channel A which connects the first storage tank to the first holding tank.

Figures 1, 8:
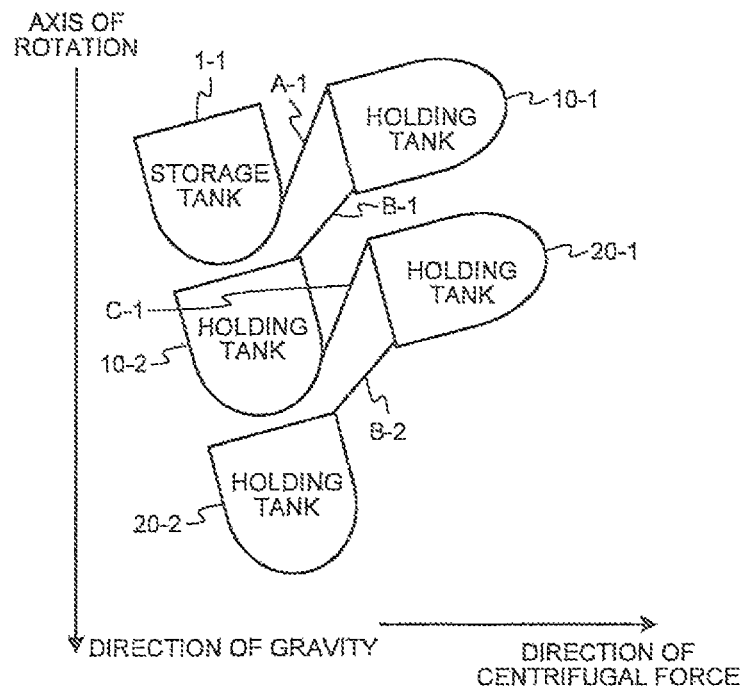
Figures 2, 8:
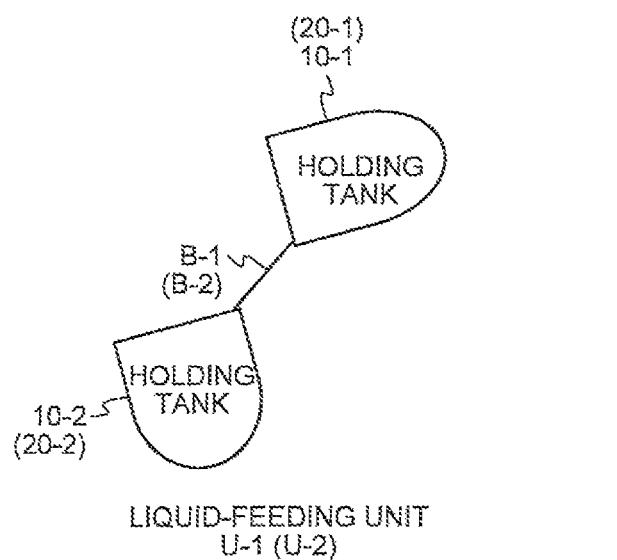

As illustrated in FIG. 8-1, the liquid-feeding chip according to the present invention contain a first storage tank 1-1 and a first holding tank 10-1 aligned in parallel in a centrifugal force direction. On a lower level therefrom (lower level in the direction of gravity with respect to the axis of rotation), a second holding tank 10-2 and a first holding tank 20-1 of the next liquid-feeding unit are aligned in parallel in a centrifugal force direction. On an even lower level, a second holding tank 20-2 is arranged. The first storage tank 1-1 and the first holding tank 10-1 are connected by a channel A-1. The first holding tank 10-1 and the second holding tank 10-2 are connected by a channel B-1. The second holding tank 10-2 and the first holding tank 20-1 of the next liquid-feeding unit are connected by a channel C-1. The first holding tank 20-1 and the second holding tank 20-2 are connected by a channel B-2.

As illustrated in FIG. 8-2, the first holding tank 10-1, the second holding tank 10-2, and the channel B-1 constitute a liquid-feeding unit U-1, and the first holding tank 20-1, the second holding tank 20-2, and the channel B-2 constitute a liquid-feeding unit U-2.

The positional relationship between the first storage tank and the second holding tank is preferably such that these tanks are aligned in parallel along an approximately straight line when the main surface of the liquid-feeding chip is viewed from the front in a state in which the liquid-feeding chip is mounted on the rotation apparatus. Furthermore, it is preferred that the first holding tanks in the respective levels of the liquid-feeding units be also aligned along an approximately straight line. In addition, it is preferred that the second holding tanks in the respective levels of the liquid-feeding units be also aligned along an approximately straight line. This allows the respective storage and holding tanks to be arranged in a small space, and the size of the liquid-feeding chip to be reduced even further.

The term "lower level liquid-feeding unit" in the present invention means a liquid-feeding unit which is positioned downstream of a given liquid-feeding unit when the main surface of the liquid-feeding chip is viewed from the front. A lower level liquid-feeding unit is positioned, with respect to an upper level liquid-feeding unit, in the direction of gravity or an outer circumferential direction with respect to the axis of rotation. Liquid-feeding units on a lower level from the highest level may also be referred to as "second level liquid-feeding unit" and "third level liquid-feeding unit".

Figure 25:
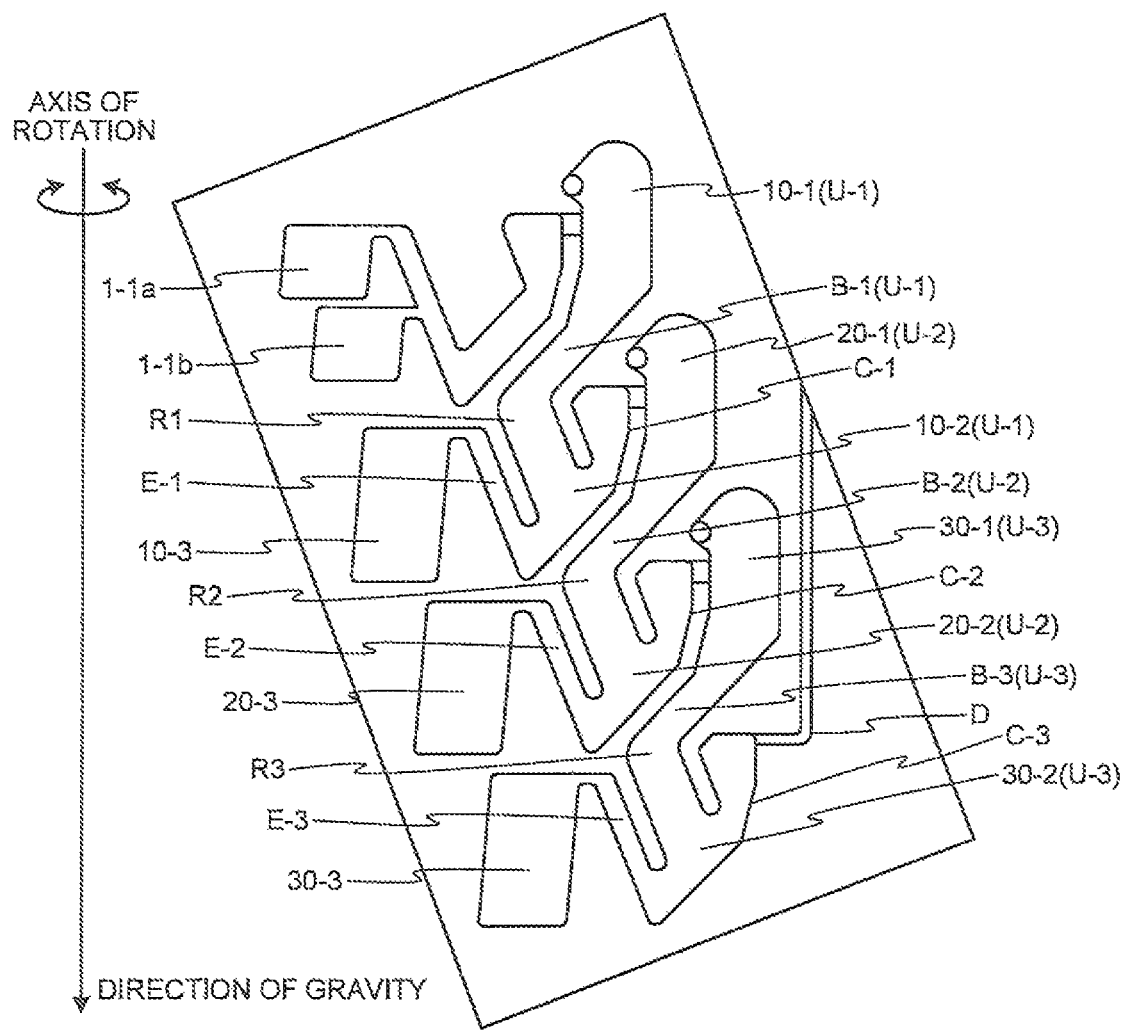
FIG. 25 is a plan view illustrating another example of the liquid-feeding chip according to the present invention.

For the liquid-feeding chip illustrated in FIG. 25, three liquid-feeding units, including a first level liquid-feeding unit U-1, a second level liquid-feeding unit U-2, and a third level liquid-feeding unit U-3, are aligned in parallel in a vertical direction (direction of gravity).

For the liquid-feeding chips illustrated in FIGS. 26 and 27, the first level liquid-feeding unit U-1, the second level liquid-feeding unit U-2, the third level liquid-feeding unit U-3, and a fourth level liquid-feeding unit U-4 are arranged in order in parallel in an outer circumferential direction with respect to the axis of rotation, namely, in an approximately horizontal direction.

The terms "storage tank" and "holding tank" in the present invention mean a tank which can store or hold a liquid in its interior when rotation is stopped or during rotation. A storage tank is a tank which stores a liquid that was directly introduced. A holding tank is a tank which holds a liquid that was fed from another storage tank or holding tank. The storage tanks and holding tanks may contain a liquid in advance, or may contain a powder-like or gel-like reagent in advance which is dissolved by a liquid flowing in from another tank. The storage tanks and holding tanks in the present invention preferably have a capacity of about 1.1 to 10 times the volume of the liquid which is to be contained therein. It is more preferred to use storage tanks and holding tanks having a capacity of about 1.3 to 5 times the volume of the liquid which is to be contained therein.

(First Storage Tank)

When viewed from the main surface side of the liquid-feeding chip, the first storage tank in the present invention is a tank positioned closer to the axis of rotation (inner circumferential side) of the liquid-feeding chip than the first level first holding tank. Since the specimen/reagent is normally contained in advance in the first storage tank before rotation, the first storage tank may have an aperture which allows the specimen/reagent to be injected therein. The capacity of the first storage tank is not specifically limited, as long as the tank can contain the specimen/reagent. However, a storage tank which can contain 0.001 mL to 10 mL, and within that, 0.01 mL to 1 mL, of a liquid is preferred. Furthermore, the shape of the first storage tank is not specifically limited. The shape may be appropriately selected from among shapes such as a rough sphere, cylinder, rectangular solid, pyramid, cone and the like.

(First Holding Tank)

The liquid-feeding chip according to the present invention contains, as a tank constituting a liquid-feeding unit, a first holding tank. The first holding tank is a liquid holding tank positioned on the outer circumferential side of the first storage tank and/or a second holding tank of the previous level liquid-feeding unit with respect to the axis of rotation of the liquid-feeding chip.

The first holding tank holds in its interior, during rotation at a first rotation speed, a specimen/reagent which was fed via the channel A from the first storage tank and/or a specimen/reagent fed via the channel C from a second holding tank of the previous level liquid-feeding unit by the action of centrifugal force and gravity at the first rotation speed. Furthermore, the first holding tank discharges the liquid held in its interior to the second holding tank via the channel B during rotation, which is performed next to the rotation at the first rotation speed, at a second rotation speed, which is slower than the first rotation speed, or when rotation is stopped.

A solid or powder-like reagent for reacting with the fed specimen/reagent may be contained in the first holding tank in advance prior to liquid being fed from the first storage tank. The capacity of the first holding tank is not specifically limited, as long as the tank is capable of holding the specimen/ reagent at the first rotation speed. However, it is preferred that the first holding tank can hold 0.001 to 10 mL, and within that, 0.01 to 1 mL, of liquid.

In the liquid-feeding chip according to the present invention, the first holding tank is connected to two or more first storage tanks in some cases. However, specifically in such a case, it is preferred that the first holding tank have a larger capacity than the first storage tank. Furthermore, the shape of the first holding tank is not specifically limited. Like the first storage tank, the shape may be appropriately selected from among shapes such as a sphere, cylinder, rectangular solid, prismatic column, cone and the like.

(Channel A)

In the present invention, the channel A is one of the channels constituting the liquid-feeding unit, and is the channel which connects the first storage tank to the first holding tank. The channel A is a channel for feeding a liquid from the first storage tank to the first holding tank by the action of centrifugal force and gravity during the rotation of the liquid-feeding chip at the first rotation speed (mainly by the action of centrifugal force).

For example, as illustrated in FIG. 1, one end of the channel A is connected so as to open up a lower portion of the first storage tank on the outer circumferential side, and the other end is connected so as to open up an upper portion of the first holding tank on the axis of rotation side.

The shape and the size of the channel A are not specifically limited, as long as the overall channel has a tube shape. The whole channel A does not have to have the same shape. Furthermore, the channel A may be an aperture which directly connects the first storage tank to the first holding tank. The shape of the cross section orthogonal to the channel A extension direction (transverse cross-section) is not specifically limited to a circle, a polygon or the like. The size of the transverse cross-section also does not have to be fixed, and may be appropriately adjusted to a size through which the specimen/reagent can pass. For example, the short diameter (for a circle, this means the radius, and for a polygon, this means the shortest diameter passing through the center) is usually in the range of 10 μm to 5 mm, and preferably in the range of 100 μm to 1 mm. If the short diameter of the channel A is less than this range, the time required to feed the liquid from the first storage tank to the first holding tank at the first rotation speed becomes longer due to pressure loss. If the short diameter is more than this range, the required time becomes shorter.

Furthermore, as long as the channel A connects the first storage tank to the first holding tank, the channel A does not have to be completely straight. Part of the channel A may be curved or have an irregular shape. The channel A may be formed from a mix of straight lines and curves, and may even have an inflection midway along.

It is preferred that the channel A be positioned further toward the outer circumferential side than the plane which passes through a connecting portion of the channel A and the first storage tank and which is perpendicular to the combined force of the centrifugal force and gravity at the first rotation speed. This allows a liquid which has been introduced into the first storage tank to be fed from the first storage tank to the first holding tank of the highest level liquid-feeding unit when rotating the liquid-feeding chip at the first rotation speed.

The expression "plane which passes through a connecting portion of the channel A and the first storage tank and which is perpendicular to the combined force of the centrifugal force and gravity at the first rotation speed" means the plane which forms an angle perpendicular to the combined force of the centrifugal force and gravity acting on the connecting portion of the channel A and the first storage tank of the liquid-feeding chip when rotating the liquid-feeding chip at the first rotation speed, and which intersects that connecting portion. The expression "positioned further toward the outer circumferential side than the plane which passes through a connecting portion of the channel A and the first storage tank and which is perpendicular to the combined force of the centrifugal force and gravity at the first rotation speed" means that, of the two spaces separated by the above-described perpendicularly positioned plane, it is positioned in the space on the outer circumferential side as viewed from the axis of rotation. In other words, of the two spaces, this means that the channel A is positioned in the space in which the axis of rotation is not located.

For example, if the direction and magnitude of the centrifugal force acting on the liquid-feeding chip and of gravity are indicated by the arrows as illustrated in FIG. 9, the combined force of the centrifugal force and gravity is represented by the direction and the magnitude indicated by the thick arrow extending in the outer circumferential direction. The expression "plane perpendicular to the combined force of the centrifugal force and gravity" is the plane through which the thick arrow indicating the perpendicular direction to the arrow of this combined force passes. Therefore, the expression "positioned further toward the outer circumferential side than the plane which passes through a connecting portion of the channel A and the first storage tank and which is perpendicular to the combined force of the centrifugal force and gravity at the first rotation speed" means that the channel A is positioned in the space (outer circumferential side) of the side opposite to the space (inner circumferential side) in which the axis of rotation is located with respect to the plane through which the thick arrow indicating the plane perpendicular to the combined force passes.

It is preferred that at least a part of the channel A be positioned further toward the outer circumferential side than a "plane including a liquid surface of the specimen/reagent" in the first storage tank at the first rotation speed. This allows the liquid to be more reliably fed from the first storage tank when rotating the liquid-feeding chip at the first rotation speed, because the liquid which has been introduced into the first storage tank continuously flows from the first storage tank to the first holding tank. It is not necessary for all of the channel A to be positioned further toward the outer circumferential side than the "plane including a liquid surface of the liquid" in the first storage tank at the first rotation speed. It is only necessary for the wall on the outer circumferential side of the channel A to be positioned further toward the outer circumferential side than the "plane including a liquid surface of the liquid".

The expression "plane including a liquid surface of the specimen/reagent in the first storage tank at the first rotation speed" means a plane including a liquid surface formed by the liquid in the first storage tank when the liquid-feeding chip containing the first storage tank into which the liquid has been introduced is rotated at the first rotation speed.

Furthermore, in the present invention, the expression "plane including a liquid surface" means, when the liquid surface is flat, the liquid surface. However, the liquid surface is not always flat, due to menisuces of the left and right wall faces formed by the surface tension with the wall face due to the tanks being a thin tube shape coming together. Thus, when the liquid surface is not flat, the expression "plane including a liquid surface" means the plane extending in a tangential direction to the liquid surface in the center of the tank.

The movement process of the liquid from the first storage tank when the liquid-feeding chip is rotated at the first rotation speed is as follows. First, the "plane including a liquid surface of the liquid" in the first storage tank when the liquid-feeding chip according to the present invention begins to be rotated inclines with respect to the horizontal plane (horizontal direction). Before reaching the first rotation speed, namely, when the channel A is further toward the outer circumferential side than the "plane including a liquid surface of the liquid" in the first storage tank, the liquid begins to flow from the first storage tank into the first holding tank due to the action of centrifugal force and gravity. Subsequently, while the "plane including a liquid surface of the liquid" in the first storage tank is still positioned further toward the inner circumferential than at least a part of the channel A, the liquid continues to flow from the first storage tank to the first holding tank.

Therefore, when at least a part of the channel A of the liquid-feeding chip according to the present invention is positioned further toward the outer circumferential side than the "plane including a liquid surface of the specimen/reagent" in the first storage tank during rotation at the first rotation speed, all of the liquid in the first storage tank can be moved to the first holding tank via the channel A.

Figure 10:
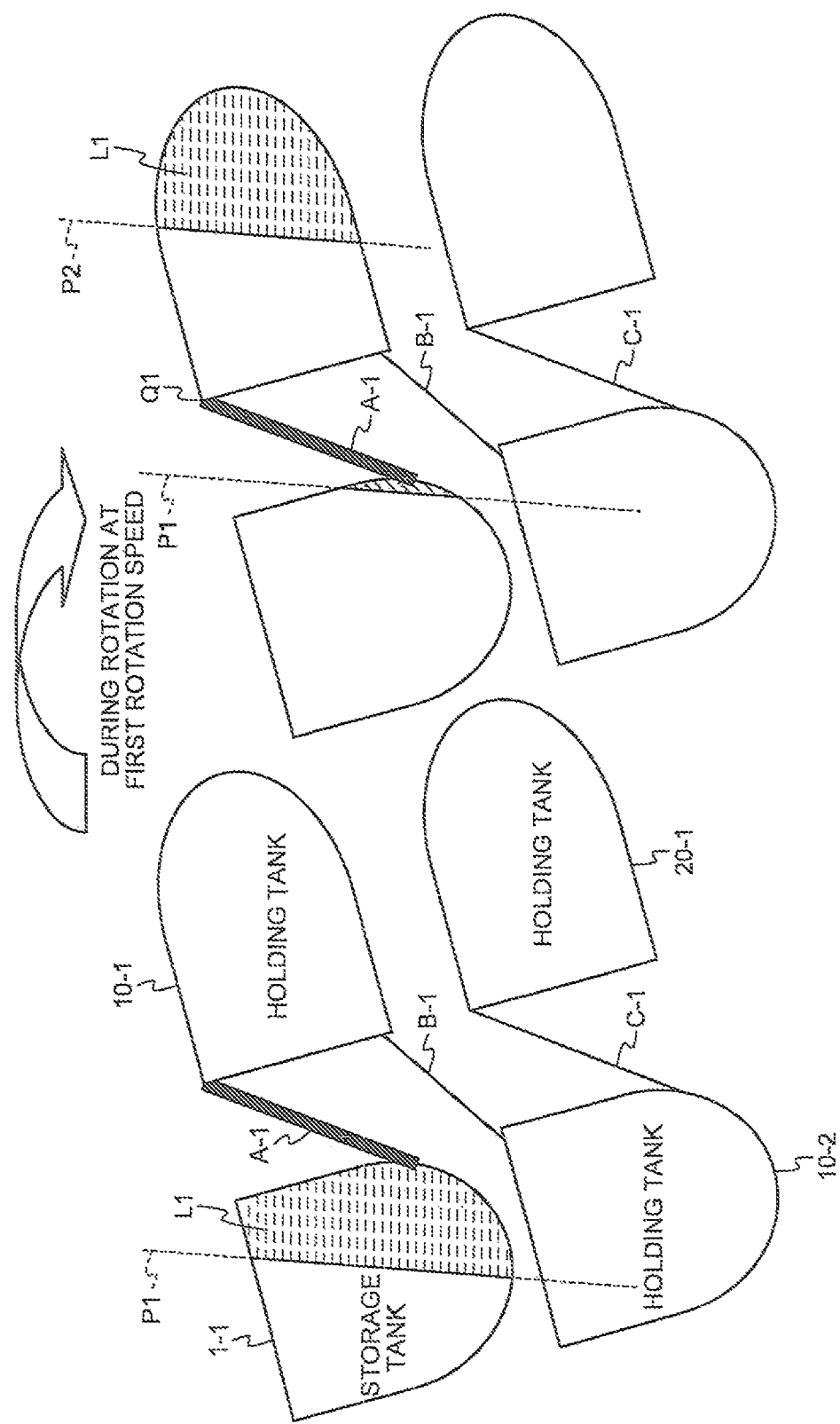
FIG. 10 is an explanatory diagram illustrating a preferred position of a channel A in the liquid-feeding chip according to the present invention with respect to a liquid surface in a first storage tank.

For example, as illustrated in FIG. 10, when the liquid-feeding chip is rotated at the first rotation speed, a plane P1 including a liquid surface of a liquid L1 in the first storage tank 1-1 traces a line which slants upward to the right as viewed from the main surface side of the liquid-feeding chip. However, when the channel A-1 is positioned further toward the outer circumferential side than the liquid surface P1 (of the two spaces separated by P1, the space on the opposite side to the space in which the axis of rotation is located), the liquid can flow out until the first storage tank 1-1 is empty.

Figure 20:
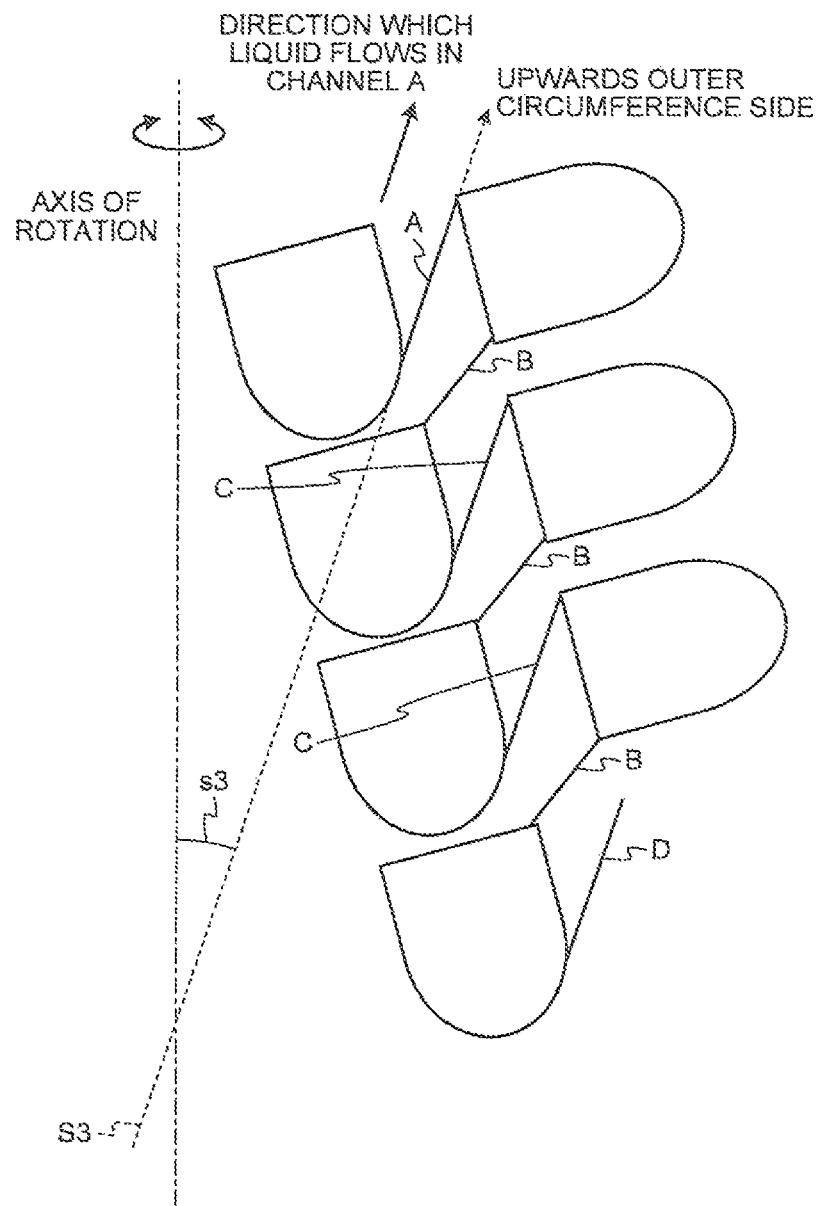
FIG. 20 is an explanatory diagram illustrating a preferred angle of the channel A in the liquid-feeding chip according to the present invention with respect to the axis of rotation.

Such a channel A preferably has a shape in which at least a part thereof forms an angle in an upwards outer circumferential direction with respect to the axis of rotation. That angle can be appropriately set between usually 0 to 80°, preferably 1 to 45°, and more preferably 3 to 15°. The angle is preferably smaller, as this allows the distance between the first storage tank and the first holding tank to be reduced, and the tanks to be arranged without any wasted space. For example, as illustrated in FIG. 20, an angle formed between a channel A and the axis of rotation means an angle s3 that is formed between a channel A extension line (extension line in the direction which the liquid flows in the channel A) S3 and the axis of rotation. If the channel A is inflected, the angle formed between the axis of rotation and the channel A can be defined as the angle formed between the axis of rotation and the extension line extending along the line connecting the connecting portion of the first storage tank and the channel A and the point positioned at the highest point along the channel A.

Furthermore, even if all of the channel A is not positioned further toward the outer circumferential side than the "plane including a liquid surface of the specimen/reagent" in the first storage tank at the first rotation speed, it is preferred that the connecting portion of the channel A and the first storage tank be positioned further toward the outer circumferential side with respect to the axis of rotation than the "plane including a liquid surface" in the first storage tank at the first rotation speed. This allows the liquid in the first storage tank to be reliably fed to the first holding tank during rotation at the first rotation speed.

Furthermore, it is preferred that at least a part of a connecting portion of the channel A and the first holding tank be located closer to the axis of rotation (inner circumferential side) than the plane including a liquid surface of the specimen/reagent in the first holding tank at the first rotation speed. When the liquid-feeding chip is rotated at the first rotation speed, the liquid fed from the first storage tank forms a liquid surface which is approximately perpendicular to the combined force of the centrifugal force and gravity at the first holding tank. At this point, since at least a part of the connecting portion of the channel A and the first holding tank is allowed to be positioned closer to the axis of rotation than this plane including the liquid surface, the liquid can be reliably held by the first holding tank during rotation at the first rotation speed. Furthermore, this also allows back flow to the first storage tank to be more effectively prevented.

The flow process of the liquid in the first holding tank when the liquid-feeding chip is rotated at the first rotation speed is as follows. First, when the liquid-feeding chip according to the present invention is rotated at the first rotation speed, the liquid begins to flow into the first holding tank due to the action of centrifugal force and gravity. Subsequently, while the "plane including a liquid surface of the liquid" in the first holding tank is still positioned further toward the outer circumferential side than the connecting portion of the channel A and the first holding tank, the liquid continues to flow in without flowing back out of the first holding tank.

Therefore, when at least a part of the connecting portion of the channel A and the first holding tank of the liquid-feeding chip according to the present invention is positioned further toward the inner circumferential than the plane including a liquid surface of the liquid in the first holding tank at the first rotation speed, the liquid is held in the first holding tank without flowing back out of the first holding tank.

As illustrated in FIG. 10, when the liquid-feeding chip is rotated at the first rotation speed, a plane P2 including a liquid surface of the liquid L1 in the first holding tank 10-1 traces a line which slants upward to the right as viewed from the main surface of the liquid-feeding chip. However, since a connecting portion Q1 of the channel A-1 and the first holding tank is positioned further toward the left side than the plane P2 (of the two spaces separated by P2, the space in which the axis of rotation is located), the liquid can be held in the first holding tank 10-1 without flowing back out into another tank. The connecting portion Q1 of the first holding tank and the channel A-1 is preferably positioned higher than the first holding tank. Consequently, during rotation at a second rotation speed, which is slower than the first rotation speed, or when rotation is stopped, the connecting portion Q1 is positioned higher than the plane including a liquid surface which is formed in the first holding tank. This allows back flow into the first storage tank to be effectively suppressed.

(Second Holding Tank)

The liquid-feeding chip according to the present invention contains, as a tank constituting a liquid-feeding unit, a second holding tank. This second holding tank is a tank positioned in the direction of gravity with respect to the first holding tank with respect to the axis of rotation of the liquid-feeding chip. Preferably, the second holding tank is positioned closer to the axis of rotation (inner circumferential side) of the liquid-feeding chip than the first holding tank.

The term "direction of gravity" in the present invention means the direction in which the liquid flows due to the action of gravity. Specifically, this term means downward from the horizontal. The expression "the second holding tank is positioned in the direction of gravity with respect to the first holding tank" means that the second holding tank is lower than the first holding tank. Specifically, this expression means that the second holding tank is positioned downward from the horizontal when the main surface of the liquid-feeding chip is viewed during rotation of the liquid-feeding chip. In other words, the term "direction of gravity" may be a direction having a vector in the direction of gravity. Obviously, a direction close to the vertical direction is preferred in order to facilitate the flow of liquid by the action of gravity.

The second holding tank is a tank capable of holding the liquid in its interior when rotation of the liquid-feeding chip according to the present invention is stopped, or the liquid-feeding chip is rotated at the second rotation speed. The liquid in such a case, specifically, the specimen/reagent, may have been fed from the first storage tank or may have been directly contained in the second holding tank.

The capacity of the second holding tank is not specifically limited, as long as the tank is capable of holding the specimen/reagent. However, it is preferred that the second holding tank can hold 0.001 to 10 mL, and within that, 0.01 to 1 mL, of the liquid. Furthermore, the shape of the second holding tank may be appropriately selected from among shapes such as a rough sphere, rectangular solid, pyramid, cone and the like. The second holding tank may be configured so that a liquid temporarily held in the second holding tank can be discharged through the channel C or D at the first rotation speed.

(Channel B)

In the present invention, the channel B is one of the channels constituting the liquid-feeding unit, and is the channel which connects the first holding tank to the second holding tank. During rotation at a second rotation speed which is slower than the first rotation speed of the liquid-feeding chip, or when rotation is stopped, the liquid flows through the channel B due to the action of gravity, and is fed from the first holding tank to the second holding tank. The channel B extends in a direction of gravity from a connecting portion with the first holding tank, and is connected to the second holding tank. Consequently, during rotation at a second rotation speed which is slower than the first rotation speed of the liquid-feeding chip, or when rotation is stopped, the liquid can be fed from the first holding tank to the second holding tank due to the action of gravity.

For example, as illustrated in FIG. 1, one end of the channel B is connected so as to open up an upper portion of the second holding tank on the outer circumferential side, and the other end is connected so as to open up a lower portion of the first holding tank of the same level on the axis of rotation side.

It is preferred that at least a part of the connecting portion of the channel B and the first holding tank be positioned closer to the axis of rotation (inner circumferential side) than the plane including a liquid surface of the specimen/reagent in the first holding tank at the first rotation speed. When the liquid-feeding chip is rotated at the first rotation speed, the liquid fed from the first storage tank forms a liquid surface which is approximately perpendicular to the combined force of the centrifugal force and gravity at the first holding tank. At this point, by positioning at least a part of the connecting portion of the channel B and the first holding tank closer to the axis of rotation than this liquid surface, the liquid can be reliably held by the first holding tank during rotation at the first rotation speed.

Figures 1, 11:
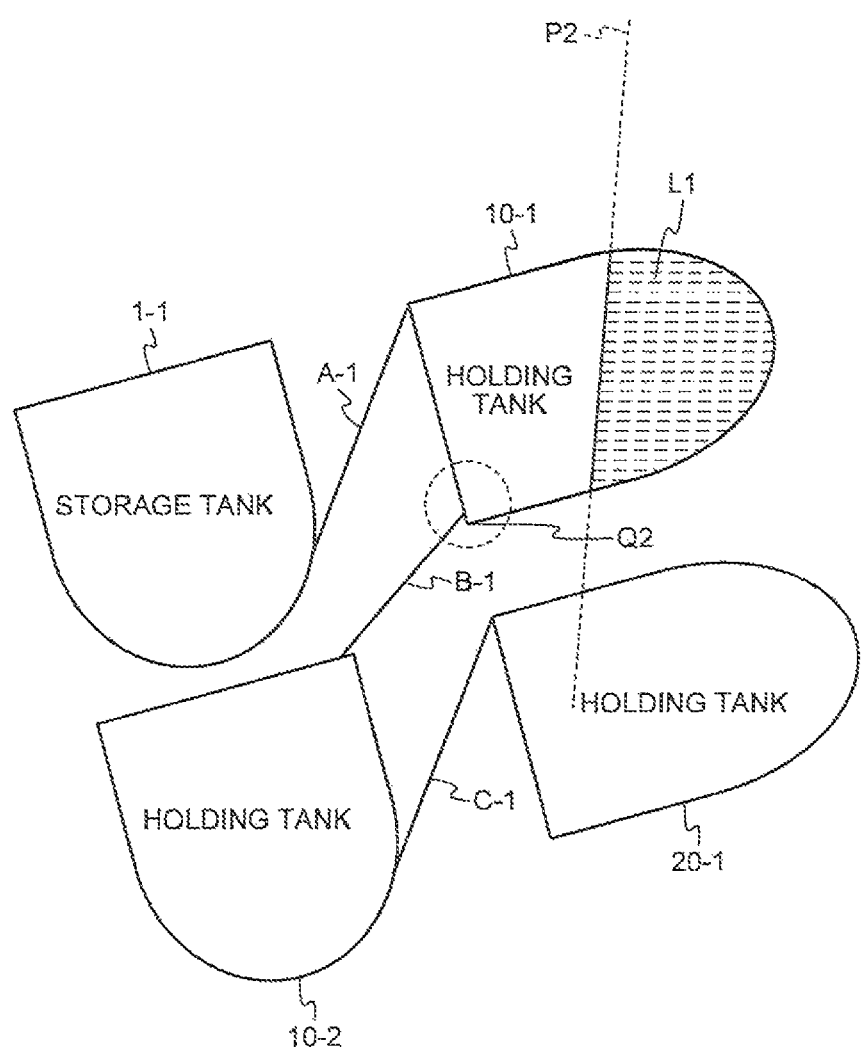
Figures 2, 11:
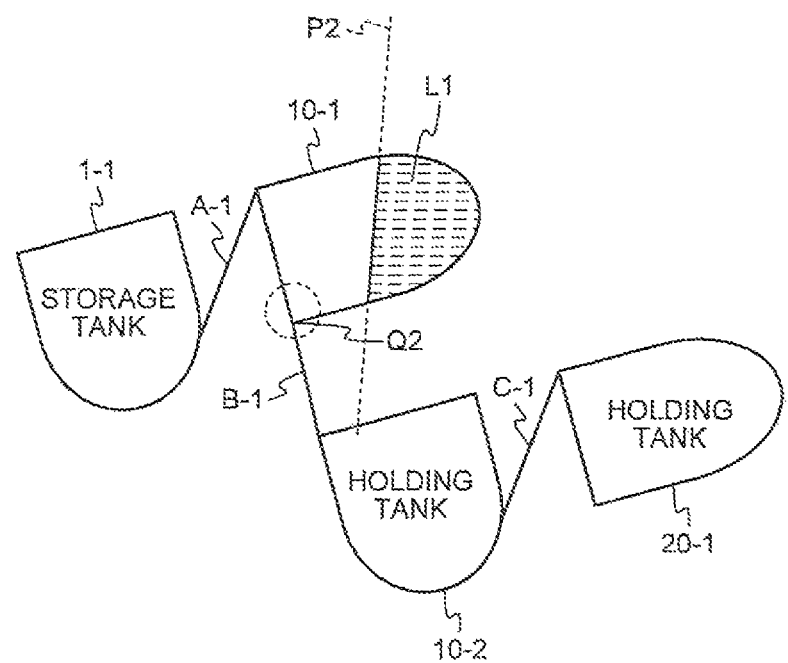

As illustrated in FIG. 11-1, when the liquid-feeding chip is rotated at the first rotation speed, since a connecting portion Q2 of a channel B-1 and the first holding tank 10-1 is positioned further toward the inner circumference (axis of rotation) than the plane P2 including a liquid surface of the liquid L1 in the first holding tank 10-1 (of the two spaces separated by P2, the space in which the axis of rotation is located), the liquid can be held in the first holding tank 10-1 without flowing back out into another tank.

Furthermore, as illustrated in FIG. 11-2, if the connecting portion Q2 is further toward the inner circumferential than the plane P2, the liquid can be held in the first holding tank 10-1 during rotation at the first rotation speed.

The connecting portion Q2 of the first holding tank 10-1 and the channel B-1 is preferably positioned lower than (in the direction of gravity) the first holding tank 10-1. Consequently, during rotation at the second rotation speed, which is slower than the first rotation speed, or when rotation is stopped, the connecting portion Q2 is positioned lower than the plane including the liquid surface which is formed in the first holding tank 10-1. This allows the liquid to be completely discharged from the first holding tank 10-1 via the channel B-1 into the second holding tank 10-2.

It is preferred that the channel B of the present invention be positioned lower than the "plane including a liquid surface of the specimen/reagent" in the first holding tank at the second rotation speed. In this case, the liquid in the first holding tank can be more reliably fed from the first holding tank to the second holding tank during rotation of the liquid-feeding chip at the second rotation speed, or when rotation is stopped.

It is preferred that at least a part of the channel B extend further toward the inner circumferential (direction toward the axis of rotation) than the "plane including a liquid surface of the specimen/reagent" in the first holding tank at the first rotation speed. Consequently, the flow of the liquid in the first holding tank out to the second holding tank during rotation at the first rotation speed can be effectively prevented.

For example, as illustrated in FIGS. 11-1 and 11-2, when the liquid-feeding chip is rotated at the first rotation speed, since the channel B-1 is positioned further toward the inner circumferential than the plane P2 including a liquid surface of the liquid L1 in the first holding tank 10-1 (of the two spaces separated by P2, the space in which the axis of rotation is located), the liquid can be held in the first holding tank 10-1.

It is preferred that the channel B be positioned lower than the "plane including a liquid surface of the specimen/reagent" in the first holding tank at the second rotation speed. This allows the liquid to be effectively fed from the first holding tank to the second holding tank at the second rotation speed without stagnating. The expression "lower than the plane including a liquid surface of the specimen/reagent" means that, as illustrated in FIG. 12, for example, when the liquid-feeding chip is rotated at the second rotation speed or when rotation is stopped, the channel B-1 is positioned in a space (of the two spaces separated by P3, the space disposed in the direction of gravity) which is lower than a plane P3 including a liquid surface of the liquid L1 in the first holding tank 10-1.

If the channel B is a shape which forms an angle with respect to the axis of rotation, this angle may usually be set so that it is 0 to 80°, preferably 0 to 60°, and more preferably 0 to 45° in an inner circumferential direction (direction toward the axis of rotation) or a downwards outer circumferential direction (direction of gravity). In such a case, during rotation at the second rotation speed or when rotation is stopped, the liquid in the first holding tank can be more effectively fed to the second holding tank. More preferably, this angle may be set between 1 to 80° in an inner circumference downwards direction. By extending the channel B in an inner circumferential direction, the second holding tank can be positioned on the inner circumferential side of the liquid-feeding chip, and the space in the liquid-feeding chip can be utilized effectively.

Figure 21:
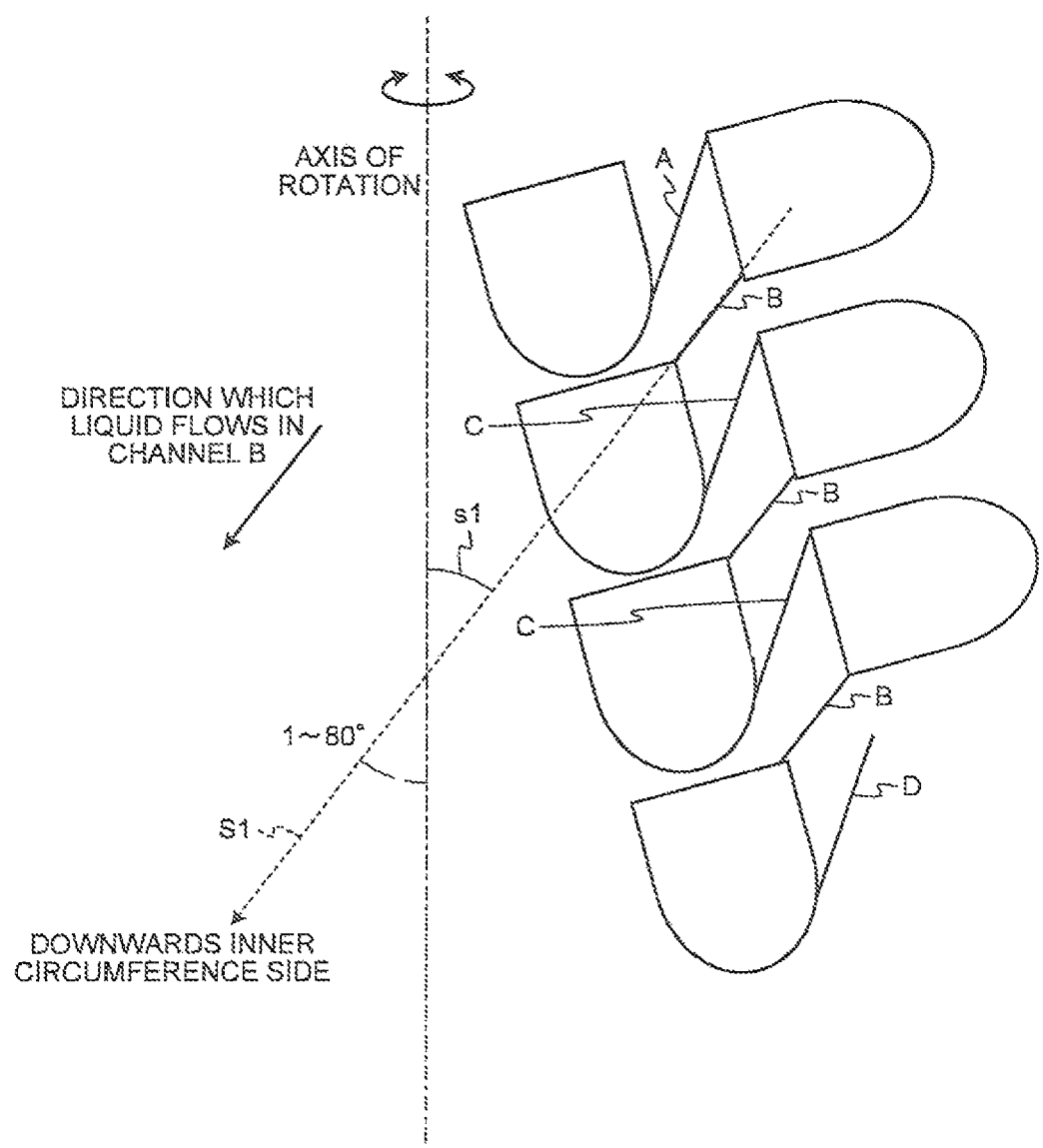
FIG. 21 is an explanatory diagram illustrating a preferred angle of the channel B in the liquid-feeding chip according to the present invention with respect to the axis of rotation.

For example, as illustrated in FIG. 21, the "angle with respect to the axis of rotation of the channel B" is an angle s1 formed by the extension line S1 of the channel B (extension line in the direction in which the liquid flows in the channel B) and the axis of rotation.

Figure 3:
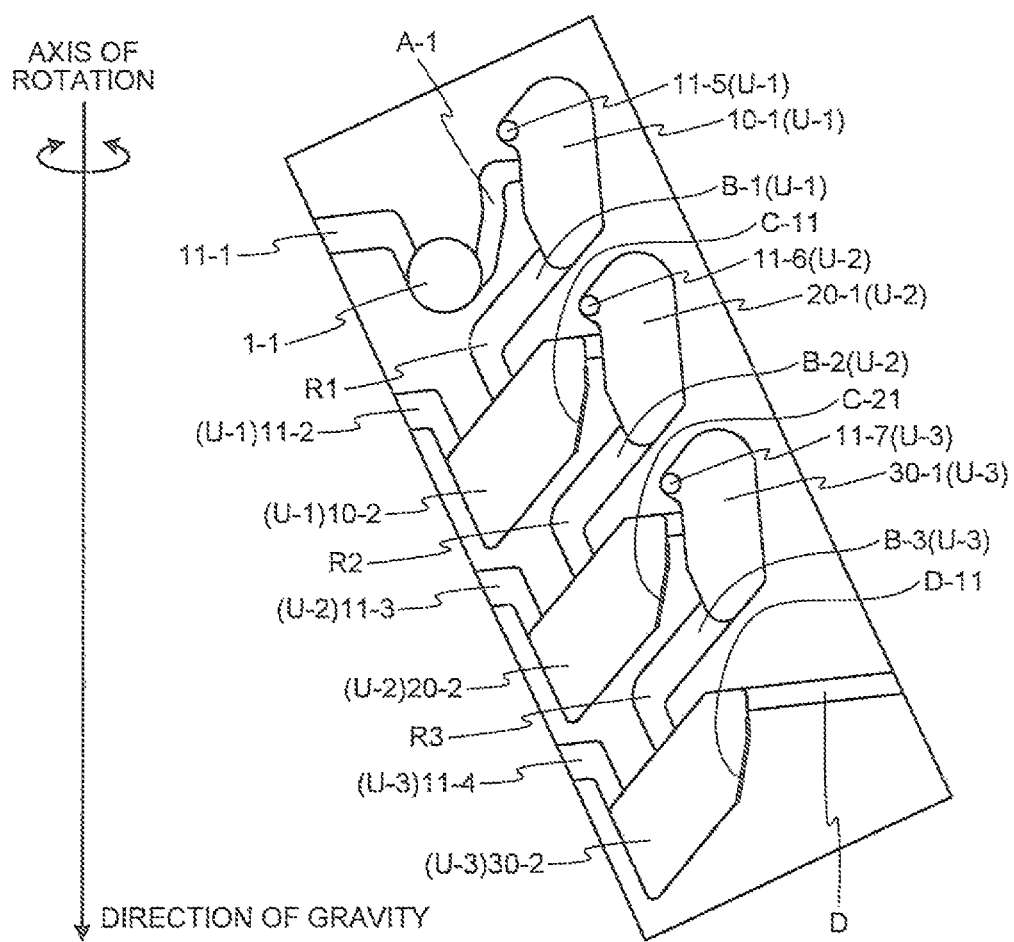
FIG. 3 is a plan view illustrating another example of a liquid-feeding chip according to the present invention.

Furthermore, the channel B may extend toward the lower inner circumferential from the first holding tank, and be inflected toward the lower outer circumferential side from midway along. In such a case, when the liquid passes through the channel B during rotation of the liquid-feeding chip at the second rotation speed, or when rotation is stopped, the liquid can be more reliably fed to the first holding tank of a lower level liquid-feeding unit during the next rotation at the first rotation speed, even if some liquid remains in a bottom portion of the channel B. For example, as illustrated in FIG. 3, which is an example of the configuration of the liquid-feeding chip according to the present invention, the channels B-1, B-2, and B-3 may extend in an axis of rotation and toward the inner circumferential at the connecting portions with the first holding tanks 10-1, 20-1, and 30-1, respectively, and switch to the direction of gravity and outer circumferential direction at the respective positions R1, R2, and R3.

In the liquid-feeding chip illustrated in FIG. 25, the channels B-1, B-2, and B-3 extend in the direction of gravity and toward the inner circumferential from the connecting portions with the corresponding first holding tanks 10-1, 20-1, and 30-1, respectively, bend back to the direction of gravity and toward the outer circumferential side at the respective positions R1, R2, and R3, and are connected to the corresponding second holding tanks 10-2, 20-2, and 30-2. The liquid-feeding chip illustrated in FIG. 25 is configured so that the first holding tank, the channel B, and the second holding tank are continuously and integrally formed. In this example, the first holding tank, the channel B, and the second holding tank of each liquid-feeding unit (U-1, U-2, and U-3) are configured so that a part of the leading edge side continuously widens, and they form an inflected shape approximately like a left-hand angle bracket inflected at the above-described positions R.

Two first storage tanks (1-1a and 1-1b) aligned in parallel in the vertical direction (direction of gravity) are connected to (in communication with) the first holding tank 10-1. The second storage tanks (10-3, 20-3, and 30-3) are connected to the second holding tanks (10-2, 20-2, and 30-2), respectively. From the first storage tanks (1-1a and 1-1b), channels are connected to upper ends of the respective tanks (1-1a and 1-1b) on the outer circumferential side as connecting portions. The channels partially extend in the vertical direction (direction of gravity) when the liquid-feeding chip is viewed in a non-inclined state, then bend back at a midway point in the opposite direction to the outer circumferential direction and the direction of gravity, and are connected to an upper edge of the first holding tank (10-1) on the inner circumferential side. At this point, the channel extending from the first storage tank (1-1a) is connected to the channel extending from the storage tank (1-1b) while extending in the vertical direction (direction of gravity) when the liquid-feeding chip is viewed in a non-inclined state.

From the second storage tanks (10-3, 20-3, and 30-3), channels (E-1, E-2, and E-3) are connected to upper edges of the tanks as connecting portions on the outer circumferential side. The channels partially extend in the vertical direction (direction of gravity) when the liquid-feeding chip is viewed in a non-inclined state, then bend back at a midway point in the opposite direction to the outer circumferential direction and the direction of gravity, and are connected to lower edges of the second holding tanks (10-2, 20-2, and 30-2) on the inner circumferential side. From the second holding tanks (10-2 and 20-2), channels (C-1 and C-2) extend in the opposite direction to the outer circumferential direction and the direction of gravity, and are connected to upper edges of the first holding tanks (20-1 and 30-1) on the inner circumferential side. The channel C-3 extends in the opposite direction to the outer circumferential direction and the direction of gravity, and is connected to the final level second holding tank (30-2). The channel D, which is open to an external side surface of the liquid-feeding chip on the outer circumferential side, partially extends in the outer circumferential direction and the direction of gravity, then bends back at a midway point in the opposite direction to the outer circumferential direction and the direction of gravity, and is connected to an upper edge of the channel C-3 on the outer circumferential side.

In the liquid-feeding chips illustrated in FIGS. 26 and 27, the channels B-1, B-2, B-3, and B-4 extend in the direction of gravity and toward the inner circumferential from the connecting portions with the corresponding first holding tanks 10-1, 20-1, 30-1, and 40-1, bend back toward the direction of gravity and the outer circumferential side at the respective positions R1, R2, R3, and R4, and are connected to the corresponding second holding tanks 10-2, 20-2, 30-2, and 40-2. Specifically, the liquid-feeding chips illustrated in FIGS. 26 and 27 are configured so that the first holding tank, the channel B, and the second holding tank are continuously and integrally formed. In this example, the first holding tank, the channel B, and the second holding tank of each liquid-feeding unit (U-1, U-2, U-3, and U-4) are configured so that they form a reverse Σ shape.

Like the channel A, the shape and the size of the channel B are not specifically limited, as long as the overall channel has a tube shape. The whole channel B does not have to have the same shape. Furthermore, the channel B may be an aperture which directly connects the second holding tank to the first holding tank. The shape of the transverse cross-section is not specifically limited to a circle, a polygon or the like. The size of the transverse cross-section also does not have to be fixed, and may be appropriately adjusted to a size through which the specimen/reagent can pass. However, a size of the transverse cross-section is preferably larger than the channel A, since the liquid in the first holding tank can be smoothly fed to the second holding tank. For example, the short diameter (for a circle, this means the radius, and for a polygon, this means the shortest diameter passing through the center) is usually in the range of 10 μm to 5 mm, and preferably in the range of 100 μ to 3 mm.

It is preferred that the channel B have a section which has a smaller channel cross-sectional area than the channel cross-sectional area at the connecting portion with the first holding tank. In such a case, since the liquid can be fed utilizing capillary action in addition to gravity, the time required to feed the specimen/reagent by gravity can be shortened. More preferably, the channel B has a section having a smaller channel cross-sectional area than the channel cross-sectional area at the connecting portion with the first holding tank, and one or a plurality of sections further downstream having an even smaller channel cross-sectional area. In addition, the channel cross-sectional area along the whole or a part of the channel B may continuously become smaller in the downstream direction.

Furthermore, it is more preferred that the cross-sectional area of the channel B become smaller and smaller closer to the second holding tank. In such a case, the liquid can be more smoothly fed toward the second holding tank during rotation at the second rotation speed or when rotation is stopped due to the action of surface tension when the liquid is fed from the first holding tank to the second holding tank by gravity.

It is preferred that the plurality of channels B in the respective levels of the liquid-feeding units according to the present invention all form the same angle with respect to the axis of rotation. This allows the liquid to be fed to a tank in the direction of gravity during rotation at the same second rotation speed or when rotation is stopped. Furthermore, this also allows liquid feeding to be controlled more easily.

In the present invention, a channel C is connected to the second holding tank. The channel C is the channel which connects the second holding tank to the first holding tank of the above-described lower level liquid-feeding unit. Consequently, an upper level liquid-feeding unit and a lower level liquid-feeding unit are connected by the channel C, so that the liquid can be fed downstream to the next unit. More specifically, as is described below, during rotation at the second rotation speed or when rotation is stopped, the liquid is not fed from the second holding tank through the channel C to the first holding tank of the lower level liquid-feeding unit. Rather, during rotation at the first rotation speed, which is faster than the second rotation speed, the liquid is fed from the second holding tank to the first holding tank of the lower level liquid-feeding unit by the action of centrifugal force and gravity.

The second holding tank in the present invention contains the liquid which flows from the first holding tank. In addition, like the first storage tank, a reagent or specimen may also be contained in the second holding tank in advance before rotation. The second holding tank may also have an aperture so that the reagent or specimen can be injected therein. By containing a liquid in the second holding tank in advance, the liquid contained in advance can be fed to the first holding tank of the lower level liquid-feeding unit via the below-described channel C before the liquid flows in from the first holding tank by rotating at the second rotation speed or by stopping rotation.

(Channel C)

The first holding tank of the lower level liquid-feeding unit according to the present invention is a holding tank positioned on the outer circumferential side of the second holding tank with respect to the axis of rotation of the liquid-feeding chip. This first holding tank can hold in its interior a reagent or a specimen fed via the channel C from the second holding tank by the action of centrifugal force during rotation at the first rotation speed. Furthermore, during rotation at the second rotation speed, which is carried out following the rotation at the first rotation speed and is slower than the first rotation speed, or when rotation is stopped, this first holding tank can discharge the liquid held in its interior. Therefore, excluding the point that the reagent or specimen is fed from the channel C instead of the channel A, this first holding tank is the same as the first holding tank of the highest level liquid-feeding unit. Furthermore, the channel C may be provided as a tank which can hold a specimen/reagent which flows in via a channel E from a below-described second storage tank during rotation at the first rotation speed.

For example, as illustrated in FIG. 1, one end of the channel C is connected so as to open up a lower portion of the second holding tank on the outer circumferential side, and the other end is connected so as to open up an upper portion of the first holding tank one level below on the axis of rotation side.

The channel C according to the present invention is positioned between an upper level liquid-feeding unit and a lower level liquid-feeding unit. The channel C is a channel for feeding a specimen/reagent in the second holding tank of an upper level liquid-feeding unit to the first holding tank of a lower level liquid-feeding unit by the action of centrifugal force and gravity during rotation of the liquid-feeding chip at the first rotation speed. Consequently, a liquid held in the second holding tank of the upper level liquid-feeding unit during rotation at the second rotation speed or when rotation is stopped can be fed to the first holding tank of the lower level liquid-feeding unit during rotation at the first rotation speed. Namely, the liquid can be controlled to sequentially flow based on rotation speed control.

It is preferred that at least a part of the channel C be positioned further toward the inner circumferential of rotation or higher than the "plane including a liquid surface of the specimen/reagent" in the second holding tank during rotation at the second rotation speed or when rotation is stopped. In such a case, during rotation at the second rotation speed or when rotation is stopped, the liquid which has flowed from the first holding tank to the second holding tank can be more reliably held in the second holding tank without flowing into the first holding tank of a lower level liquid-feeding unit.

It is preferred that at least a part of the channel C be positioned in a region positioned higher than the "plane including a liquid surface of the specimen/reagent" in the second holding tank which is formed during rotation at the second rotation speed of the liquid-feeding chip or when rotation is stopped. During rotation at the second rotation speed or when rotation is stopped, although the specimen/reagent flows from the first holding tank to the second holding tank, by configuring in the above manner, liquid in the second holding tank can be more reliably held.

Figure 13:
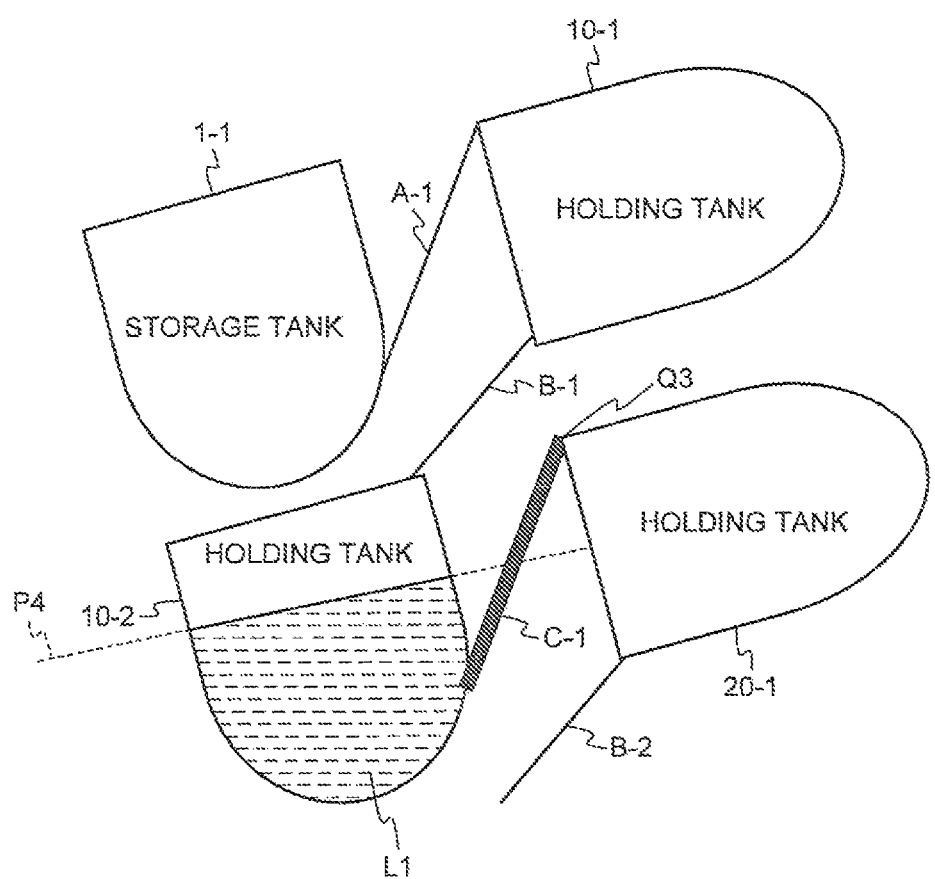
FIG. 13 is an explanatory diagram illustrating a preferred position of a channel C in the liquid-feeding chip according to the present invention with respect to a liquid surface in a second holding tank.

For example, this will be described using FIG. 13 as an example. When the liquid-feeding chip is rotated at the second rotation speed, or when rotation is stopped, a liquid L1 in the second holding tank 10-2 forms a plane P4 including a liquid surface. A part of the channel C-1 has a region positioned in a space which is higher than this plane P4 (of the two spaces separated by P4, the space on the opposite side to the direction of gravity). Furthermore, the channel C-1 has a connecting portion Q3 with the first holding tank 20-1 of the next liquid-feeding unit in the same region. Consequently, the liquid which has flowed to the second holding tank 10-2 during rotation at the second rotation speed or when rotation is stopped does not flow as far as the first holding tank of the next liquid-feeding unit even if the liquid flows up to a midpoint of the channel C.

It is preferred that at least a part of the channel C be positioned further toward the outer circumferential side than the "plane including a liquid surface of the specimen/reagent" in the second holding tank during rotation at the first rotation speed. In such a case, during rotation at the first rotation speed, the liquid in the second holding tank can be fed more efficiently to the first holding tank of a lower level liquid-feeding unit. More specifically, the liquid continues to flow from the second holding tank to the first holding tank of the lower level liquid-feeding unit while it is positioned further on the outer circumferential side than the "plane including a liquid surface of the specimen/reagent". It is not necessary for all of the channel C to be positioned further toward the outer circumferential side than the "plane including a liquid surface of the liquid" in the second storage tank at the first rotation speed. It is only necessary for the wall of the channel C on the outer circumferential side to be positioned further toward the outer circumferential side than the "plane including a liquid surface of the liquid".

The movement process of the liquid from the second holding tank when the liquid-feeding chip is rotated at the first rotation speed is as follows. First, the "plane including a liquid surface of the liquid" in the second holding tank when the liquid-feeding chip according to the present invention begins to be rotated inclines with respect to the horizontal plane. Before reaching the first rotation speed, namely, when the channel C is further toward the outer circumferential side than the "plane including a liquid surface of the liquid" in the second holding tank, the liquid begins to flow from the second holding tank to the first holding tank of the next liquid-feeding unit due to the action of centrifugal force and gravity. Subsequently, while the "plane including a liquid surface of the liquid" in the second holding tank is still positioned further toward the inner circumferential than at least a part of the channel C, the liquid continues to flow from the second holding tank to the first holding tank of the next level liquid-feeding unit.

Figure 14:
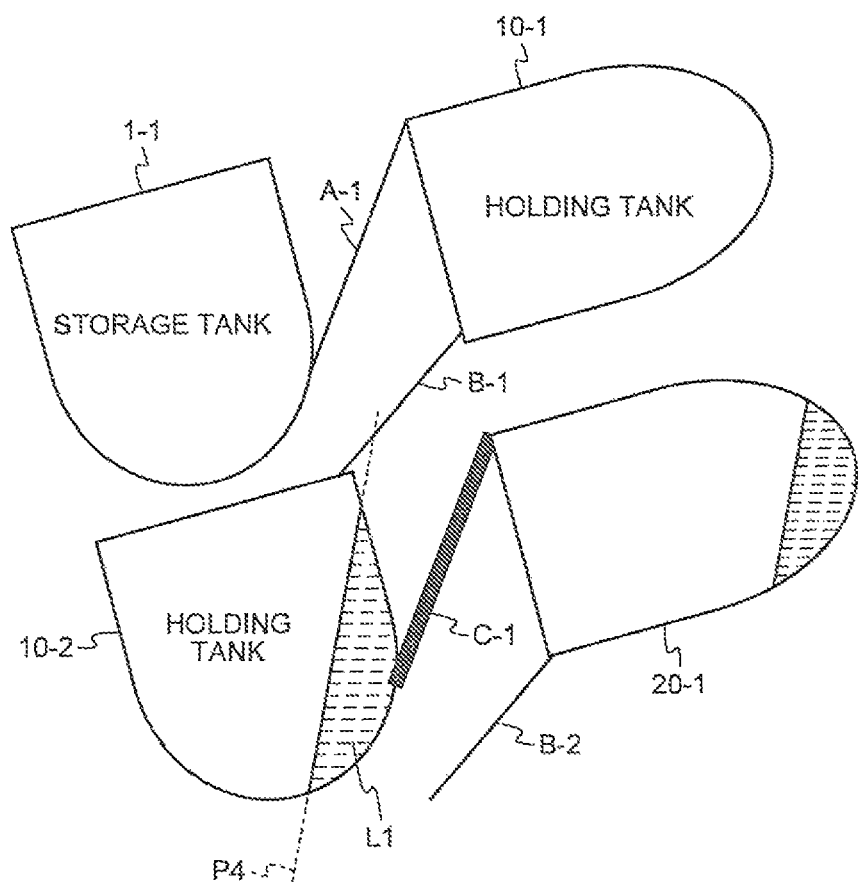
FIG. 14 is an explanatory diagram illustrating a preferred position of the channel C in the liquid-feeding chip according to the present invention with respect to the liquid surface in the second holding tank.

Therefore, when at least a part of the channel C of the liquid-feeding chip according to the present invention is positioned further toward the outer circumferential side than the "plane including a liquid surface of the specimen/reagent" in the second holding tank during rotation at the first rotation speed, all of the liquid in the second holding tank can be moved to the first holding tank of the lower level liquid-feeding unit via the channel C. For example, as illustrated in FIG. 14, when the liquid-feeding chip is rotated at the first rotation speed, a plane P4 including a liquid surface of the liquid L1 in the second holding tank 10-2 traces a line which slants upward to the right as viewed from the main surface of the liquid-feeding chip. However, since the channel C-1 is positioned further toward the outer circumferential side than the liquid surface P4 (of the two spaces separated by P4, the space on the opposite side to the axis of rotation side), the liquid can flow out during rotation at the first rotation speed until the second holding tank is empty.

In the present invention, it is preferred that the angle formed by the channel C and the axis of rotation of the liquid-feeding chip be smaller than the angle formed by the channel B and the axis of rotation of the liquid-feeding chip. This allows the problem in which liquid precedently flows out from the second holding tank which is ahead of the channel B when the liquid passes through the channel B during rotation at the second rotation speed or when rotation is stopped to be more reliably prevented. More specifically, by making the channel C closer to the vertical than the channel B, namely, by making the angle formed by the channel C and the axis of rotation to be smaller than the angle formed by the channel B and the axis of rotation, the liquid can be more reliably held in the second holding tank.

For a liquid-feeding chip having three or more liquid-feeding units, although there are a plurality of channels B, it is preferred that the angle formed by each channel B and the axis of rotation be the same. For a liquid-feeding chip having a plurality of channels B, the liquid is usually fed within the liquid-feeding chip by performing several cycles of rotation at the first rotation speed and rotation at the second rotation speed. However, in this case, the second rotation speed can be set at the same speed without changing for each cycle.

Figure 15:
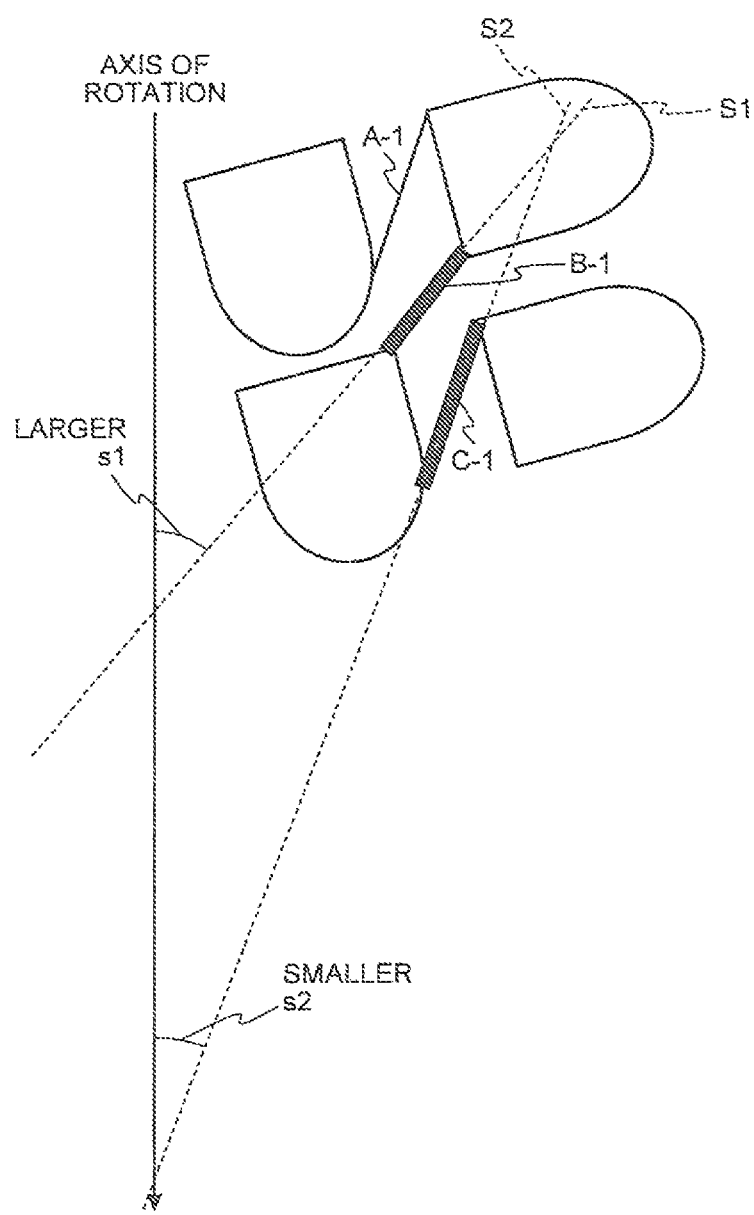
FIG. 15 is an explanatory diagram illustrating a preferred angle of the channel B and the channel C in the liquid-feeding chip according to the present invention with respect to the axis of rotation.

It is preferred that the angle formed by at least a part of the channel C in the present invention and the axis of rotation preferably have a shape forming an angle in an upwards outer circumferential direction with respect to the axis of rotation. It is preferred that the angle formed by the channel C and the axis of rotation be small, as this allows the distance between the two liquid-feeding units to be reduced, and the liquid-feeding units to be arranged without any wasted space. This angle may be appropriately set between usually 0 to 80°, preferably 1 to 45°, and more preferably 3 to 15°. At this stage, it is preferred that the angle formed by the channel C and the axis of rotation of the liquid-feeding chip be smaller than the angle formed by the channel B and the axis of rotation of the liquid-feeding chip. As described above, the liquid passes through the channel B during rotation at the second rotation speed or when rotation is stopped. At this point, by adjusting so that the channel C forms an angle which is closer to the vertical than the channel B, the specimen/reagent can be more effectively prevented from flowing from the second holding tank. More specifically, by adjusting in this manner, and by alternately repeating the rotation of the liquid-feeding chip according to the present invention at the first rotation speed and at the second rotation speed, the liquid can be sequentially fed among the tanks The "angle formed by the channel B and the axis of rotation" and the "angle formed by the channel C and the axis of rotation" mean the angle of the intersecting portion between the extension line of the respective channel and the axis of rotation. For example, as illustrated in FIG. 15, the "angle formed by the channel B and the axis of rotation" is represented by the angle s1 formed by the extension line S1 of the channel B-1 (extension line in the direction in which the liquid flows in the channel B) and the axis of rotation, and the "angle formed by the channel C and the axis of rotation" is represented by the angle s2 formed by the extension line S2 of the channel C-1 (extension line in the direction in which the liquid flows in the channel C) and the axis of rotation. In this case, s1 is greater than s2 (s1>s2). If the channel C is inflected, the angle formed between the axis of rotation and the channel C can be defined as the angle formed between the axis of rotation and the extension line extending along the line connecting the connecting portion of the second holding tank and the channel C and the point positioned at the highest point along the channel C.

The difference in the angle formed by the channel B and the axis of rotation of the liquid-feeding chip and the angle formed by the channel C and the axis of rotation may be appropriately set to between usually 0.5 to 45°, and preferably 1 to 20°.

If the liquid-feeding chip according to the present invention is composed of three or more liquid-feeding units, there are plurality of channels C. In this case, it is preferred that at least a part of each channel be parallel with the other channels. In such a case, the first rotation speed for feeding liquid from the plurality of provided second holding tanks to the first holding tank of the lower level liquid-feeding unit can be set to be the same rotation speed.

Figure 17:
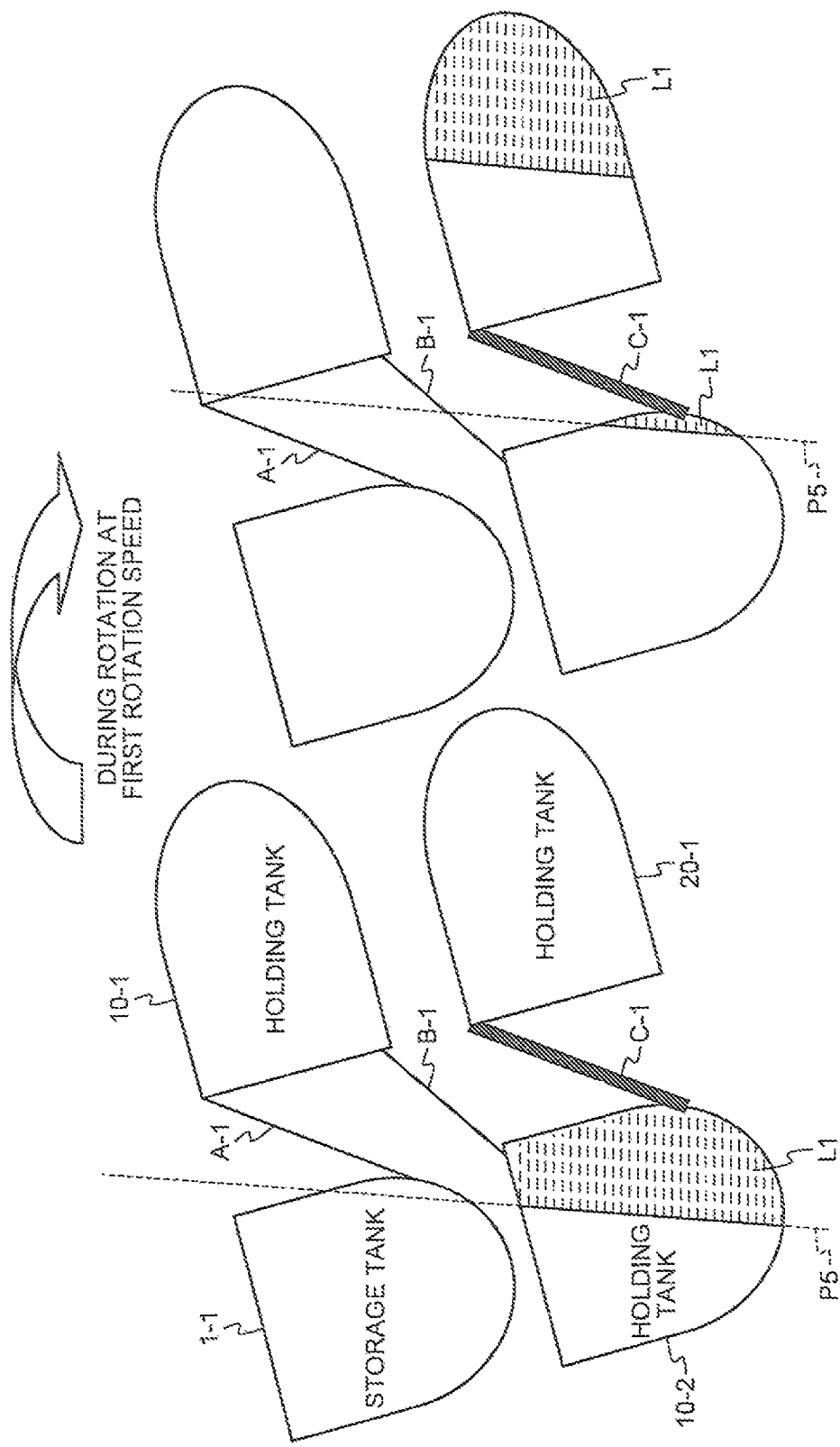
FIG. 17 is an explanatory diagram illustrating a preferred position of the channel C in the liquid-feeding chip according to the present invention with respect to the liquid surface in the second holding tank.

It is preferred that the channel C be positioned further toward the outer circumferential side than the plane which passes through a connecting portion of the channel C and the second holding tank and which is perpendicular to the combined force of the centrifugal force and gravity at the first rotation speed. This allows a liquid which has been introduced into the second storage tank to be fed to the first holding tank of the lower level liquid-feeding unit when rotating the liquid-feeding chip at the first rotation speed. For example, as illustrated in FIG. 17, when the liquid-feeding chip is rotated at the first rotation speed, a plane P5 including a liquid surface of the liquid L1 in the second holding tank 10-2 traces a line which slants upward to the right as viewed from the main surface of the liquid-feeding chip. However, when the channel C-1 is positioned further toward the outer circumferential side than the liquid surface P5 (of the two spaces separated by P5, the space on the opposite side to the space in which the axis of rotation is located), the liquid can flow out until the second holding tank 10-2 is empty.

Figure 16:
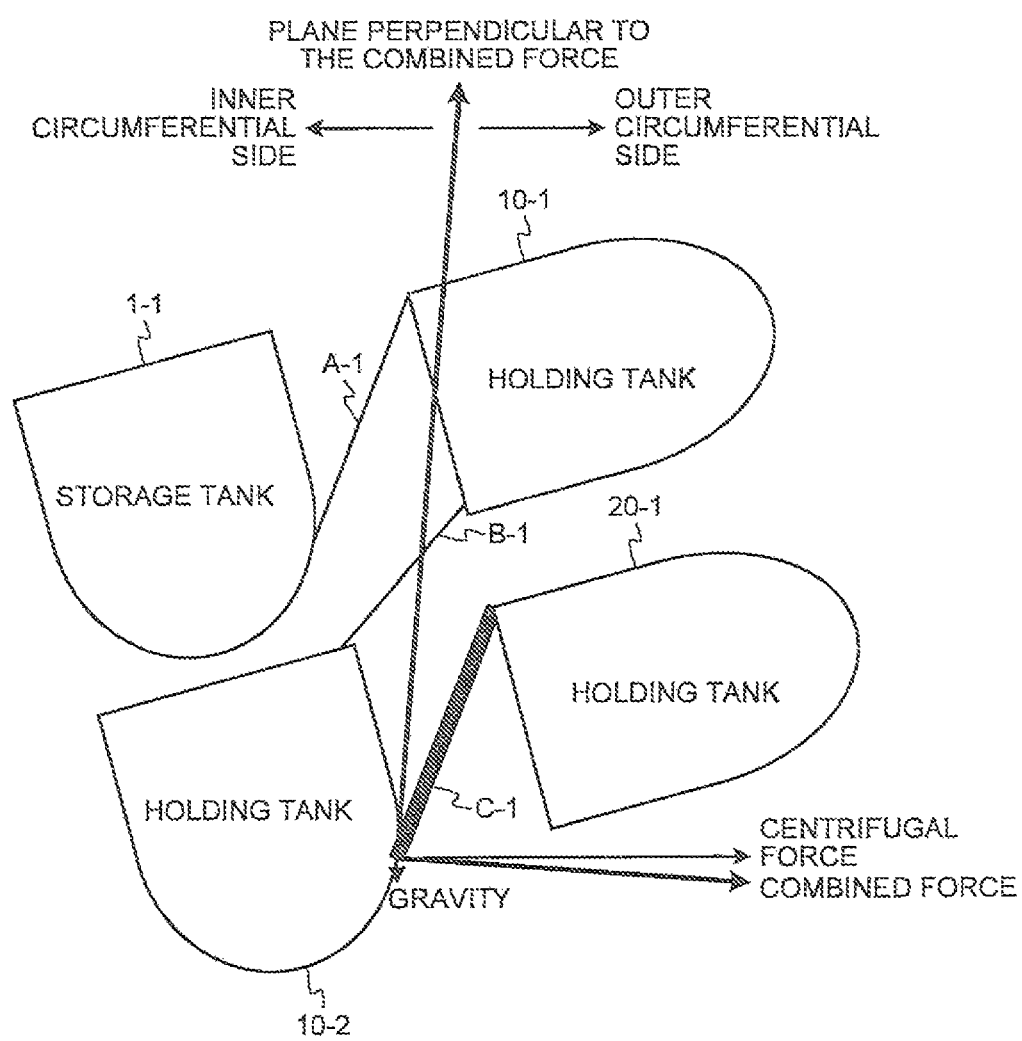
FIG. 16 is an explanatory diagram illustrating a preferred position of the channel C in the liquid-feeding chip according to the present invention with respect to centrifugal force and gravity acting on the liquid-feeding chip.

The expression "plane which passes through a connecting portion of the channel C and the second holding tank and which is perpendicular to the combined force of the centrifugal force and gravity at the first rotation speed" means the plane which forms an angle perpendicular to the combined force of the centrifugal force and gravity acting on the connecting portion of the channel C and the second holding tank of the liquid-feeding chip when the liquid-feeding chip is rotated at the first rotation speed, and which intersects that connecting portion. For example, if the direction and magnitude of the centrifugal force acting on the liquid-feeding chip and of gravity are indicated by the arrows as illustrated in FIG. 16, the combined force of the centrifugal force and gravity is represented by the direction and the magnitude indicated by the thick line facing in the outer circumferential direction. Therefore, the expression "the plane which passes through a connecting portion of the channel C and the second holding tank and which is perpendicular to the combined force of the centrifugal force and gravity at the first rotation speed" means that the channel C is positioned in the space (outer circumferential side) of the side opposite to the space (inner circumferential side) in which the axis of rotation is located with respect to the plane which passes through the perpendicular arrow (in FIG. 16, the thick arrow) with respect to the thick arrow indicating the combined force.

It is preferred that the connecting portion of the channel C in the present invention and the first holding tank of the lower level liquid-feeding unit be positioned further toward the inner circumferential with respect to the axis of rotation of the liquid-feeding chip than the "plane including a liquid surface of the specimen/reagent" in the first holding tank of the lower level liquid-feeding unit at the first rotation speed. By doing so, flow of the liquid downstream, such as to the second holding tank, from the first holding tank of the lower level liquid-feeding unit during rotation at the first rotation speed can be more effectively prevented.

The shape and the size of the channel C are not specifically limited, as long as the overall channel has a tube shape. The whole channel C does not have to have the same shape. Furthermore, the channel C may be an aperture which directly connects the second holding tank to the first holding tank of the lower level liquid-feeding unit. The shape of the transverse cross-section is not specifically limited to a circle, a polygon or the like. The size of the transverse cross-section also does not have to be fixed, and may be appropriately adjusted to a size through which the specimen/reagent can pass. For example, the short diameter (for a circle, this means the radius, and for a polygon, this means the shortest diameter passing through the center) is usually in the range of 10 μm to 5 mm, and preferably in the range of 500 μm to 3 mm. If the short diameter of the channel C is shorter, the time required to feed the liquid from the second holding tank to the first holding tank of the lower level liquid-feeding unit at the first rotation speed becomes longer. If the short diameter is longer, the required time becomes shorter.

Furthermore, as long as the channel C connects the second holding tank to the first holding tank of the lower level liquid-feeding unit, the channel C does not have to be completely straight. Part of the channel C may be curved or have an irregular shape. The extension shape of the channel C may be a mix of straight lines and curves, and may even be inflected midway along.

Furthermore, the channel C and the second holding tank may be integrated. As illustrated in FIG. 3, the first holding tank of the lower level liquid-feeding unit may be directly in communication with the second holding tank. In this case, the inner wall portions C-11 and C-21 of the second holding tanks 10-2 and 20-2 on the outer circumferential side can be considered as the channel C. More specifically, the angle formed between the inner wall portions C-11 and C-21 of the second holding tanks on the outer circumferential side and the axis of rotation may be appropriately set between usually 0 to 80°, preferably 1 to 45°, and more preferably 3 to 15°. In such a case, the angle formed between the inner wall portions C-11, C-21, and D-11 of the second holding tanks on the outer circumferential side and the axis of rotation of the liquid-feeding chip is preferably smaller than the angle formed between the channel B and the axis of rotation of the liquid-feeding chip.

(Channel D)

The liquid-feeding chip according to the present invention may have a channel D for discharging a liquid by the first rotation speed from the second holding tank of the lowest level liquid-feeding unit. Consequently, a resultant product (usually a liquid) obtained by sequentially feeding the specimen/reagent introduced into the liquid-feeding chip from the respective tanks by rotation can be extracted from the final tank via this channel D.

For example, as illustrated in FIG. 1, one end of the channel D is connected so as to open up a lower portion of the lowest level second storage tank on the outer circumferential side, and the other end is extended in an upwards outer circumferential direction.

It is preferred that the channel D in the liquid-feeding chip according to the present invention be configured so that liquid is held in the second holding tank connected to the channel D during rotation at the second rotation speed or when rotation is stopped. Furthermore, it is preferred that the channel D be configured so that the liquid in this second holding tank is fed downstream via the channel D by the action of centrifugal force during rotation at the first rotation speed, which is faster than the second rotation speed. In such a case, during rotation at the second rotation speed or when rotation is stopped, the liquid held in the second holding tank can be fed downstream by increasing the rotation speed, thereby enabling control to sequentially feed the liquid.

It is preferred that at least a part of the channel D include a region which is positioned further toward the inner circumferential or higher than the "plane including a liquid surface of the specimen/reagent" in the second holding tank during rotation at the second rotation speed or when rotation is stopped. In such a case, during rotation at the second rotation speed or when rotation is stopped, the liquid which has flowed from the first holding tank to the second holding tank can be more reliably held in the second holding tank without flowing into a below-described reaction tank.

Figure 18:
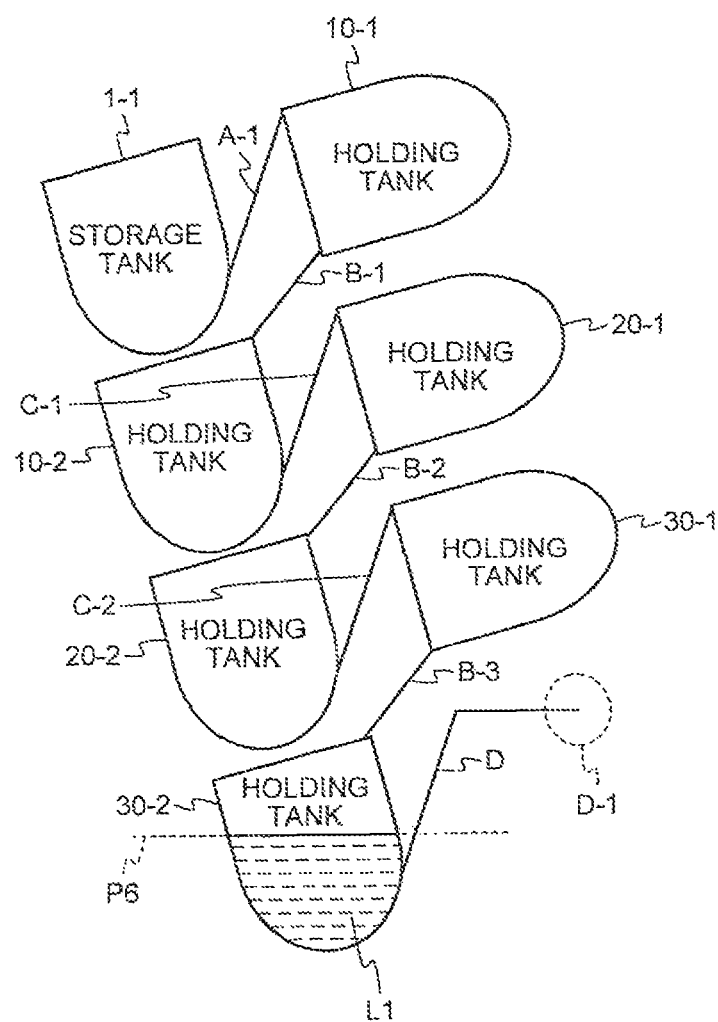
FIG. 18 is an explanatory diagram illustrating a preferred position of a channel D in the liquid-feeding chip according to the present invention with respect to the liquid surface in the second holding tank.

For example, as illustrated in FIG. 18, during rotation at the second rotation speed or when rotation is stopped, the lower half region of the channel D is positioned higher than the liquid surface P6 of the second holding tank 30-2.

It is preferred that the channel D be positioned further toward the outer circumferential side than the "plane including a liquid surface of the specimen/reagent" in the second holding tank which the channel D is connected to, during rotation at the first rotation speed. In such a case, during rotation at the first rotation speed, the liquid in the second holding tank can be fed more efficiently to the below-described reaction tank. It is not necessary for all of the channel D to be positioned further toward the outer circumferential side than the "plane including a liquid surface of the liquid" in the second holding tank at the first rotation speed. It is only necessary for at least the wall of the channel D on the outer circumferential side to be positioned further toward the outer circumferential side. Furthermore, it is not necessary for all of the channel D to be positioned further toward the outer circumferential side than the "plane including a liquid surface of the liquid" in the second storage tank at the first rotation speed. It is only necessary for the wall of the channel C on the outer circumferential side to be positioned further toward the outer circumferential side than the "plane including a liquid surface of the liquid."

It is preferred that the channel D be positioned further toward the outer circumferential side than the plane which is perpendicular to the combined force of the centrifugal force and gravity at the first rotation speed. This allows a liquid which has been introduced into the second holding tank to be more efficiently fed to the below-described reaction tank when the liquid-feeding chip is rotated at the first rotation speed. Here, the definitions of the "plane which is perpendicular to the combined force of the centrifugal force and gravity" and "further toward the outer circumferential side than that plane" are as described for the channels A and C.

It is preferred that at least a part of the channel D according to the present invention be parallel to at least a part of the channel A of the upper level liquid-feeding unit. In such a case, the first rotation speed for feeding liquid from the first storage tank to the first holding tank and the first rotation speed for feeding liquid from the second holding tank to the first holding tank of the lower level liquid-feeding unit can be set to be the same rotation speed. In addition, when liquid has been introduced into the first storage tank and the second holding tank in advance, these liquids can be simultaneously fed to the next tank by carrying out rotation at the same first rotation speed.

An end portion of the channel D on the opposite side to the connecting end with the second holding tank (the portion indicated as D-1 in the example of FIG. 18) may be connected with a separate tank, such as the reaction chamber (reaction tank), or with a discharge passage. Examples of a liquid-feeding chip in which the channel D is connected to a discharge passage include the liquid-feeding chips illustrated in FIGS. 1 to 3, 25 and 26. Furthermore, an example of a liquid-feeding chip in which the channel D is connected to a reaction chamber include the liquid-feeding chip illustrated in FIG. 4.

(Discharge Passage)

When the channel D has a discharge passage, within the channel D, it is preferred that the discharge passage be positioned downstream of a region which is positioned higher than the "plane including a liquid surface of the specimen/reagent" in the second holding tank formed during rotation at the second rotation speed or when rotation is stopped. This allows the liquid to be more reliably held in the second holding tank.

This will be described with reference to FIG. 18 using a liquid-feeding chip which has stopped being rotated as an example. When rotation is stopped, a liquid L1 in the second holding tank 30-2 forms a plane P6 including a liquid surface. A part of the channel D has a region positioned in a space which is above this plane P6 (of the two spaces separated by P6, the space on the opposite side to the direction of gravity). Furthermore, the channel D has a discharge passage D-1 in the same region.

In the present invention, it is preferred that the angle formed by the channel B and the axis of rotation of the liquid-feeding chip be larger than the angle formed by the channel D and the axis of rotation of the liquid-feeding chip. This allows the problem in which liquid precedently flows from the second holding tank which is ahead of the channel B when the liquid passes through the channel B during rotation at the second rotation speed or when rotation is stopped to be more reliably prevented. More specifically, by making the channel D closer to the vertical than the channel B, namely, by making the angle formed by the channel D and the axis of rotation to be smaller than the angle formed by the channel B and the axis of rotation, the liquid can be more reliably held in the second storage tank.

It is preferred that the channel D in the present invention have a shape in which at least a part forms an angle on the upwards outer circumferential side with respect to the axis of rotation. More preferred is a shape in which an angle of 0 to 80° is formed. Even more preferably, the angle can be appropriately set between 1 to 45°, and still more preferably 3 to 15°. The angle formed by the channel D with respect to the axis of rotation is similar to what was already described above concerning the others channels, and thus a description thereof will be omitted here.

The shape and the size of the channel D are not specifically limited, as long as the overall channel has a tube shape. The whole channel D does not have to have the same shape. Furthermore, when the channel D is connected to a reaction chamber (reaction tank), the channel D may be an aperture which directly connects the second storage tank to the reaction chamber (reaction tank). The shape of the transverse cross-section is not specifically limited to a circle, a polygon or the like. The size of the transverse cross-section also does not have to be fixed, and may be appropriately adjusted to a size through which the specimen/reagent can pass. For example, the short diameter (for a circle, this means the radius, and for a polygon, this means the shortest diameter passing through the center) is usually in the range of 10 μm to 5 mm, and preferably in the range of 100 μm to 3 mm. If the short diameter of the channel D is shorter, the time required to feed the liquid from the second holding tank to the below-described reaction tank at the first rotation speed becomes longer. If the short diameter is longer, the required time becomes shorter.

Furthermore, as long as the channel D is connected to a second holding tank, the channel D does not have to be completely straight. Part of the channel D may be curved or have an irregular shape. The channel D may be formed from a mix of straight lines and curves, and may even have an inflection midway along.

The channel A, channel B, and channels B, C, and D of the lower level liquid-feeding unit in the present invention may have a tubular structure connecting the storage tanks to the holding tanks, or an open structure so that the storage tanks and the holding tanks are in directly communication with each other.

Furthermore, the channel D and the second holding tank of the lowest level liquid-feeding unit may be integrated with each other. In addition, in this case, the second holding tank of the lowest level liquid-feeding unit and the below-described reaction tank may be in direct communication with each other. In such a case, an inner wall portion of the second holding tank on the outer circumferential side can be considered as the channel D.

Specifically, for example, as illustrated in FIG. 3, the inner wall portion D-11 of the second holding tank 30-2 on the outer circumferential side can be considered as the channel D. The angle formed between the inner wall portion of the second holding tanks on the outer circumferential side and the axis of rotation may be appropriately set between usually 0 to 80°, preferably 1 to 45°, and more preferably 3 to 15°. In such a case, the angle formed between the inner wall portion of the second holding tank on the outer circumferential side and the axis of rotation of the liquid-feeding chip is preferably smaller than the angle formed between the channel B and the axis of rotation.

It is preferred that the channels A, C, and D included in the liquid-feeding chip according to the present invention all form the same angle with respect to the axis of rotation. In such a case, the liquid can be fed to a downstream tank by rotation at the same first rotation speed. Furthermore, this also allows liquid feeding to be controlled more easily.

The liquid-feeding chip according to the present invention may have two or more of the above-described liquid-feeding units. The number of liquid-feeding units is not specifically limited.

The more the number of liquid-feeding units is increased, the more the liquid feeding step can be slowed until the final level. In addition, this also allows the types of specimen/reagent which can be sequentially fed to be increased. Thus, when a plurality of liquid-feeding units are used, by repeating rotation at the first rotation speed and rotation at the second rotation speed (or stopping rotation), a plurality of types of specimen/reagent can be sequentially fed.

The liquid-feeding chip according to the present invention can also have a second storage tank and a channel E in at least one liquid-feeding unit among the plurality of liquid-feeding units. Consequently, a liquid can be injected into each level of the liquid-feeding units and held in the first holding tank at the first rotation speed. This allows a plurality of types of liquid to be sequentially fed.

(Second Storage Tank)

A second storage tank may also be arranged on the inner circumferential side of the second holding tank with respect to the axis of rotation of the liquid-feeding chip.

Figure 4:
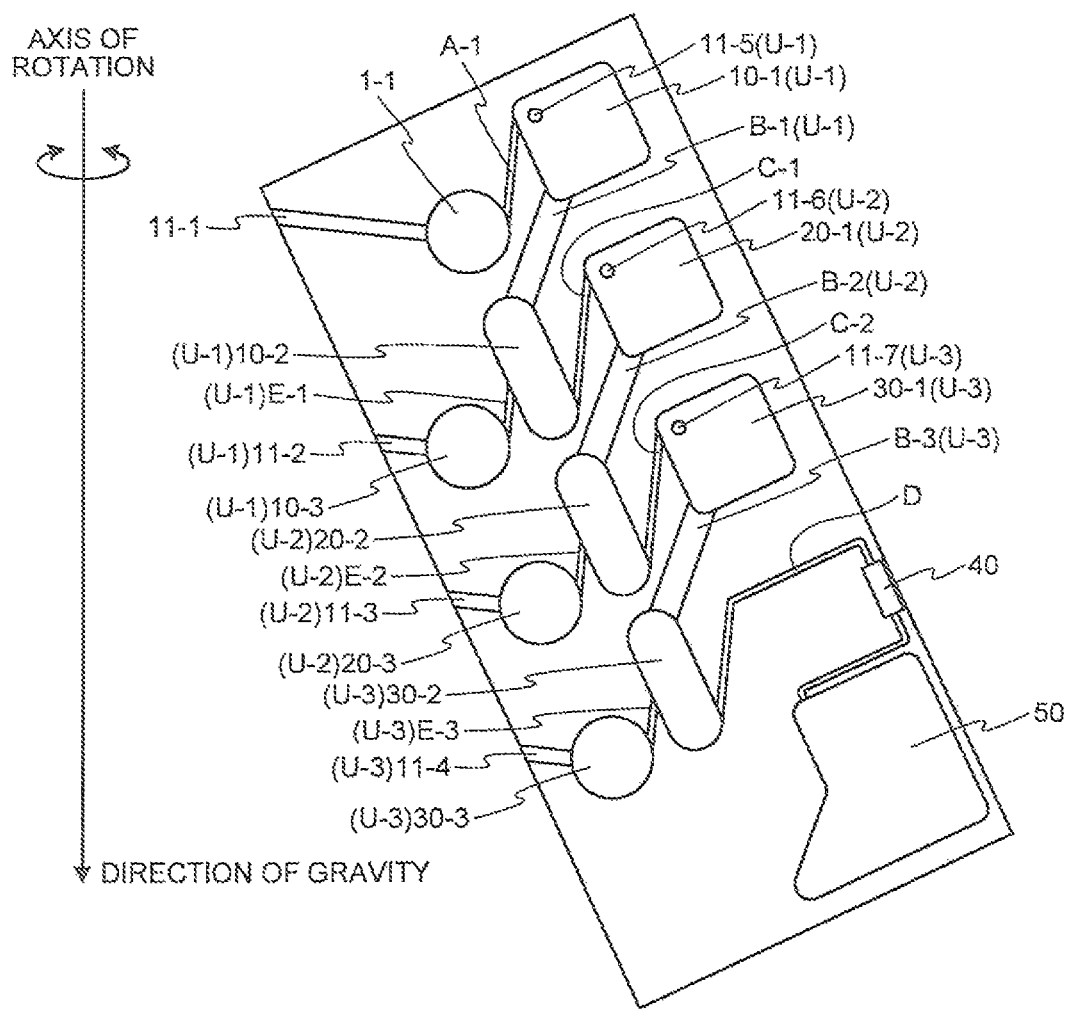
FIG. 4 is a plan view illustrating another example of a liquid-feeding chip according to the present invention.

As illustrated in FIG. 4, for example, a second storage tank 10-3 can be arranged on the downwards inner circumferential side from the second holding tank 10-2. Since the reagent and/or specimen is normally contained in advance in the second storage tank before rotation, the second storage tank may have an aperture so that the reagent and/or specimen can be injected therein. The capacity of the second storage tank is not specifically limited as long as the tank can contain the reagent and/or specimen. However, a storage tank which can contain 0.001 mL to 10 mL, and within that, 0.01 mL to 1 mL, of a liquid is preferred. Furthermore, the shape of the second storage tank is not specifically limited. The shape may be appropriately selected from among shapes such as a rough sphere, cylinder, rectangular solid, pyramid, cone and the like.

(Channel E)

As illustrated in FIGS. 4, 19, and 24 to 27, a channel E is a channel which allows the second storage tank and the second holding tank or the first holding tank to be in communication with each other. One end of the channel E is connected so as to open up a lower portion of the second storage tank on the outer circumferential side, and the other end is connected so as to open up an upper portion of the second holding tank on the axis of rotation side. This channel E is a channel for feeding a liquid from the second storage tank to the second holding tank or the first holding tank by the action of centrifugal force and gravity during rotation at the first rotation speed.

It is preferred that at least a part of the channel E in the present invention form an angle of 0 to 90° on the upwards outer circumferential side with respect to the axis of rotation, and an angle of 0 to 90° on the downwards outer circumferential side (outer circumferential side direction and the direction of gravity) with respect to the axis of rotation. This angle may be appropriately set in the range of more preferably 1 to 90°, even more preferably 1 to 45°, and most preferably 1 to 15° on the upwards outer circumferential side (opposite direction to the outer circumferential side direction and the direction of gravity).

The shape and the size of the channel E are not specifically limited, as long as the overall channel has a tube shape. The whole channel E does not have to have the same shape. Furthermore, the channel E may be an aperture which directly connects the second storage tank to the second holding tank or the first holding tank. The shape of the channel cross-section of the channel E is not specifically limited to a circle, a polygon or the like. The size of the transverse cross-section of the channel E also does not have to be fixed, and may be appropriately adjusted to a size through which the specimen/reagent can pass. For example, the short diameter (for a circle, this means the radius, and for a polygon, this means the shortest diameter passing through the center) of the channel E is usually in the range of 10 µm to 5 mm, and preferably in the range of 100 µm to 1 mm. If the short diameter of the channel E is shorter, the time required to feed the liquid from the second storage tank to the second holding tank or the first holding tank at the first rotation speed becomes longer due to pressure loss. If the short diameter is longer, the required time becomes shorter.

Furthermore, as long as the channel E connects the second storage tank to the second holding tank or the first holding tank, the channel E does not have to be completely straight. Part of the channel E may be curved or have an irregular shape. The extension shape of the channel E may be a mix of straight lines and curves, and may even be inflected midway along.

It is preferred that the channel E be positioned further toward the outer circumferential side than the plane which passes through a connecting portion of the channel E and the second storage tank and which is perpendicular to the combined force of the centrifugal force and gravity at the first rotation speed. This allows a liquid which has been introduced into the second storage tank to be fed from the second storage tank to the second holding tank or the first holding tank when the liquid-feeding chip is rotated at the first rotation speed. Furthermore, this allows that liquid to be fed as is to the second holding tank, the first holding tank, or the reaction chamber. Here, the definitions of the "plane which is perpendicular to the combined force of the centrifugal force and gravity" and "further toward the outer circumferential side than that plane" are as described for the channels A and C.

It is preferred that at least a part of the channel E be positioned further toward the outer circumferential side than the "plane including a liquid surface of the specimen/reagent" in the first storage tank at the first rotation speed. Consequently, when the liquid-feeding chip is rotated at the first rotation speed, liquid which has been introduced into the second storage tank can be fed more reliably to the second holding tank or the first holding tank. It is not necessary for all of the channel E to be positioned further toward the outer circumferential side than the "plane including a liquid surface of the liquid" in the second storage tank at the first rotation speed. It is only necessary for the wall of the channel E on the outer circumferential side to be positioned further toward the outer circumferential side than the "plane including a liquid surface of the liquid."

The expression "liquid surface of the liquid in the second storage tank at the first rotation speed" is similar to what was described regarding the first storage tank for the channel A. This expression means a plane including a liquid surface formed by the liquid in the second storage tank when the liquid-feeding chip having a second storage tank into which liquid has been introduced is rotated at the first rotation speed.

The movement process of the liquid from the second storage tank when the liquid-feeding chip is rotated at the first rotation speed is as follows. First, the "plane including a liquid surface of the liquid" in the second storage tank when the liquid-feeding chip according to the present invention begins to be rotated inclines with respect to the horizontal plane. Before reaching the first rotation speed, namely, when the channel E is further toward the outer circumferential side than the "plane including a liquid surface of the liquid" in the second storage tank, the liquid begins to flow from the second storage tank into the second holding tank or the first holding tank due to the action of centrifugal force and gravity. Subsequently, while the "plane including a liquid surface of the liquid" in the second storage tank is still positioned further toward the inner circumferential than at least a part of the channel E, the liquid continues to flow from the second storage tank to the second holding tank or the first holding tank.

Figure 19:
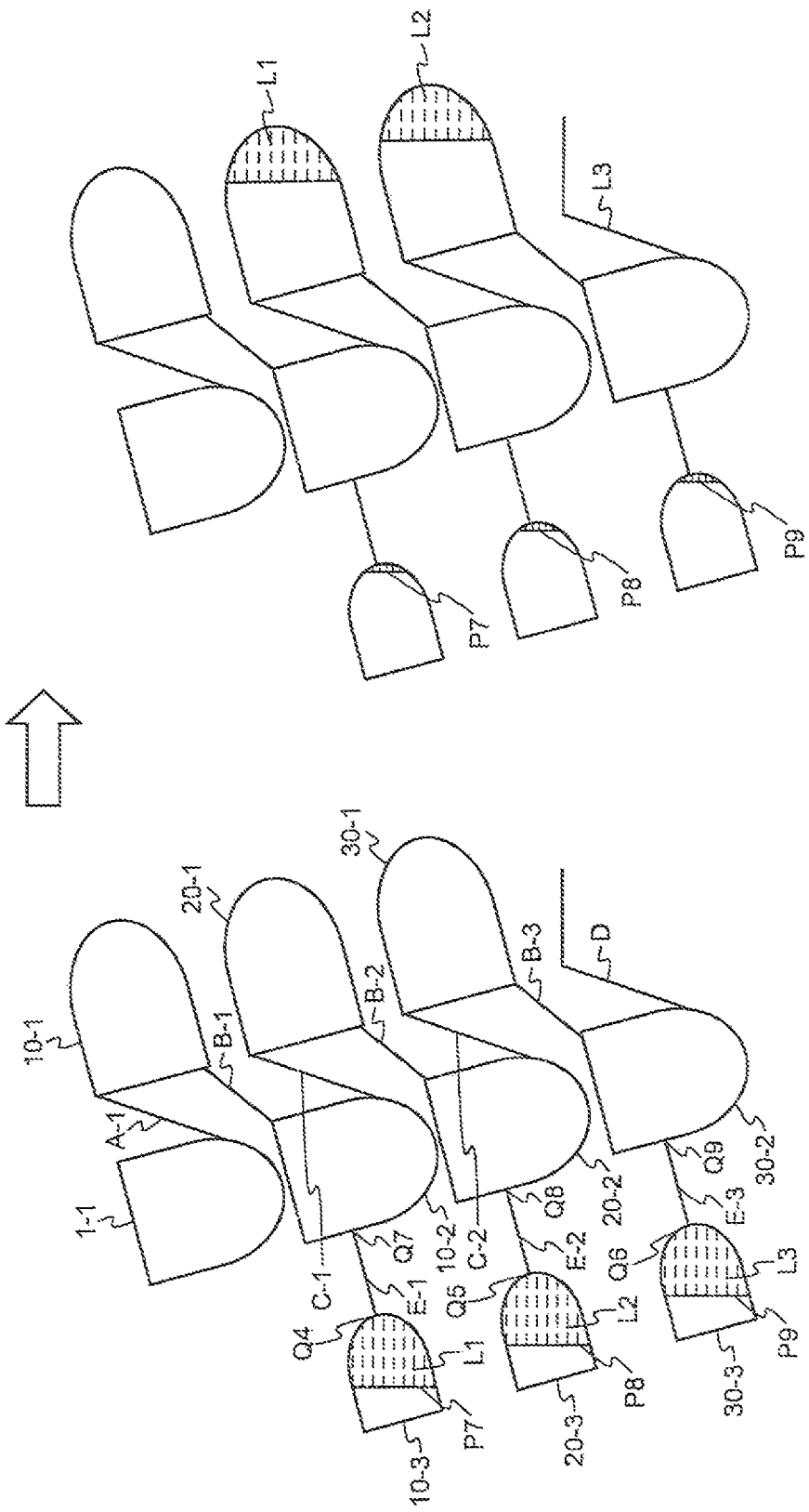
FIG. 19 is an explanatory diagram illustrating preferred positions of a channel E and a second storage tank in the liquid-feeding chip according to the present invention.

Therefore, when at least a part of the channel E of the liquid-feeding chip according to the present invention is positioned further toward the outer circumferential side than the "plane including a liquid surface of the specimen/reagent" in the second storage tank at the first rotation speed, all of the liquid in the second storage tank can be moved to the second holding tank via the channel E. For example, as illustrated in FIG. 19, when the rotation of the liquid-feeding chip has reached the first rotation speed, planes P7, P8, and P9 including liquid surfaces of liquids L1, L2, and L3 of the second storage tanks 10-3, 20-3, and 30-3, respectively, trace a line which slants upward to the right as viewed from the main surface of the liquid-feeding chip. However, when the channel E is positioned further toward the outer circumferential side than these planes (separated by P7, P8, and P9, the opposite side to that where the axis of rotation is located), the liquid can flow out until the second storage tank is empty.

Furthermore, it is preferred that a connecting portion of the channel E and the second storage tank be positioned further toward the outer circumferential side during rotation than the "plane including a liquid surface of the specimen/reagent" in the second storage tank at the first rotation speed. This allows the liquid in the second storage tank during rotation at the first rotation speed to be more reliably fed to the second holding tank or the first holding tank. In addition, liquid can be fed to the channel D, and liquid can be fed to the first holding tank of the next level liquid-feeding unit via the channel C. For example, as illustrated in FIG. 19, since connecting portions Q4 and Q5 of the second storage tanks 10-3 and 20-3 and the channel E are positioned further toward the outer circumferential side during rotation than the planes P7 and P8 (separated by P7 and P8, the opposite side to that where the axis of rotation is located), the liquid in the second storage tank can pass through the second holding tank and the channels C-1 and C-2 without stagnating, and be fed to the first holding tanks 20-1 and 30-1 of the next level liquid-feeding unit (right side in FIG. 19). Furthermore, since a connecting portion Q6 of the second storage tank 30-3 and the channel E is allowed to be positioned further toward the outer circumferential side during rotation than the plane P9 (separated by P9, the opposite side to that where the axis of rotation is located), the liquid in the second storage tank can be fed to the channel D without stagnating. In addition, the liquid fed to the first storage tanks 20-1 and 30-1 moves to the second holding tanks 20-2 and 30-2 which are in the direction of gravity through the channels B-2 and B-3 during rotation at the second rotation speed or when rotation is stopped (figures not shown).

Furthermore, it is preferred that a connecting portion of the channel E with the second holding tank or the first holding tank be positioned closer to the axis of rotation (inner circumferential side) than the plane including a liquid surface of the liquid in the second holding tank or the first holding tank at the first rotation speed. When the liquid-feeding chip is rotated at the first rotation speed, the liquid fed from the second storage tank forms a liquid surface which is approximately perpendicular to the combined force of the centrifugal force and gravity at the second holding tank or the first holding tank. However, since the connecting portion of the channel E with the second holding tank or the first holding tank is positioned closer to the axis of rotation than this plane including the liquid surface, the liquid can be reliably held by the second holding tank or the first holding tank during rotation at the first rotation speed. Furthermore, this also allows back flow to the second storage tank to be more effectively prevented.

In the liquid-feeding chips illustrated in FIGS. 26 and 27, the second storage tank 10-3 is connected to the first holding tank 20-1 of the second liquid-feeding unit (U-2) via a channel E-2. A second storage tank 40-3 is connected to a second holding tank 40-2 of a fourth liquid-feeding unit (U-4) via a channel E-4.

(Reaction Chamber)

As illustrated in FIG. 4, the liquid-feeding chip according to the present invention may have a reaction chamber in communication with the channel D. The term "reaction chamber" in the present invention means a region in which the specimen/reagent reacts. Specific examples of reactions include an antigen-antibody reaction, a hybridization reaction, an enzyme reaction, a denaturation reaction, a cross-linking reaction and the like. Preferred examples include an antigen-antibody reaction, a hybridization reaction, and an enzyme reaction.

The reaction chamber in the present invention does not have to be connected to the channel D. Furthermore, a holding tank may serve as a reaction chamber. For example, the second holding tank of the lowest level liquid-feeding unit may be utilized as the reaction chamber.

Beads (a carrier) on which an antibody or an antigen is bound may be filled into the reaction chamber of the present invention. In such a case, an antigen-antibody reaction can be carried out by feeding a specimen/reagent including a substance which is specifically bound to an antibody or an antigen.

(Waste Tank)

As illustrated in FIG. 4, for example, the liquid-feeding chip according to the present invention may have a waste tank 50 which is in communication with a reaction chamber 40. In such a case, waste liquid can be held in the liquid-feeding chip, which allows the risk of leaks from the liquid-feeding chip of a specimen which may be infectious, or a specimen/reagent which is suspected of being poisonous or environmentally toxic to be reduced. Furthermore, this can also reduce the risk of coming into contact with a person's body. The waste tank 50 is a tank for storing a specimen/reagent which has passed through all the thanks The waste tank 50 is positioned at a location where centrifugal force is applied during rotation at the first rotation speed of the liquid-feeding chip. Usually, the waste tank 50 is a lower corner portion on the side farthest from the axis of rotation of the liquid-feeding chip. The size of the waste tank 50 is not specifically limited as long as the tank is capable of storing the waste liquid. However, a waste tank that can store 0.01 to 20 mL, and within that, 0.2 to 5 mL is preferred. Furthermore, it is preferred that the capacity of the waste tank be larger than that of the other storage tanks The shape of the waste tank is not specifically limited. The shape may be appropriately selected from among shapes such as a sphere, rectangular solid, prismatic column, cylinder and the like.

The liquid-feeding chip according to the present invention may be configured so that different specimens/reagents flow into at least one holding tank, and are mixed in the interior of that holding tank. This allows a plurality of specimens/reagents to be mixed in the interior of the holding tanks, so that reagents which are unstable after mixing can be held in different holding tanks, and mixed in the holding tanks by rotation.

A plurality of the liquid-feeding chips according to the present invention may be connected to a common channel or a common tank. In this case, even if one specimen/reagent is stored in advance in one of the liquid-feeding chips, different specimen/reagents may be sequentially flowed from a different liquid-feeding chip to the common channel or tank. Obviously, this enables the types of specimen/reagent which can be sequentially flowed from to the common channel or tank to be increased, when the respective liquid-feeding chips contain a plurality of specimen/reagents.

(Specimen/Reagent Containment, Reagent Reservoir Unit)

The specimen/reagent does not have to be contained in the storage tanks or holding tanks when the liquid-feeding chip according to the present invention is mounted on the rotation apparatus. However, normally, a predetermined specimen/reagent is contained in any of the tanks prior to rotation of the liquid-feeding chip. By containing (storing) a predetermined specimen/reagent in advance in the liquid-feeding chip before mounting on the rotation apparatus, an operation for injecting the reagent into the liquid-feeding chip while the chip is mounted on the rotation apparatus can be omitted.

It is especially preferred that different specimen/reagents be stored in advance in at least two tanks including a storage tank and the second holding tank. This allows different specimen/reagents to be sequentially fed by rotation. It is more preferred that different specimen/reagents be stored in advance in at least two tanks selected from the first storage tank, the second storage tank, and a second holding tank from one of the plurality of units arranged at a lower level.

As illustrated in FIG. 27, the first storage tank and/or second storage tank in the present invention may be provided as a removably-mounted reagent reservoir unit F on a liquid-feeding chip body G. Furthermore, the configuration example illustrated in FIG. 27 has the same configuration as the configuration example illustrated in FIG. 26 described above, except that the first and second storage tanks are provided on the separate removably-mounted reagent reservoir unit F.

It is preferred that the reagent reservoir unit F in the present invention have a reagent stored in advance in a tank formed in its interior. Preferably, the reagent reservoir unit F can maintain the stability and performance of the reagent for 10 days or more. Typically, a first storage tank and/or a second storage tank is provided in the reagent reservoir unit F. A part of the channel A (A-1$a$ and A-1$b$) and channel E (E-2 and E-4) or an aperture is provided on the reagent reservoir unit F. When this reagent reservoir unit is connected to the liquid-feeding chip body G (during use), it is in communication with the first storage tank and/or second storage tank. A structure functioning as a liquid-feeding chip is obtained by having the first storage tanks (1-1$a$ and 1-$b$) and/or second storage tanks (10-3 and 40-3) of the reagent reservoir unit F be engaged and in communication with the first holding tanks (10-1 and 20-1) and/or second holding tank (40-2).

To achieve long-term storage stability of a liquid reagent, for example, it is preferred that the reagent reservoir unit in the present invention be formed from a resin having low moisture absorbance. In addition, to prevent degradation from light, it is preferred that the reagent reservoir unit be formed from a resin having low light transmittance.

Therefore, it is preferred to provide the reagent reservoir unit having a first storage tank and/or a second storage tank so that it can be mounted on and removed from the liquid-feeding chip (liquid-feeding chip body G), as this enables a resin to be selected which is appropriate for the functions demanded at each section and each unit of a single liquid-feeding chip. Furthermore, this also enables the costs of the overall liquid-feeding chip to be suppressed.

Furthermore, at least a part of the reagent reservoir unit may be formed from a resin having a moisture absorption property of 0.1% or less, and preferably 0.03% or less. This is preferable because it enables long-term storage of the reagent without the reagent concentration changing. An upper limit of the moisture absorption is usually 0.2%. The moisture absorption can be measured by weight measurement. Further, the moisture absorption can also be measured in accordance with the JIS standard JIS K7209.

In addition, at least a part of the reagent reservoir unit may be formed from a resin having a light transmittance (light beam transmittance) property of 10% or less, and preferably 1% or less. This is preferable because it allows a photodegradable reagent to be stored. The light transmittance may be measured by a spectrophotometer. Further, the light transmittance can also be measured in accordance with the JIS standard JIS K7105. To reduce the light transmittance, a resin containing a pigment, carbon or the like may be used.

Examples of the material for the reagent reservoir unit may include those described above as material for the liquid-feeding chip. Specifically, preferred examples include polypropylene and polyethylene.

To suppress reagent evaporation, a film may be adhered to the aperture in the reagent reservoir unit. In such a case, the film is removed just before use, and the reagent reservoir unit is mounted on the liquid-feeding chip body so that the liquid can be fed.

Although an example was described here of a configuration having the storage tank of the liquid-feeding chip illustrated in FIG. 27 as the separate reagent reservoir unit, configurations in which the storage tank is prepared as the separate reagent reservoir unit may also be used in the other exemplary configurations of the liquid-feeding chip according to the present invention, such as the liquid-feeding chip illustrated in FIG. 1, for example.

Further, it is preferred that at least one of the holding tanks included in the liquid-feeding chip according to the present invention be a tank which is connected to a storage tank and/or holding tank on a higher level than that holding tank via a plurality of channels, so that different specimen/reagents which have flowed from the respective tanks can be mixed in the interior of that holding tank. This allows a plurality of specimen/reagents to be simultaneously mixed.

Figures 1, 22:
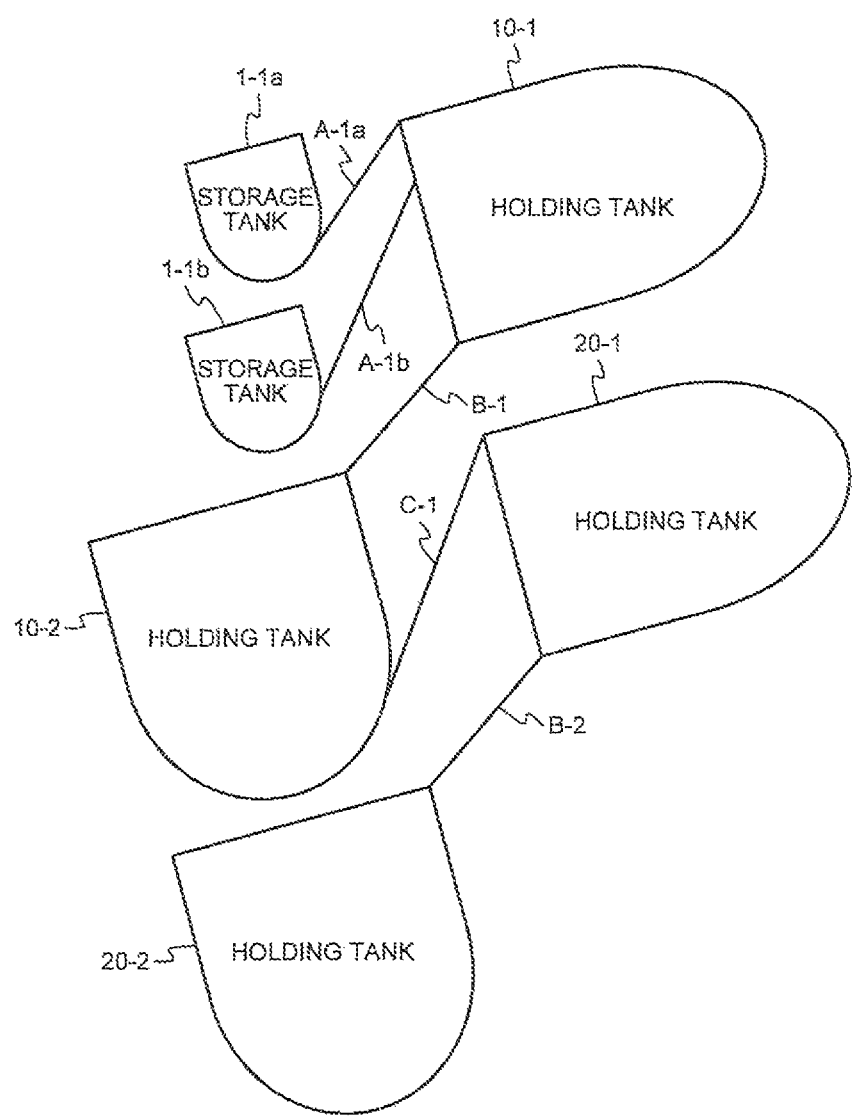
Figures 2, 22:
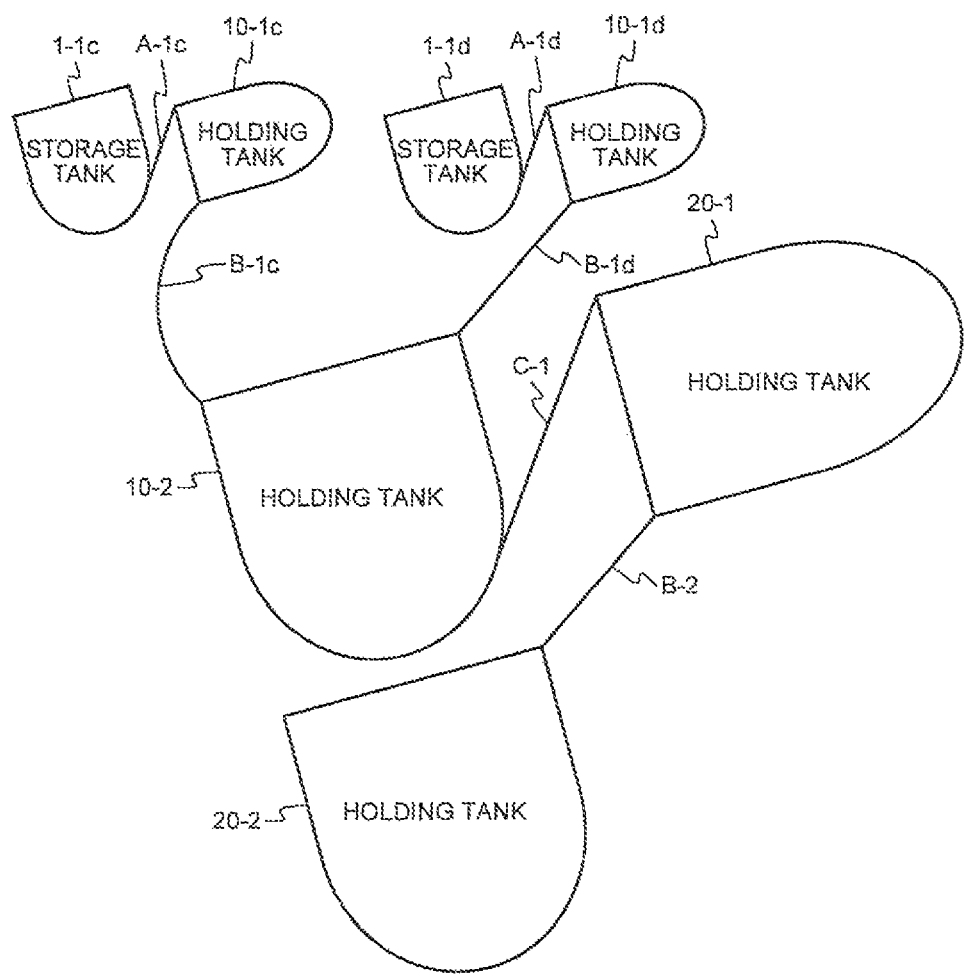

Examples of "connected to a storage tank and/or holding tank on a higher level than that holding tank via a plurality of channels" may include the following configurations. First, when "that holding tank" is a first holding tank, this holding tank needs to be connected to at least one first storage tank as described above. However, a configuration in which "that holding tank" is connected to two or more first storage tanks via a plurality of channels corresponds to "connected to a storage tank and/or holding tank on a higher level than that holding tank via a plurality of channels." Further, a configuration in which, in addition to a first storage tank, "that holding tank" is connected to a storage tank and a holding tank selected from among holding tanks in higher-level units and optionally-provided second storage tanks via channels also corresponds to "connected to a storage tank and/or holding tank on a higher level than that holding tank via a plurality of channels." More specifically, as illustrated in FIG. 22-1, two first storage tanks 1-1$a$ and 1-1$b$ can be connected to the first holding tank 10-1 via channels A-1$a$ and A-1$b$. Such a configuration allows the specimen/reagents in the two first storage tanks to be simultaneously mixed in the first holding tank.

On the other hand, when "that holding tank" is a second holding tank, this holding tank needs to be connected to at least one first holding tank as described above. However, a configuration in which "that holding tank" is connected to two or more first holding tanks via a plurality of channels corresponds to "connected to a storage tank and/or holding tank on a higher level than that holding tank via a plurality of channels." Further, a configuration in which, in addition to a first holding tank, "that holding tank" is connected to a first storage tank, a second storage tank, and a first holding tank in the same unit, and is also connected to two or more storage tanks and holding tanks selected from among holding tanks and optionally-provided second storage tanks in higher-level units also corresponds to "connected to a storage tank and/or holding tank on a higher level than that holding tank via a plurality of channels." More specifically, as illustrated in FIG. 22-2, two first holding tanks 10-1c and 10-1d can be connected to the second holding tank 10-2 via channels B-1c and B-1d. The first holding tanks 10-1c and 10-1d are connected to first storage tanks 1-1c and 1-1d via channels A-1c and A-1d, respectively. In this example, the specimen/reagents in the two first storage tanks can be separately stirred in the first storage tanks, and then the resultant mixtures are mixed in a second holding tank.

Although the specimen/reagent in the present invention is as described above, the specimen/reagent preferably includes at least one reagent selected from a labeled antibody, a washing solution, a substrate, a hydrogen peroxide solution, and a diluent. In such a case, a reagent which is commonly used in antigen-antibody reactions and which needs to be sequentially reacted, can be by sequentially fed and reacted using the liquid-feeding chip according to the present invention.

Furthermore, the specimen/reagent in the present invention may be an enzyme, a nucleic acid and the like. A specimen and a plurality of reagents may be continuously mixed or mixed in advance, and fed to the reaction chamber for nucleic acid amplification and detection.

It is preferred that the inner wall of at least one storage tank, holding tank, or channel of the storage tanks, holding tanks, and channels in the liquid-feeding chip according to the present invention have been subjected to an adsorption suppression treatment. This allows errors in measurement, analysis, and reaction caused by reduction in the component concentration due to adsorption of the specimen and the reagent to be reduced, so that accuracy can be improved. Furthermore, the liquid may stagnate if the specimen/reagent contained in a storage tank is adsorbed by the inner wall. However, by carrying out an adsorption suppression treatment, this problem can be resolved. Examples of methods for the adsorption suppression treatment which can be used include a coating treatment in which a hydrophilic polymer material is adsorbed on a surface by static electricity, and a method in which a hydrophilic polymer material is covalently bonded to the surface of the resin and tightly secured by irradiating a high-energy beam.

It is preferred that at least one from among the first storage tank, second storage tank, first holding tank, second holding tank, waste tank, and reaction chamber (reaction tank) have an air channel or an air hole for depressurizing. The air pressure in the storage tanks changes when the specimen/reagent is contained, which can lead to a reduction in the feeding efficiency of the liquid-feeding chip, or even damage to the liquid-feeding chip. Thus, by having an air channel, the air pressure in the storage tanks can be maintained at a constant level, whereby such risks can be avoided. Furthermore, having an air channel also allows the specimen/reagent to be introduced via the air channel into a first storage tank, first holding tank, and second holding tank.

The position and the angle of the air channel is not specifically limited. However, to prevent the specimen/reagent from flowing in during liquid feeding, it is preferred that the air channel extend and be open in the axis of rotation direction (inner circumferential side) from the respective storage tanks The shape and the size of the air channel are not specifically limited, as long as the overall channel has a tube shape. The whole air channel does not have to have the same shape. The shape of the transverse cross-section of the air channel is not specifically limited to a circle, a polygon or the like. The size of the transverse cross-section of the air channel also does not have to be fixed, and may be appropriately adjusted to a size through which the specimen/reagent can pass. For example, the short diameter (for a circle, this means the radius, and for a polygon, this means the shortest diameter passing through the center) of the air channel is usually in the range of 0.1 to 5.0 mm, and preferably in the range of 0.5 to 2.0 mm.

2. Analysis Method According to the Present Invention

The analysis method of a specimen according to the present invention includes the steps of introducing a specimen/reagent into at least one storage tank of the liquid-feeding chip, then rotating the liquid-feeding chip about an axis of rotation external to the liquid-feeding chip at a first rotation speed, and rotating at a second rotation speed which is slower than the first rotation speed or stopping rotation.

Figure 5:
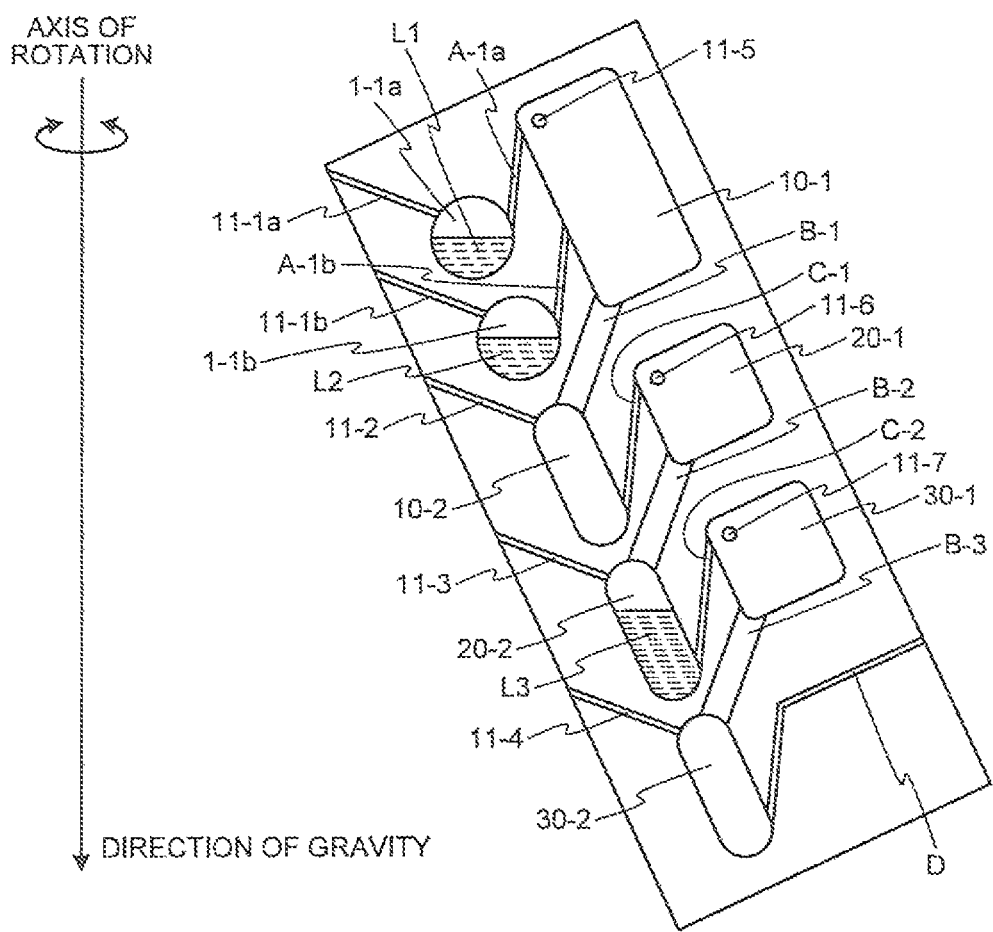
FIG. 5 is a diagram illustrating a state of a liquid-feeding chip in an analysis method according to the present invention.
Figure 6:
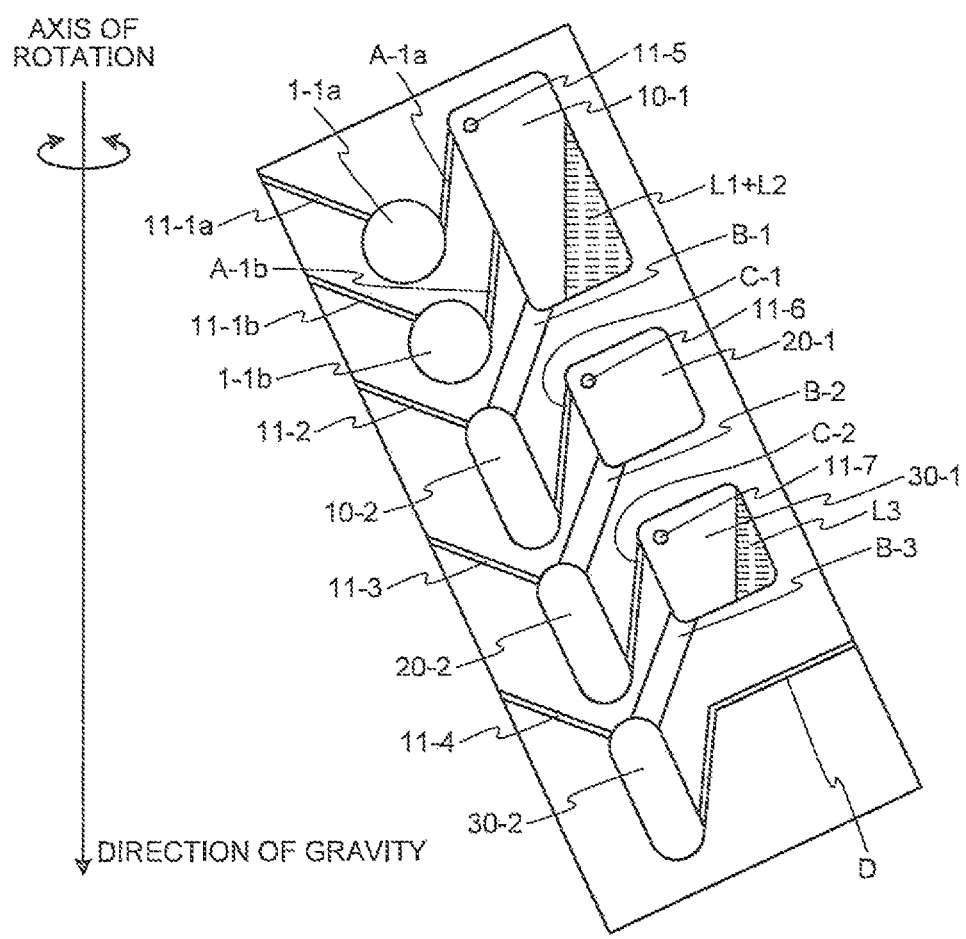
FIG. 6 is a diagram illustrating a state of a liquid-feeding chip in an analysis method according to the present invention.
Figure 7:
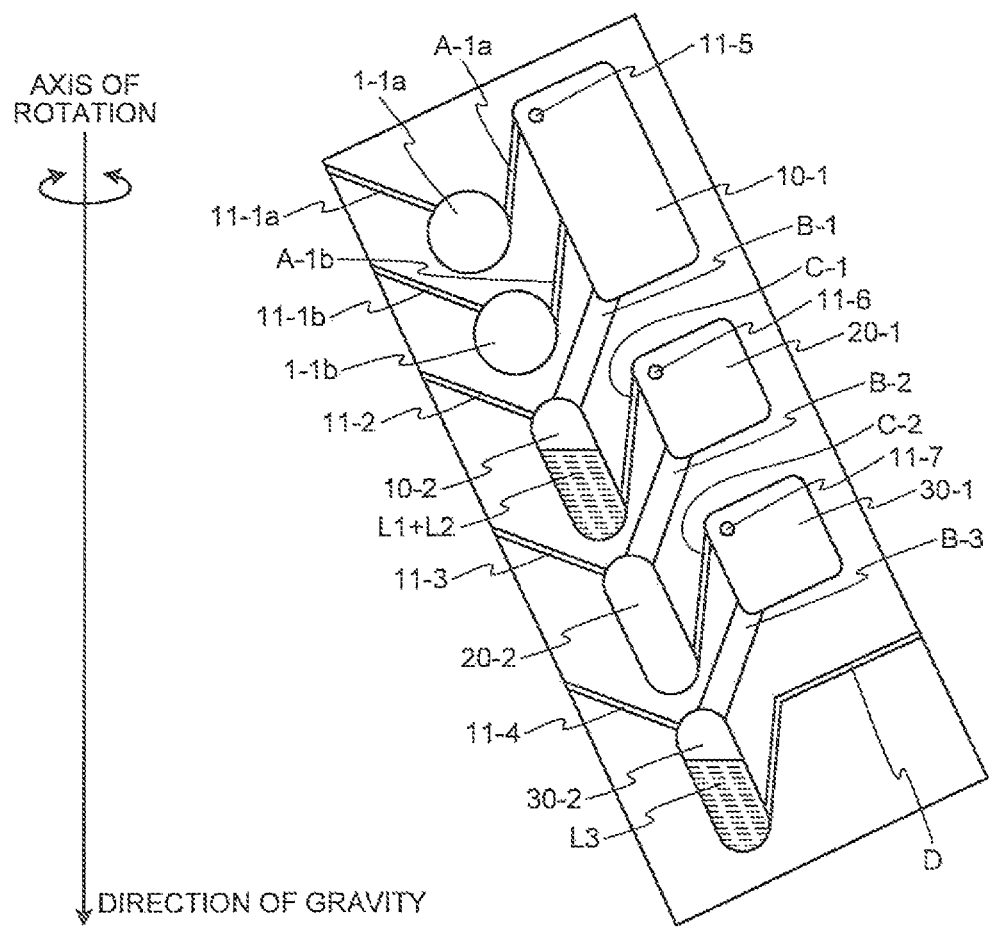
FIG. 7 is a diagram illustrating a state of a liquid-feeding chip in an analysis method according to the present invention.

FIGS. 5 to 7 illustrate the movement of the specimen/reagent during analysis using the liquid-feeding chip of examples according to the present invention.

Figures 1, 23:
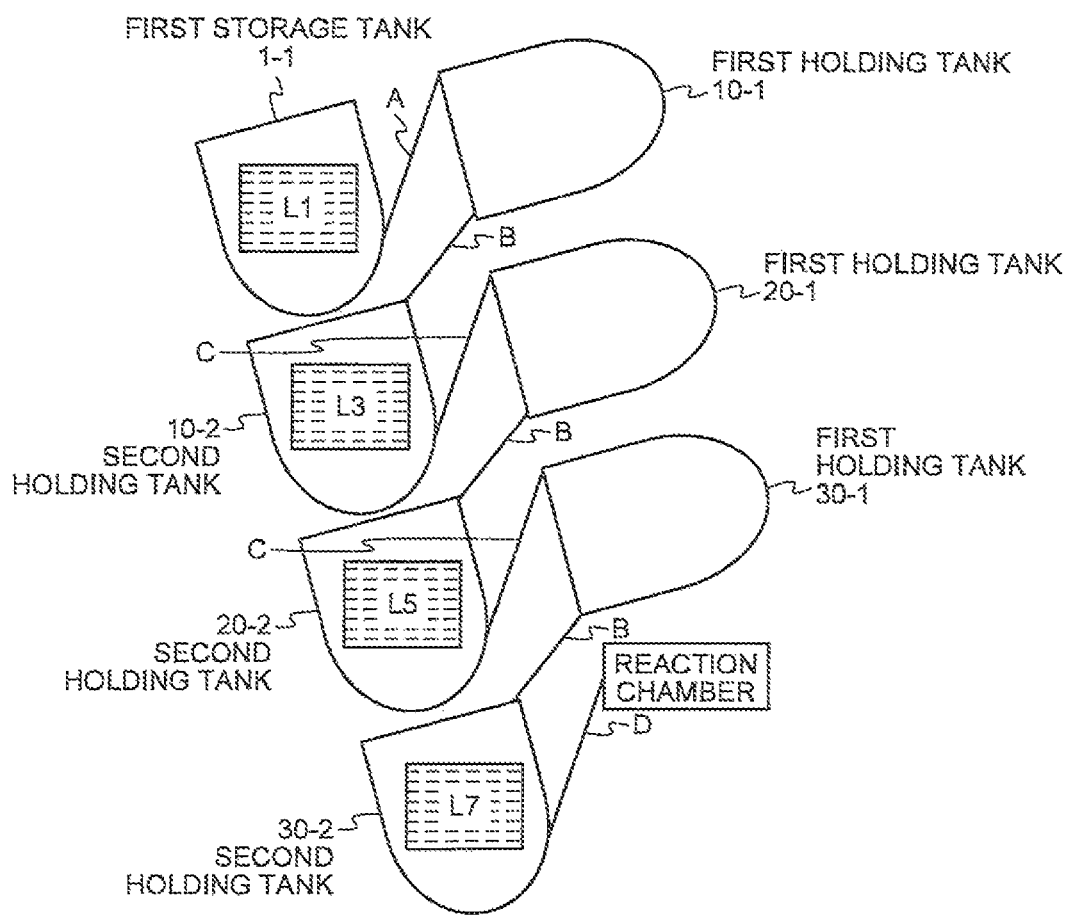
Figures 2, 23:
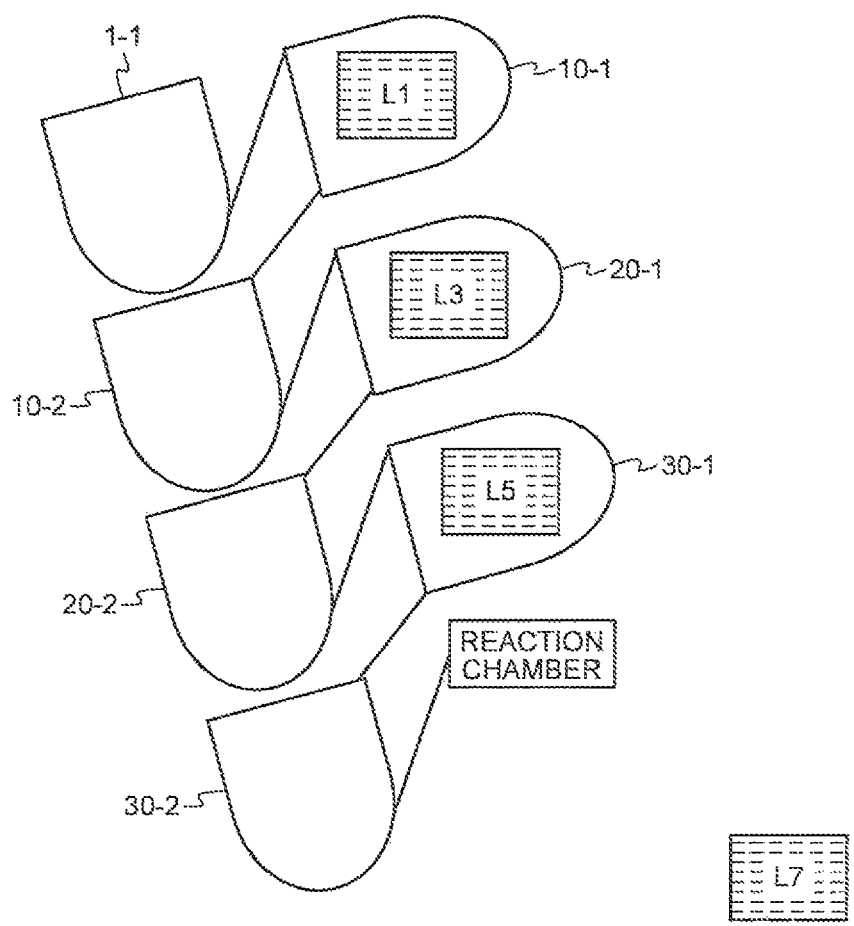
Figures 3, 23:
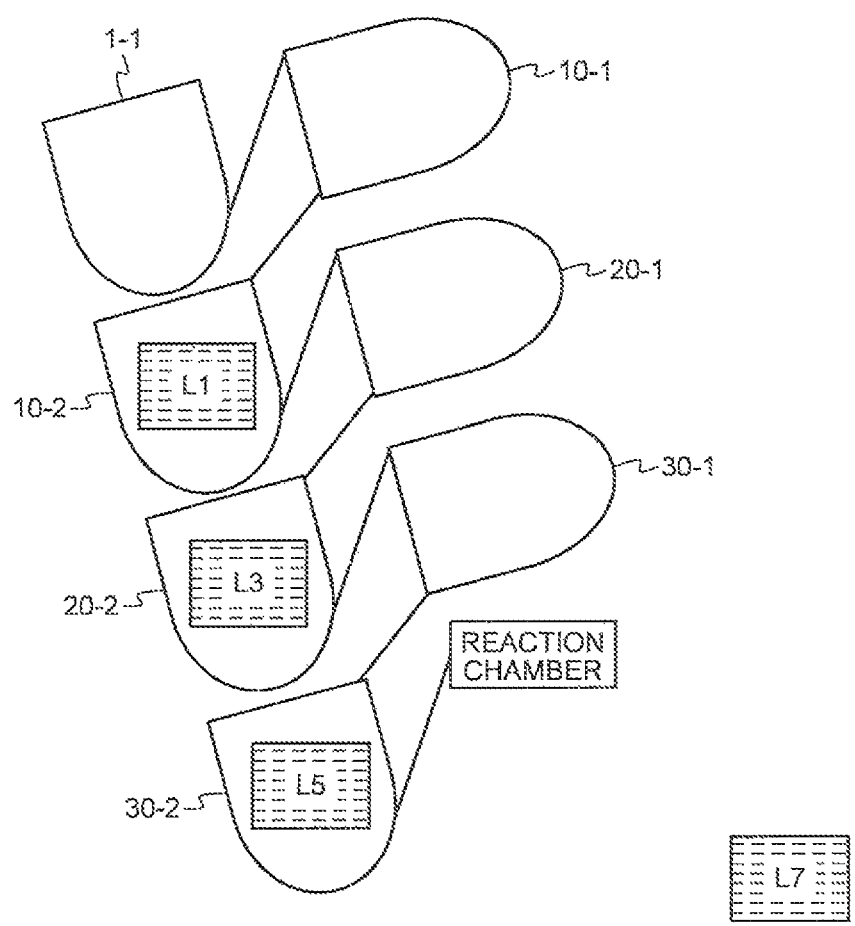
Figures 4, 23:
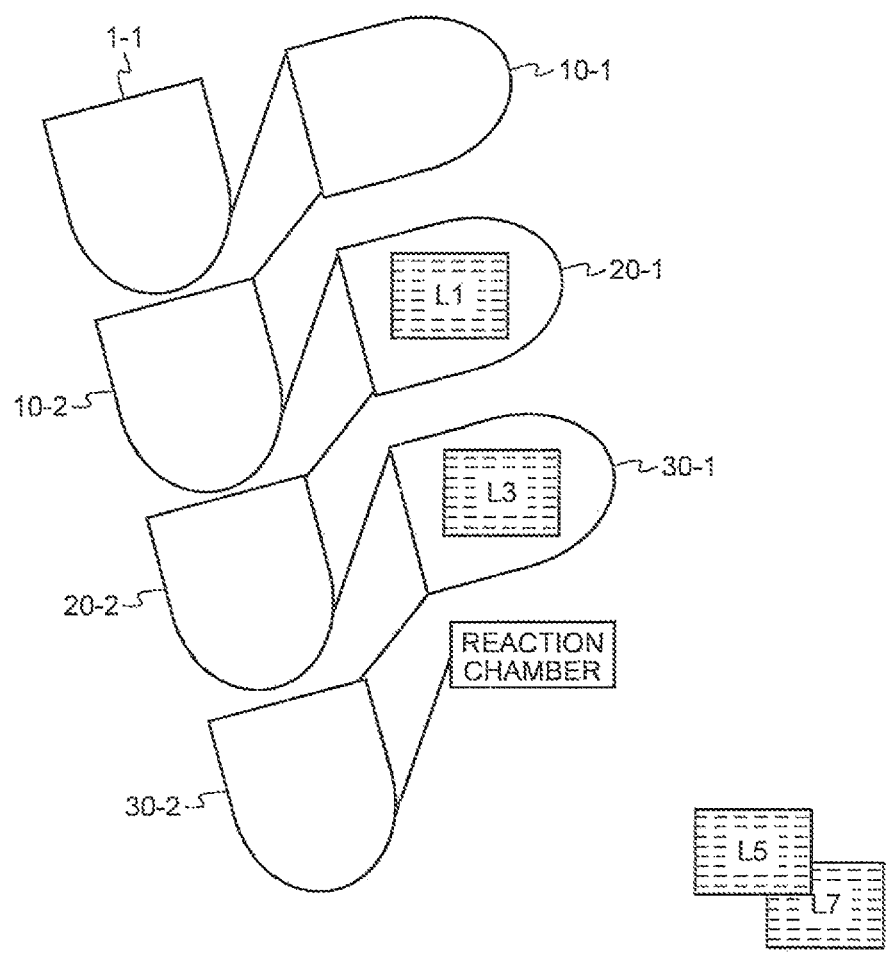
Figures 5, 23:
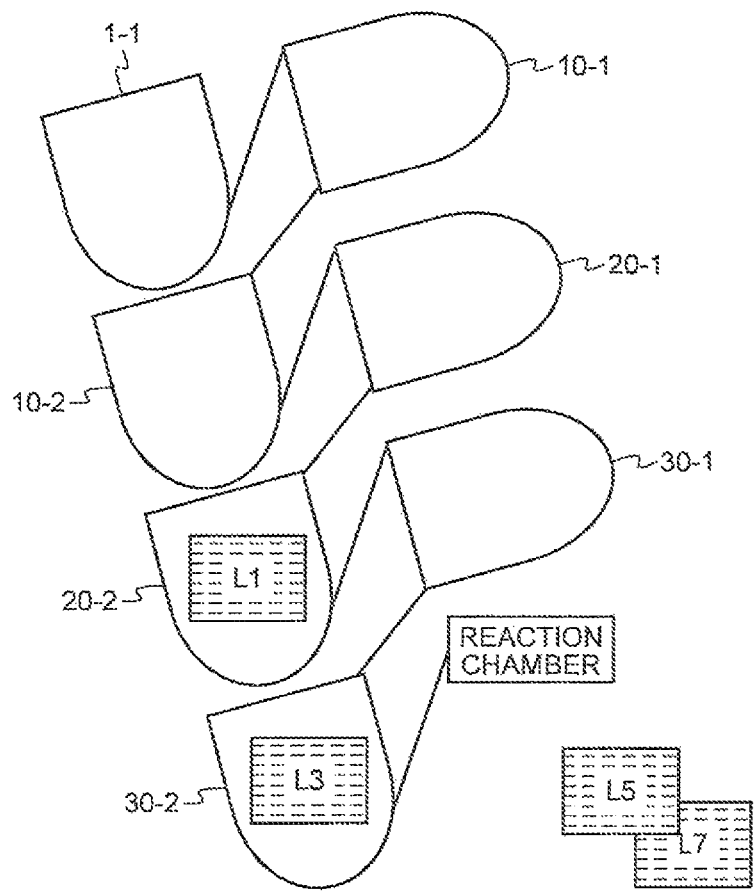
Figures 6, 23:
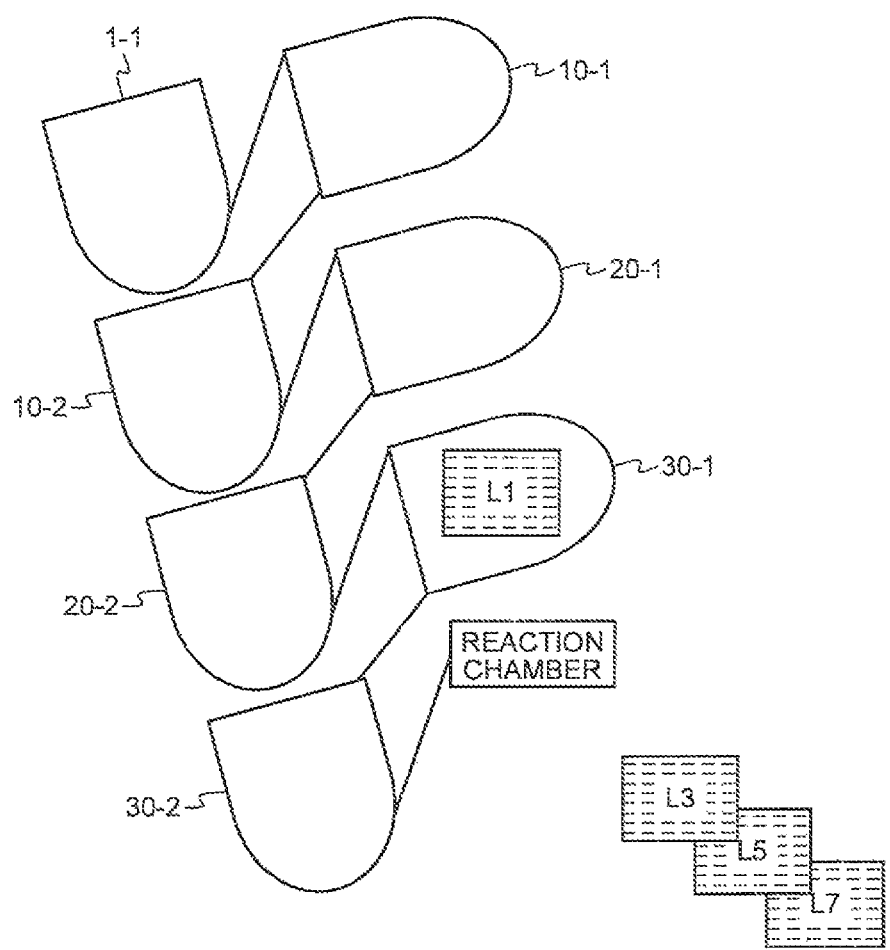
Figures 7, 23:
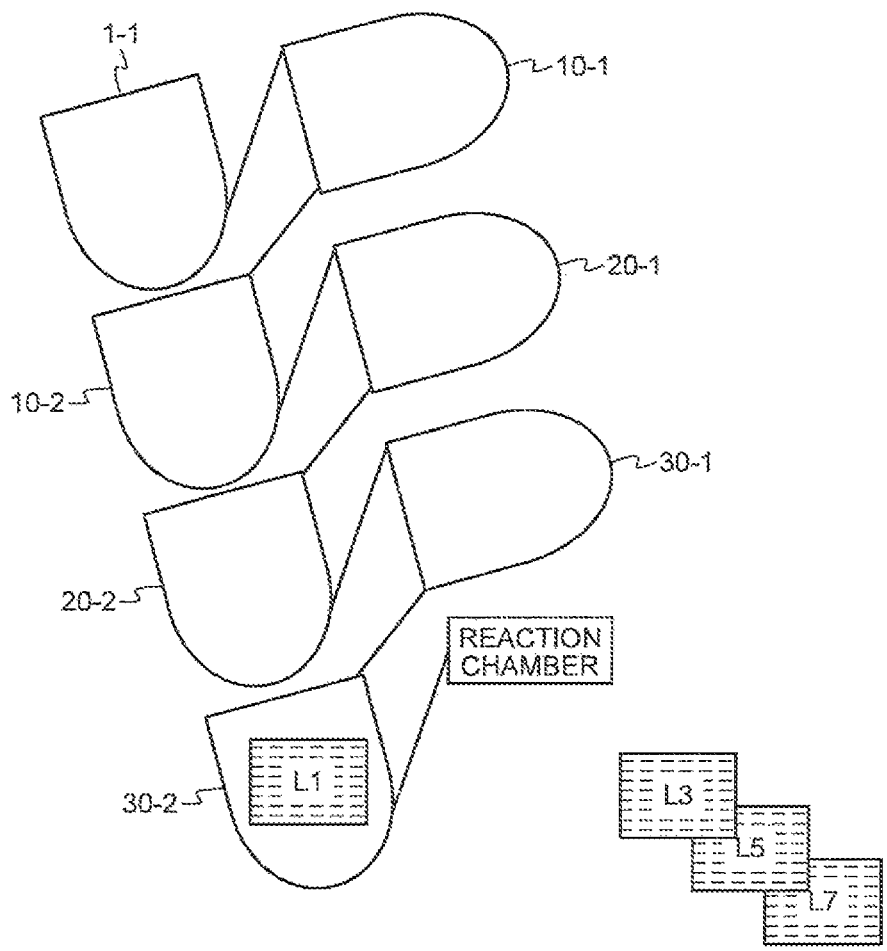
Figures 8, 23:
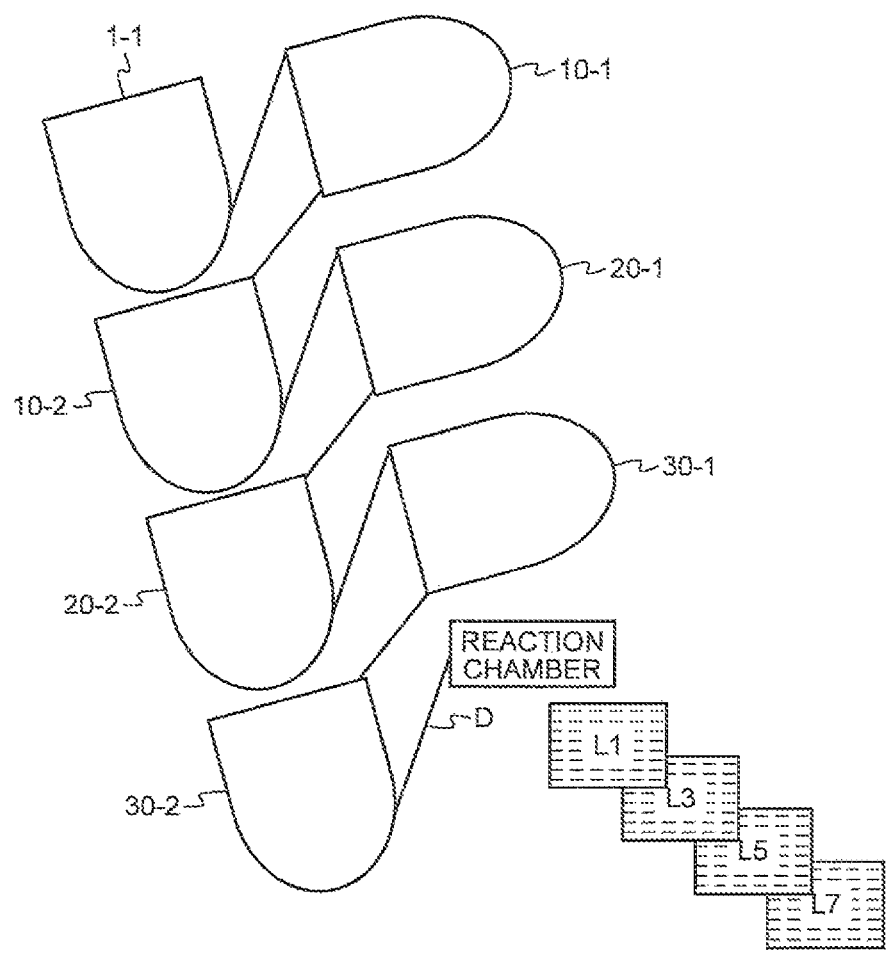

FIGS. 23-1 to 23-8 illustrate the movement of the specimen/reagent in the liquid-feeding chip according to the present invention.

Each of these figures is shown having an axis of rotation on the left side when the main surface of the liquid-feeding chip is viewed from the front. More specifically, each of these figures illustrates a state viewed from a circumferential direction of the orbit when the axis of rotation in an approximately perpendicular direction is positioned on the left side of the liquid-feeding chip when it is rotated. The direction facing the left side of the liquid-feeding chip on the paper face is the axis of rotation direction (inner circumferential side). The direction facing the right side of the liquid-feeding chip on the paper face is the outer circumferential side, which is also the centrifugal force direction. In addition, downwards is the direction of gravity (approximately perpendicular direction).

Preferably, the analysis method of the specimen in the present invention includes a step of introducing a specimen/reagent into at least one storage tank or holding tank of the liquid-feeding chip and repeating at least twice or more the steps of rotating the liquid-feeding chip about an axis of rotation external to the liquid-feeding chip at a first rotation speed, and rotating at a second rotation speed which is slower than the first rotation speed or stopping rotation.

For example, suppose the case in which a liquid-feeding chip has two liquid-feeding units each formed from a first holding tank, a second holding tank, and a channel B connecting them, and a first storage tank being in communication with the first holding tank by a channel A, with a channel D being connected to the second holding tank of the lower level liquid-feeding unit. In this case, when two types of specimen/reagent are introduced and contained in the first storage tank and the second holding tank of the lower level liquid-feeding unit, the specimen/reagent contained in the first storage tank flows to and is held in the first holding tank during rotation at a first rotation speed. The specimen/reagent contained in advance in the second holding tank of the lower level liquid-feeding unit flows out from the channel D. Further, the specimen/reagent held in the first holding tank of the upper level liquid-feeding unit moves to the second holding tank by rotating at a second rotation speed which is slower than the first rotation speed, or by stopping rotation. In addition, the specimen/reagent held in the second holding tank is moved to the first holding tank of the lower level liquid-feeding unit by rotating at the first rotation speed. By repeating these steps, a plurality of different specimen/reagents can be sequentially fed.

For example, suppose the case in which a liquid-feeding chip has two liquid-feeding units each formed from a first holding tank, a second holding tank, and a channel B connecting them, and a first storage tank being in communication with the first holding tank by a channel A. In this case, when two types of specimen/reagent are introduced and contained in the first storage tank and the second holding tank of a first level liquid-feeding unit, the specimen/reagent contained in the first storage tank flows to and is held in the first holding tank during rotation at a first rotation speed. The specimen/reagent contained in advance in the second holding tank of the first level liquid-feeding unit is fed to the first holding tank of a second level liquid-feeding unit via a channel C. Further, the specimen/reagent held in the first holding tank of the first level liquid-feeding unit is fed to the second holding tank of the first level unit by rotating at a second rotation speed which is slower than the first rotation speed, or by stopping rotation. In addition, the specimen/reagent held in the first holding tank of the second level liquid-feeding unit is fed to the second holding tank of the second level liquid-feeding unit. Moreover, by rotating at the first rotation speed, the specimen/reagent held in the second holding tank of the first level liquid-feeding unit is fed to the first holding tank of a lower level liquid-feeding unit, and the specimen/reagent held in the second holding tank of the second level unit is discharged via a channel D. Still further, by repeating the rotation at a second rotation speed or the stopping of rotation and the rotation at the first rotation speed, the remaining one specimen/reagent is discharged via the channel D. Therefore, using only centrifugal force and gravity as a driving force, a plurality of specimen/reagents can be sequentially fed through the tanks The analysis method according to the present invention will now be described based on FIGS. 23-1 to 23-8. In the example illustrated in FIG. 23-1, before rotation, respective liquids (specimen/reagents) L1, L3, L5, and L7 are contained in advance in a first storage tank 1-1 and second holding tanks 10-2, 20-2, and 30-2.

As illustrated in FIG. 23-2, if the liquid-feeding chip is first rotated at the first rotation speed, the specimen/reagents L1, L3, and L5 are fed to the first holding tanks 10-1, 20-1, and 30-1, respectively, and the specimen/reagent L7 reacts in the reaction chamber and is then discharged.

Next, as illustrated in FIG. 23-3, if the liquid-feeding chip is rotated at the second rotation speed or if rotation is stopped, the specimen/reagents L1, L3, and L5 are fed to the second holding tanks 10-2, 20-2, and 30-2, respectively.

As illustrated in FIG. 23-4, if the liquid-feeding chip is then again rotated at the first rotation speed, the specimen/reagents L1 and L3 are fed to the first holding tanks 20-1 and 30-1 of the next level liquid-feeding unit, respectively, and the specimen/reagent L5 reacts in the reaction chamber and is then discharged.

As illustrated in FIG. 23-5, if the liquid-feeding chip is then rotated at the second rotation speed or if rotation is stopped, the specimen/reagents L1 and L3 are fed to the second holding tanks 20-2 and 30-2, respectively.

Next, as illustrated in FIG. 23-6, if the liquid-feeding chip is again rotated at the first rotation speed, the specimen/reagent L1 is fed to the first holding tank 30-1 of the still next level liquid-feeding unit, and the specimen/reagent L3 reacts in the reaction chamber and is then discharged.

As illustrated in FIG. 23-7, if the liquid-feeding chip is then rotated at the second rotation speed or if rotation is stopped, the specimen/reagent L1 is fed to the second holding tank 30-2.

Subsequently, as illustrated in FIG. 23-8, if the liquid-feeding chip is again rotated at the first rotation speed, the specimen/reagent L1 reacts in the reaction chamber and is then discharged. In this example, all of the specimen/reagents were sequentially fed to the reaction chamber and discharged from the liquid-feeding chip over 4 cycles.

The first rotation speed in the present invention may be a specific rotation speed, or may be a continuously changing rotation speed. In particular, the first rotation speed may be any speed as long as it is faster than the speed at which the liquid can be fed to the next holding tank or the reaction tank via the channels A, C, D, or E.

The second rotation speed in the present invention may be a specific rotation speed, or may be a continuously changing rotation speed. In particular, the second rotation speed may be any speed as long as it is slower than the speed at which the liquid can be fed to the next holding tank via the channel B of a liquid-feeding unit at each level.

3. Feeding Method

The liquid-feeding chip according to the present invention can be utilized in a liquid feeding method. An example of the feeding method according to the present invention will now be described.

First, a liquid-feeding chip having the above-described configuration is prepared. Next, a liquid is introduced into a storage tank of the liquid-feeding chip.

Then, the liquid-feeding chip into which the liquid was introduced is mounted on a rotation apparatus. The liquid-feeding chip is rotated at the above-described first rotation speed, so that the liquid is fed to a first holding tank by utilizing centrifugal force.

Subsequently, (a) the liquid-feeding chip is rotated at a second rotation speed, which is slower than the first rotation speed, or rotation is stopped, so that the liquid is fed to a second holding tank by utilizing gravity.

Further, (b) the liquid-feeding chip is rotated at the first rotation speed, so that the liquid is fed to a lower level first holding tank.

In addition, the steps (a) and (b) may be carried out once or repeated twice or more. Step (a) may be set as the final step so that the liquid is ultimately held in the second holding tank. Further, step (b) may be set as the final step, and the liquid can be moved out of the liquid-feeding chip using a separate channel.

According to the feeding method of the present invention, a liquid can be fed to a desired tank in a liquid-feeding chip by utilizing centrifugal force and gravity. Therefore, for example, preparation such as stirring and mixing, or reactions among a plurality of types of liquid can be carried out in an arbitrary tank.

4. Specific Examples and Usage Examples of the Liquid-Feeding Chip According to the Present Invention Specific examples and usage examples of the liquid-feeding chip according to the present invention will now be described with reference to the drawings.

As illustrated in FIG. 1, a liquid-feeding chip is composed of a first level liquid-feeding unit U-1, a lower level liquid-feeding unit (second level liquid-feeding unit) U-2, and a lowest level liquid-feeding unit (third level liquid-feeding unit) U-3. In the liquid-feeding chip illustrated in FIG. 1, a first storage tank 1-1 is arranged on an inner circumferential side (left side: axis of rotation side) of the liquid-feeding unit U-1. This first storage tank 1-1 is connected to a first holding tank 10-1 of the first level liquid-feeding unit U-1 via a channel A-1. The first level liquid-feeding unit U-1 is composed of the first holding tank 10-1, a channel B-1, and a second holding tank 10-2. The first holding tank 10-1 and the second holding tank 10-2 are connected by the channel B-1. The second holding tank 10-2 is connected to a first holding tank 20-1 of the lower level liquid-feeding unit (second level liquid-feeding unit) U-2 via a channel C-1. The second level liquid-feeding unit U-2 is composed of the first holding tank 20-1, a channel B-2, and a second holding tank 20-2. The first holding tank 20-1 and the second holding tank 20-2 are connected by the channel B-2. The second holding tank 20-2 is connected to a first holding tank 30-1 of the third level liquid-feeding unit U-3 via a channel C-2. The third level liquid-feeding unit U-3 includes the first holding tank 30-1, a channel B-3, and a second holding tank 30-2. The first holding tank 30-1 and the second holding tank 30-2 are connected by the channel B-3. A channel D is provided in the third level liquid-feeding unit U-3, and is connected to the second holding tank 30-2 as an outlet channel.

As illustrated in FIG. 1, the first storage tank 1-1, the second holding tank 10-2 of the upper level liquid-feeding unit, and the second holding tank 20-2 of the third level liquid-feeding unit are positioned on the inner circumferential side, namely the axis of rotation side of the liquid-feeding chip, of the first holding tank 10-1 of the upper level liquid-feeding unit, the first holding tank 20-1 of the lower level liquid-feeding unit, and the first holding tank 30-1 of the third level liquid-feeding unit, respectively. The channel A-1 extends in an upwards incline from a bottom portion of the first storage tank 1-1, and is connected to an upper portion of the first holding tank 10-1.

As illustrated in FIG. 1, the channel C-1 connects the liquid-feeding unit U-1 and the liquid-feeding unit U-2, and the channel C-2 connects the liquid-feeding unit U-2 and the liquid-feeding unit U-3. More specifically, the channel C-1 extends from a bottom portion of the second holding tank 10-2 of the liquid-feeding unit U-1 upwards in an outer circumferential direction, and opens onto an upper portion of the first holding tank 20-1 of the liquid-feeding unit U-2. The channel C-2 extends from a bottom portion of the second holding tank 20-2 of the liquid-feeding unit U-2 upwards in an outer circumferential direction, and opens onto an upper portion of the first holding tank 30-1 of the liquid-feeding unit U-3. The channel D is connected to a lower portion of the second holding tank 30-2 of the liquid-feeding unit U-3, and liquid is discharged from the liquid-feeding unit.

On the other hand, although generally the same as the example illustrated in FIG. 1, the example illustrated in FIG. 2 is different in having two first storage tanks 1-1a and 1-1b connected to the first level liquid-feeding unit U-1. The first storage tanks 1-1a and 1-1b are connected to the first holding tank 10-1 by channels A-1a and A-2b, respectively. The incline of the channels A-1a and A-2b is generally the same. Although the first storage tanks 1-1a and 1-1b have a circular shape, their shapes are not specifically limited as long as liquid can smoothly flow out by centrifugal force from the channels A-1a and A-2b. Examples of other shapes include a conical, pyramid, spherical and the like shape. With such a configuration, a specimen/reagent contained in advance in the two first storage tanks 1-1a and 1-1b can be mixed in the first holding tank 10-1 by rotation at the first rotation speed.

In the liquid-feeding chip illustrated in FIGS. 1 and 2, the second holding tank 30-2 of the third level liquid-feeding unit U-3 is connected from the first holding tank 30-1 of the liquid-feeding unit U-3 by the channel B-3 which extends toward the direction of gravity and the axis of rotation (inner circumferential side). Further, the channels B-1, B-2, and B-3 are wider than the channels A-1, C-1, and C-2, and have a smaller incline with respect to the axis of rotation. In addition, the channel D connected to the second holding tank 30-2 of the third level liquid-feeding unit U-3 extends from the axis of rotation toward the distant side (outer circumferential side). The channel D extends in an upwards incline until a midpoint along the channel, then extends in a perpendicular direction with respect to the axis of rotation and opens onto the exterior. The channel D has a width which is about the same as that of the channel A-1.

In the example illustrated in FIG. 1, the first storage tank 1-1 and the second holding tanks 10-2, 20-2, and 30-2 are respectively provided with air channels 11-1 to 11-4. Furthermore, in the example illustrated in FIG. 2 too, the first storage tanks 1-1a and 1-1b are provided with air channels 11-1a and 11-1b, and the second holding tanks 10-2, 20-2, and 30-2 are provided with air channels 11-2 to 11-4, respectively. Each of these air channels extends upwards on the axis of rotation side from an upper portion of the storage tank, and opens onto the exterior. In addition, the first holding tanks 10-1, 20-1, and 30-1 are provided with air holes 11-5, 11-6, and 11-7, respectively.

The example illustrated in FIG. 3 is the same as the example illustrated in FIG. 1 in terms of the configuration of the internal tanks and channels, but differs in terms of the size and shape of these parts.

Specifically, the first storage tank 1-1 has an circular profile when viewed from a main surface side thereof. Profiles of the second holding tank 10-2 of the upper level liquid-feeding unit U-1, the second holding tank 20-2 of the lower level liquid-feeding unit U-2, and the second holding tank 30-2 of the lowest level liquid-feeding unit when viewed from a main surface side thereof are a quadrilateral protruding out in the outer circumferential direction. Profiles of the first holding tank 10-1 of the upper level liquid-feeding unit U-1, the first holding tank 20-1 of the lower level liquid-feeding unit U-2, and the first holding tank 30-1 of the lowest level liquid-feeding unit when viewed from the main surface side thereof have a swollen capsule-shape in which a quadrilateral extends out along both sides in the axis of rotation direction.

Furthermore, in the example illustrated in FIG. 3, the channel A-1 is slightly inclined near the first holding tank 10-1 in the direction of gravity. The channels B-1, B-2, and B-3 extend toward the axis of rotation direction at the respective connecting portions (origin) on the first holding tanks 10-1, 20-1, and 30-1. However, near the second holding tanks 10-2, 20-2, and 30-2 where they each connect, the channels B-1, B-2, and B-3 switch to a direction of gravity direction. The channel D extends in a straight line in the outer circumferential direction with respect to the axis of rotation. The air channels 11-1, 11-2, 11-3 and 11-4 extend toward the outer circumferential side from an aperture of the liquid-feeding chip on the inner circumferential side, switch to the direction of gravity midway along, and open into the first storage tank 1-1 and the second holding tanks 10-2 and 20-2 and the second holding tank 30-2 to which each of these air channels is respectively connected.

In addition to the channels A-1 and D illustrated in FIG. 3, the air channels 11-1, 11-2, 11-3 and 11-4 have an aperture diameter which is larger than each of those illustrated in FIG. 1. Moreover, in this example, as described above, inner wall portions C-11 and C-21 of the second holding tank play the role of the channel C. Furthermore, an inner wall portion D-11 of the second holding tank constitutes part of the channel D.

The example illustrated in FIG. 4 is different from the example illustrated in FIG. 1 in further having second storage tanks 10-3, 20-3, and 30-3 in the liquid-feeding units U-1, U-2, and U-3, respectively. The second storage tanks 10-3, 20-3, and 30-3 are connected to the second holding tanks 10-2, 20-2, and 30-2 by channels E-1, E-2, and E-3, respectively. Furthermore, in the example illustrated in FIG. 4, a reaction chamber 40 is provided midway along the channel D, and the channel D is ultimately connected to a waste tank 50.

Examples of the analysis method according to the present invention will now be described while referring to FIGS. 5, 6 and 7. FIGS. 5, 6 and 7 illustrate the liquid feeding principles of the liquid-feeding chip according to the present invention using the liquid-feeding chip illustrated in FIG. 2 as an example.

FIG. 5 illustrates a state in which specimen/reagents L1, L2, and L3 are filled (stopped state). FIG. 6 illustrates a state in which the liquid-feeding chip is being rotated at a first rotation speed. FIG. 7 illustrates a state in which the liquid-feeding chip is being rotated at a second rotation speed or rotation is stopped.

As illustrated in FIG. 5, the specimen/reagents L1, L2, and L3 are introduced into a first storage tank 1-1a, a first storage tank 1-1b, and a second holding tank 20-2 of a second level liquid-feeding unit U-2, respectively. Then, if the liquid-feeding chip is rotated at a first rotation speed, the specimen/reagents L1, L2, and L3 rise up channels A-1a, A-1b, and C-2 by the action of centrifugal force and gravity, respectively. The specimen/reagents L1 and L2 reach a first holding tank 10-1 of a first level unit U-1, and the specimen/reagent L3 reaches a first holding tank 30-1 of a third level unit U-3. More specifically, as illustrated in FIG. 6, the specimen/reagents L1 and L2 are both carried to the first holding tank 10-1 of the first level liquid-feeding unit U-1, where they are mixed. Furthermore, the specimen/reagent L3 is carried to the first holding tank 30-1 of the third level liquid-feeding unit U-3.

At this stage, to feed the specimen/reagents L1, L2, and L3 to the respective next tanks at the same first rotation speed, the angle formed by the channel A-1a and the axis of rotation, the angle formed by the channel A-1b and the axis of rotation, and the angle formed by the channel C-2 and the axis of rotation may be set to be the same. Alternatively, the first rotation speed may be set to be sufficiently faster than the rotation speed at which liquid starts to flow through the channels A-1a, A-1b, and C-2. The centrifugal force acting on the liquid-feeding chip during rotation is inversely proportional to the distance between the axis of rotation and the liquid-feeding chip, and proportional to the square of the rotation speed. Generally, for a body with a mass m at a velocity v at a position r from the axis of rotation, the centrifugal force acting during rotation is represented as $F=mv^2/r$.

During the rotation of the liquid-feeding chip at the first rotation speed, the target for the centrifugal force acting on the liquid-feeding chip is as described above. Furthermore, the rotation time at the first rotation speed may usually be set to 0.01 to 10 minutes, and preferably 0.05 to 2 minutes.

As illustrated in FIG. 7, if the liquid-feeding chip is further rotated at the second rotation speed, or if rotation is stopped, the mixture of the specimen/reagents L1 and L2 enters the channel B-1 from the first holding tank 10-1 of the first level unit U-1, and is stored in the second holding tank 10-2. Further, the specimen/reagent L3 passes from the first holding tank 30-1 of the third level unit U-3, through the channel B-3, and is fed to the second holding tank 30-2.

At this stage, to feed the specimen/reagents L1, 12, and L3 to the respective next tanks at the same second rotation speed, the angle formed by the channel B-1 and the axis of rotation and the angle formed by the channel B-3 and the axis of rotation may be set to be the same. Alternatively, the second rotation speed may be set to be sufficiently slower than the rotation speed at which liquid starts to flow through the channels B-1 and B-3.

During the rotation of the liquid-feeding chip at the second rotation speed, the target for the centrifugal force acting on the liquid-feeding chip is as described above. Furthermore, the rotation time at the second rotation speed, or the period for which rotation is stopped, may usually be set to 0.01 to 10 minutes, and preferably 0.05 to 2 minutes.

Thus, by repeating rotation at a first rotation speed and rotation at a second rotation speed or stopping rotation, a specimen/reagent can be sequentially fed to the next storage tank or holding tank, thereby enabling specimen/reagents to be sequentially mixed and sequentially reacted.

In the analysis method according to the present invention, first, a specimen/reagent is introduced into a storage tank or a specimen/reagent reservoir of the liquid-feeding chip. The specimen/reagent may be introduced by an ordinary method, such as by using a pipette for example. The storage tank or specimen/reagent reservoir into which the specimen/reagent is introduced may be selected as appropriate. The specimen/reagent may be introduced into at least any one of the storage tanks or specimen/reagent reservoirs in the liquid-feeding chip. The specimen/reagent does not have to be introduced into all of them.

The liquid-feeding chip according to the present invention can be used in the amplification and detection of a nucleic acid.

Figure 24:
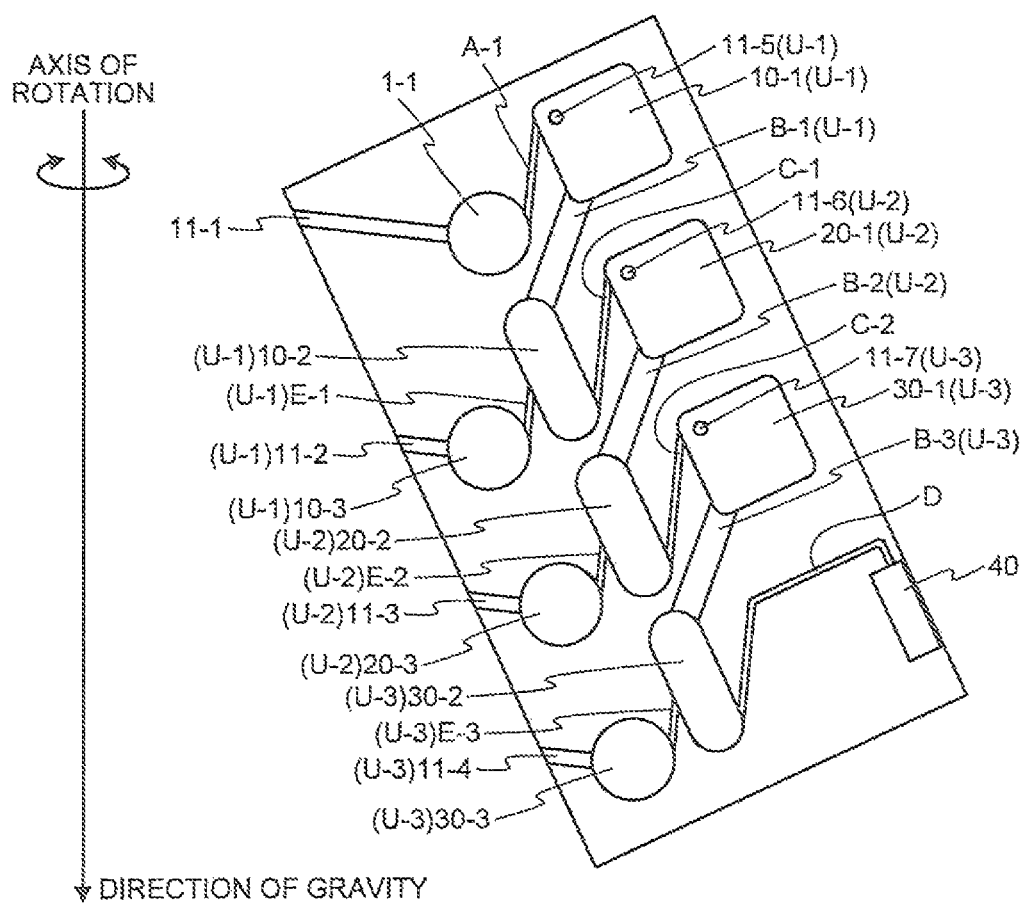
FIG. 24 is a plan view illustrating another example of the liquid-feeding chip according to the present invention.

An example of nucleic acid amplification using the liquid-feeding chip according to the present invention will now be described with reference to FIG. 24. FIG. 24 is a plan view illustrating an example of the liquid-feeding chip according to the present invention as viewed from a main surface of the liquid-feeding chip. A nucleic acid amplification reaction solution including a nucleic acid, such as single-strand DNA, double-strand DNA, RNA and the like, as a template or a primer is introduced into the second storage tank (U-3) 30-3 of the third level liquid-feeding unit. A reagent including a DNA-synthesizing enzyme is introduced into the second storage tank (U-2) 20-3 of the second level liquid-feeding unit. A fluorescent pigment for nucleic acid detection is introduced into the second storage tank (U-1) 10-3 of the first level liquid-feeding unit. A carrier is not contained in the reaction chamber 40 of the liquid-feeding chip illustrated in FIG. 24.

When the liquid-feeding chip according to the present invention is used in nucleic acid amplification, it is preferred to use, like the liquid-feeding chip illustrated in FIG. 24, a liquid-feeding chip which has a reaction chamber 40 having a capacity capable of containing the nucleic acid amplification reaction solution and the respective reagents, and which does not have a waste tank 50 in communication with the reaction chamber 40.

By initially rotating at a first rotation speed, the nucleic acid amplification reaction solution including the template flows to the reaction chamber 40. After stopping rotation, by increasing and decreasing the temperature of the reaction chamber portion with a heating/cooling means, the nucleic acid or primer which will serve as the template is formed to have a single strand. Then, by rotating a second time at the first rotation speed, the reagent including the DNA-synthesizing enzyme flows to the reaction chamber 40. After stopping rotation, by increasing and decreasing the temperature of the reaction chamber portion with the heating/cooling means, amplification of the nucleic acid can be carried out. By rotating a third time at the first rotation speed, the reagent including a fluorescent pigment flows to the reaction chamber 40. The produced fluorescence corresponding to the amount of amplified nucleic acid is measured by a measurement means to measure for the presence of amplification and the amplification amount, thereby detecting nucleic acid.

In addition to the template and the primer, a reagent that can be used in nucleic acid amplification may be appropriately included in the nucleic acid amplification reaction solution. Examples of reagents that can be used in nucleic acid amplification include dNTP, a buffer, a primer, magnesium salts such as $MgSO_4$, potassium salts such as KCl, a surfactant, a protein such as BSA, DMSO, and betaine. The primer and dNTP may have been subjected to various kinds of modification. Examples of modification include fluorescent labeling such as with FITC, Cy3, Cy5, Alexa, FAM, labeling with a quencher such as Tamra, and biotinylation. The above-described DNA-synthesizing enzyme in the reagents is not specifically limited, as long as it can be used in nucleic acid amplification. An example of such a DNA-synthesizing enzyme is DNA polymerase, and a preferred example is strand-displacing DNA polymerase. If RNA is used as the template, a reverse transcription enzyme may be used in addition to the DNA-synthesizing enzyme. Further, a fluorescent pigment for staining and detection of the amplified nucleic acid may be used as the fluorescent pigment for nucleic acid detection. Examples of the fluorescent pigment include ethidium bromide, SYBR Green 1, Pico Green, Oxazole yellow and the like. Further, the reagent used in the nucleic acid amplification may optionally be included in the reagent including the DNA-synthesizing enzyme or the reagent including the fluorescent pigment.

The liquid-feeding chip according to the present invention can be used in immunological measurement.

An example will now be described of immunological measurement using the liquid-feeding chip according to the present invention with reference to FIG. 4. First, a carrier to which an antibody for identifying a measurement target substance is bound is contained in the reaction chamber 40. A solution obtained by mixing an enzyme-labeled secondary antibody in a specimen including an antigen which will act as the measurement target is introduced into the second storage tank (U-3) 30-3 of the third level liquid-feeding unit. A washing solution is introduced into the second storage tank (U-2) 20-3 of the second level liquid-feeding unit. A solution including an enzyme reaction substrate is introduced into the second storage tank (U-1) 10-3 of the first level liquid-feeding unit.

By initially rotating at a first rotation speed, the solution obtained by mixing an enzyme-labeled secondary antibody in a specimen including an antigen which will act as the measurement target passes through the reaction chamber 40. At this stage, solid-phase anti-bodies bind with a complex of the antigen and the enzyme-labeled secondary antibody. After stopping rotation, a washing solution is passed through the reaction chamber 40 by rotating a second time at the first rotation speed.

After stopping the second rotation, the reagent including the enzyme reaction substrate flows into the reaction chamber 40 by rotating a third time at the first rotation speed. After stopping rotation, the enzyme reaction product produced corresponding to the amount of the target antigen for measurement is measured by a measuring means, thereby determining the amount of the target antigen for measurement.

When the liquid-feeding chip according to the present invention is used in immunological measurement, the reagent to be introduced into the tanks in the liquid-feeding chip is not limited to the various above-described solutions and reagents. Reagents which are commonly used in immunological measurement may also be used. Examples of reagents used in immunological measurement include a labeled antibody (secondary antibody) labeled with fluorescence or an enzyme, an antigen, a washing solution, a fluorescent or luminescent substrate, a fluorescent substrate, a chromogenic substrate and the like.

Industrial Applicability

The liquid-feeding chip, the analysis method, and the feeding method according to the present invention can be preferably applied in the analysis and examination of a specimen, such as a biosample collected from a living body.

The invention claimed is:

1. A liquid-feeding chip for feeding a liquid utilizing action of centrifugal force and gravity while the liquid-feeding chin is mounted on a rotation apparatus by rotating the chip around an axis of rotation, comprising:
   a first storage tank provided in the chip, into which the liquid can be introduced when rotation of the chip is stopped, and
   two or more liquid-feeding units arranged in a plurality of levels adjacent to each other, each liquid-feeding unit being composed of a first holding tank, a second holding tank positioned in a direction of gravity with respect to the first holding tank when the chip is in use, and a channel B which extends from the first holding tank in the direction of gravity, connects the first holding tank with the second holding tank, and feeds a liquid from the first holding tank into the second holding tank by gravity, a first holding tank arranged at a first level being connected with a channel A which extends from the first storage tank toward an outer circumferential side with respect to the axis of rotation which is along the direction of gravity,
   wherein 1) the adjacent liquid-feeding units are connected by a channel C which extends from a second holding tank of a liquid-feeding unit arranged at an upper level to an outer circumferential side during rotation and is in communication with a first holding tank of another liquid-feeding unit arranged at a lower level, and 2) at least one of the plurality of liquid-feeding units further comprises either a) or b):
   a) a second storage tank positioned closer to the axis of rotation than the second holding tank, and a channel E which directly connects the second holding tank and the second storage tank, or
   b) a second storage tank positioned closer to the axis of rotation than the first holding tank arranged at a lower level liquid feeding unit, and a channel E which connects the first holding, tank and the second storage tank.

2. A liquid-feeding chip for feeding a liquid among a plurality of tanks in the chip utilizing action of centrifugal force and gravity while the liquid-feeding chip is mounted on a rotation apparatus and is rotated around an axis of rotation, the liquid-feeding chip comprising:
   a first storage tank provided in the liquid-feeding chip, into which the liquid can be introduced;
   a channel A which has one end connected to the first storage tank, all or a part of the channel A extending in a direction toward an outer circumference with respect to the axis of rotation which is along the direction of gravity;

a plurality of liquid-feeding units each composed of a first holding tank, a second holding tank arranged in a direction of gravity with respect to the first holding tank when the chip is in use, and a channel B which has one end connected to the first holding tank and another end connected to the second holding tank, a liquid being fed via the channel B from the first holding tank into the second holding tank by gravity, the plurality of liquid-feeding units being arranged in a plurality of levels in which one end of the channel A is connected to the first holding tank arranged at the highest level; and a channel C which connects adjacent liquid-feeding units, all or a part of the channel C extending in an outer circumferential direction with respect to the axis of rotation so that a second holding tank arranged at an upper level is connected with a first holding, tank of another liquid-feeding unit arranged at a lower level, wherein at least one of the plurality of liquid-feeding units further comprises either a) or b):

a) a second storage tank positioned closer to the axis of rotation than the second holding tank, and a channel E which directly connects the second holding tank and the second storage tank, or b) a second storage tank positioned closer to the axis of rotation than the first holding tank arranged at a lower level liquid-feeding unit, and a channel B which connects the first holding tank and the second storage tank.

3. The liquid-feeding chip according to claim 1. wherein the channel B comprises an inflection portion midway along the channel which is inflected in an outer circumferential direction with respect to the axis of rotation.

4. The liquid-feeding chip according to claim 1, wherein the channel B comprises a section midway along the channel which has a smaller channel cross-sectional area than a channel cross-sectional area at a connecting portion with the first holding tank.

5. The liquid-feeding chip according to claim 1, wherein an angle formed by at least a part of the channel B and the axis of rotation is larger than an angle formed by at least apart of the Channel C and the axis of rotation.

6. The liquid-feeding chip according to claim 1, further comprising a channel D) which is connected to the second holding tank of the liquid-feeding unit arranged at a lowest level, the channel D extending in an outer circumferential direction with respect to the axis of rotation.

7. The liquid-feeding chip according to claim 1, wherein one or more second holding tanks further comprise a channel into which a liquid can be introduced, and wherein at least two of the first storage tanks and the second holding tanks included in the liquid-feeding chip store liquids different from each other in advance.

8. The liquid-feeding chip according to claim I, wherein at least one of the first holding tanks and the second holding tanks is connected via a plurality of channels with the first storage tank at a upper level, than that holding tank and/or with the first holding tank and the second holding tank at a upper level , so that different liquids introduced from the plurality of channels can be mixed, 9. The liquid-feeding chip according to claim 1, further comprising a removably-mounted reagent reservoir unit, and wherein the first storage tank is provided in the removably-mounted reagent reservoir unit.

10. An analysis method comprising:
preparing the liquid-feeding chip according to claim 1;
introducing a liquid into the first storage tank;
mounting the liquid-feeding chip into which the liquid has been introduced on a rotation apparatus and rotating the rotation apparatus at a first rotation speed to feed the liquid to the first holding tank; and
rotating the liquid-feeding chip at a second rotation speed which is slower than the first rotation speed, or by stopping rotation, to feed the liquid to the second holding tank so as to analyze the liquid.

11. The analysis method according to claim 10. wherein the liquid is any one selected from the group consisting of blood, urine, spinal liquid, saliva, phlegm, a cell suspension, a disrupted cell suspension, a nucleic acid solution, a virus suspension, a food extract, a soil extract, a blocking solution, a diluent, a denaturing agent, a labeled antibody, a labeled antigen, a non-labeled antibody, a non-labeled antigen, a labeling substance, a luminescent substrate, a fluorescent substrate, a chromogenic substrate, a hydrogen peroxide solution, a washing solution, a protein denaturing agent, a cell lysate, an enzyme solution, a labeled nucleic acid, a non-labeled nucleic acid, a primer, a probe, avidin, streptoavidin, a buffer solution, a pH adjusting solution, a hybridization solution, and an enzyme reaction terminate solution, or selected from the group consisting of a combination of two or more of these or a reaction product of two or more of these, 12. A liquid-feeding method, comprising:
preparing the liquid-feeding chip according to claim 1;
introducing a liquid into the first storage tank;
mounting the liquid-feeding chip into which the liquid has been introduced on a rotation apparatus and rotating the rotation apparatus at a first rotation speed to feed the liquid to the first holding tank;
(a) rotating the liquid-feeding chip at a second rotation speed which is slower than the first rotation speed, or stopping rotation to feed the liquid to the second holding tank; and
(b) rotating the liquid-feeding chip at the first rotation speed to feed the liquid to the first holding tank at a lower level.

13. The liquid-feeding method according to claim 12, wherein the steps (a) and (b) are further repeated once or twice or more.

* * * * *